(12) United States Patent
Gong

(10) Patent No.: US 6,495,680 B1
(45) Date of Patent: Dec. 17, 2002

(54) HELICES AND NANOTUBES ON FOLDING COMPOSITIONS AND METHOD OF MAKING SAME

(75) Inventor: Bing Gong, Toledo, OH (US)

(73) Assignee: The University of Toledo, Toledo, OH (US)

(*) Notice: Subject to any disclaimer, the term of this patent is extended or adjusted under 35 U.S.C. 154(b) by 0 days.

(21) Appl. No.: 09/535,022

(22) Filed: Mar. 24, 2000

(51) Int. Cl.$^7$ ............................................ C07D 487/22
(52) U.S. Cl. ...................... 540/456; 560/139; 560/153; 560/158; 530/317; 530/321; 528/271
(58) Field of Search ........................... 540/456; 564/153, 564/158

(56) References Cited

PUBLICATIONS

Zhu et al., J. Am. Chem. Soc., vol. 122, No. 17, May 3, 2000, pp. 4219–4220.*
Eisenberg, Bob, Ionic Channels in Biological Membranes: Natural Nanotubes, Acc. Chem. Res. (1998), 117–123; published on the web Feb. 20, 1998.
Marsh, Derek, Peptide models for Membrane Channels, Biochem. J. (1996) 315, 345–361; printed in Great Britain.
Smart, Oliver S., Goodfellow, Julia M., Wallace, B.A., The Pore Dimensions of Gramacidin A, Biophysical Journal (Dec. 1993), vol. 65, 2455–2460.
Ikigai, Hajime, Nakae, Taiji, Assembly of the α–Toxin–Hexamer of *Staphylococcus aureus* in the Liposome Membrane, The Journal of Biological Chemistry (Feb. 1987), vol. 262, No. 5, 2156–2160; printed in the U.S.A.
Palmer, Michael, Vulicevic, Ivan, Saweljew, Peter, Valeva, Angela, Kehoe, Michael, Bhakdi, Sucharit, Streptolysin O: A Proposed Model of Allosteric Interaction Between A Pore–Forming Protein and Its Target Lipid Bilayer, Biochemistry (1998), 37, 2378–2382; published on the web Feb. 3, 1998.
Bayley, Hagan, Building Doors into Cells, Scientific American (Sep. 1997), 62–67.
Panchal, Rekha G., Cusack, Evelyn, Cheley, Stephen, Bayley, Hagan, Tumor Protease–Activated, Pore–Forming Toxins From a Combinatorial Library, Nature Biotechnology (Jul. 1996), vol. 14, 852–856.
Fernandez, Tania, Bayley Hagan, Ferrying Proteins to the Other Side, Nature Biotechnology (May 1998), vol. 16, 418–420.
Braha, Orit, Walker, Barbara, Cheley, Stephen, Kasianowicz, John J., Song, Langzhou, Gouaux, J. Eric, Bayley, Hagan, Designed Protein Pores as Components for Biosensors, Chemistry & Biology (1997), vol. 4, No. 7, 497–505.
Song, Langzhou, Hobaugh, Michael R., Shustak, Christopher, Cheley, Stephen, Bayley, Hagan, Gouaux, J. Eric, Structure of Staphylococcal α–Hemolysin, a Heptameric Transmembrane Pore, Science (Dec. 1996), vol. 274, 1859–1866.

Akerfeldt, Karin S., Lear, Jim D., Wasserman, Zelda R., Chung, Laura A., Degrado, William F., Synthetic Peptides as Models for Ion Channel Proteins, Acc. Chem. Res. (1993), 26, 191–197.
Gokel, George W., Murillo, Oscar, Synthetic Organic Chemical Models for Transmembrane Channels, Acc. Chem. Res. (1996), 29, 425–432.
Ghadiri, M. Reza, Granja, Juan R., Milligan, Ronald A., McRee, Duncan E., Khazanovich, Nina, Self–Assembling Organic Nanotubes Based on a Cyclic Peptide Architecture, Nature (Nov. 1993), vol. 366, 324–327.
Bryson, James W., Betz, Stephen F., Lu, Helen S., Suich, Daniel J., Zhou, Hongxing X., O'Neil, Karyn T., Degrado, William F., Protein Design: A Hierarchic Approach, Science (Nov. 1995), vol. 270, 935–941.
Gellman, Samuel H., Foldamers: A Manifesto, Accounts of Chemical Research (1998), vol. 31, No. 4, 173–180; published on web Mar. 13, 1998.
Appella, Daniel H., Christianson, Laurie A., Karle, Isabella L., Powell, Douglas R., Gellman, Samuel H., β–Peptide Foldamers: Robust Helix Formation in a New Family of β–Amino Acid Oligomers, J. Am. Chem. Soc. (1996), 118, 13071–13072.
Seebach, Dieter, Overhand, Mark, Kuhnle, Florian N.M., Martinoni, Bruno, β–Peptides: Synthesis by Arndt–Eistert Homoligation with Concomitant Peptide Coupling. Structure Determination by NMR and CD Spectroscopy and by X–Ray Crystallography. Helical Secondary Structure of a β–Hexapeptide in Solution and Its Stability towards Pepsin, Helvetica Chimica Acta (1996), vol. 79, 913–941.
Cho, Charles Y., Moran, Edmund J., Cherry, Sara R., Stephans, James C., Fodor, Stephen P.A., Adams, Cynthia L., Sundaram, Arathi, Jacobs, Jeffrey W., Schultz, Peter G., An Unnatural Biopolymer, Science (Sep. 1993), vol. 261, 1303–1305.

(List continued on next page.)

*Primary Examiner*—Richard L. Raymond
(74) *Attorney, Agent, or Firm*—Emch, Schaffer, Schaub & Porcello, Co., L.P.A.

(57) ABSTRACT

Helical oligomer and polymer compositions that form nanotubes are described. The compositions comprise a plurality of aromatic substituents linked by at least one amide group. The compositions have a curved backbone due to intramolecular hydrogen bonds that rigidify the amide linkage of each amide group to each aromatic substituent and due to an interaction between the aromatic substituents such that the curved backbone is stabilized. The helical compositions are formed by ridigifying the amide group, which is flanked on each side by the aromatic substituents, by introducing intramolecular hydrogen bonds into a linkage between the amide group and each aromatic substituent such that the compositions fold into a helical shape when the amide linkages are meta to each other.

61 Claims, 33 Drawing Sheets

PUBLICATIONS

Nelson, James C., Saven, Jeffery G., Moore, Jeffrey S., Wolynes, Peter G., Solvophobically Driven Folding of Non-biological Oligomers, Science (Sep. 1997), vol. 277, 1793–1796.

Appella, Daniel H., Christianson, Laurie A., Karle, Isabella L., Powell, Douglas R., Gellman, Samuel H., Synthesis and Characterization of trans–2–Aminocyclohexanecarboxylic Acid Oligomers: An Unnatural Helical Secondary Structure and Implications for β–Peptide Tertiary Structure, J. Am. Chem. Soc. (1999), 121, 6206–6212; published on web Jun. 10, 1999.

Gong, Bing, Yan, Yinfa, Zeng, Huaqiang, Skrzypczak–Jankunn, Ewa, Kim, Yong Wah, Zhu, Jin, Ickes, Harold, A New Approach for the Design of Supramolecular Recognition Units: Hydrogen–Bonded Molecular Duplexes, J. Am. Chem. Soc. (1999), 121, 5707–5608; published on web May 29, 1999.

Gin, Mary S., Yokozawa, Tsutomu, Prince, Ryan B. Moore, Jeffrey S., Helical Bias in Solvophobically Folded Oligo(Phenylene Ethynylene)s, J. Am. Chem. Soc, (1999), 121, 2643–2644; published on web Mar. 9, 1999.

Yang, Dan, Qu, Jin, Li, Bing, Ng, Fei–Fu, Wang, Xue–Chao, Cheung, Kung–Kai, Wang, De–Ping, Wu, Yun–Dong, Novel Turns and Helices in Peptides of Chiral α–Aminoxy Acids, J. Am. Chem. Soc. (1999), 121, 589–590; published on web Jan. 9, 1999.

Hanessian, Stephen, Luo, Xuchong, Schaum, Robert, Michnick, Stpehen, Design of Secondary Structures in Unnatural Peptides: Stable Helical γ–Tetra–, Hexa–, and Octapeptides and Consequences of α–Substitution, J. Am. Chem. Soc, (1998), 120, 8569–8570; published on web Aug. 5, 1998.

Seebach, Dieter, Abele, Stefan, Sifferlen, Thierry, Hanggi, Martin, Gruner, Sibylle, Seiler, Paul, Preparation and Structure of β–Peptides Consisting of Geminally Disubstituted $β^{2,2}$– and $β^{3,3}$–Amino Acids: A Turn Motif for β–Peptides, Helvetica Chimica Acta (1998), vol. 81, 2218–2243.

Armand, Philippe, Kirshenbaum, Kent, Goldsmith, Richard A., Farr–Jones, Shauna, Barron, Annelise E., Truong, Kiet T.V., Dill, Ken A., Mierke, Dale F., Cohen, Fred E., Zuckerkmann, Ronald N., Bradley, Erin K., NMR Determination of the Major Solution Confirmation of a Peptoid Pentamer with Chiral Side Chains, Proc. Natl, Acad. Sci. (Apr. 1998), vol. 95, 4309–4314.

* cited by examiner

M = H+ or metal ions

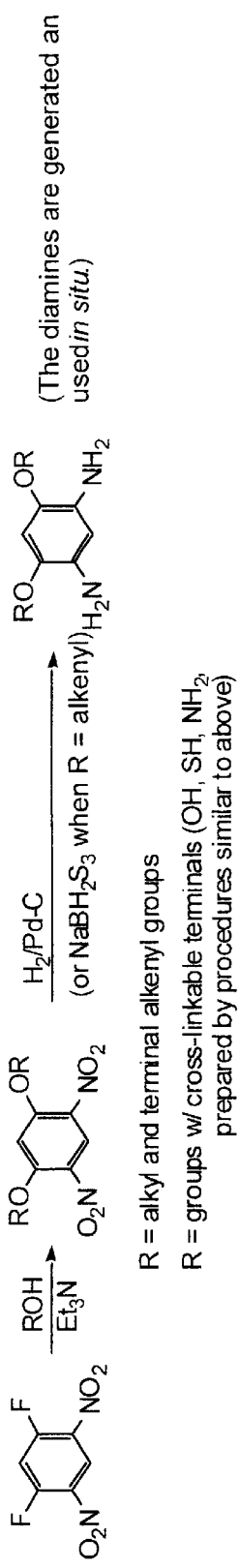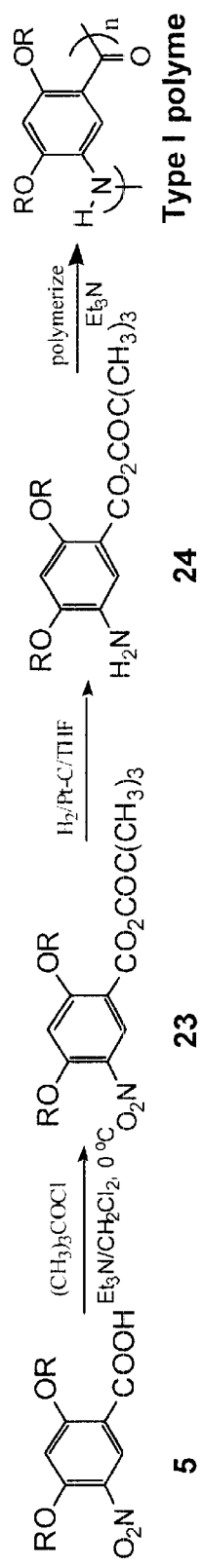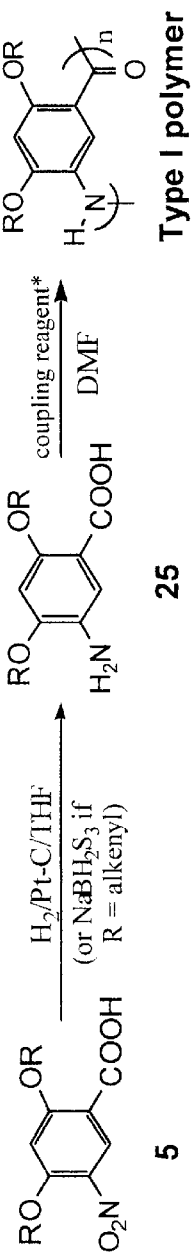
Fig. 8b
Fig. 8c

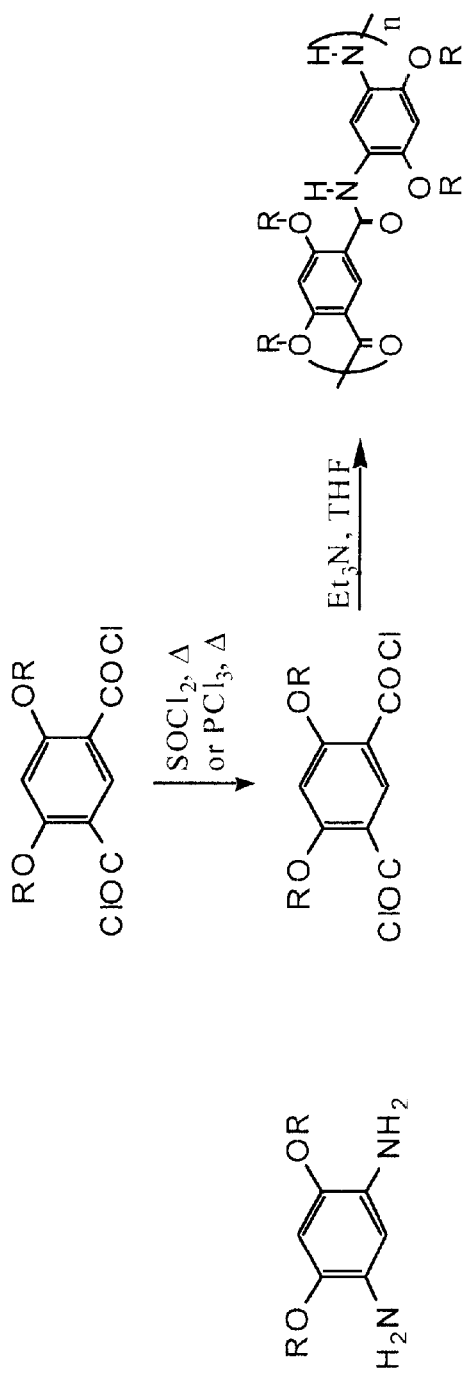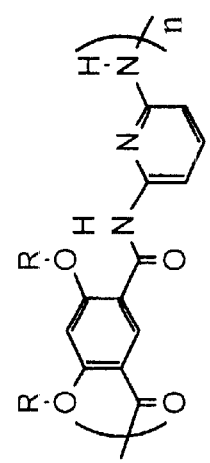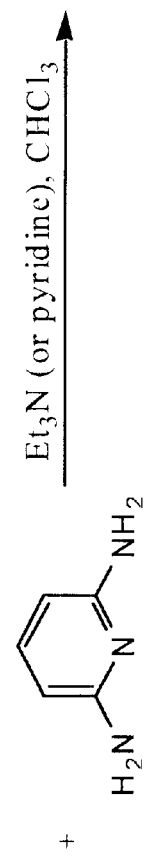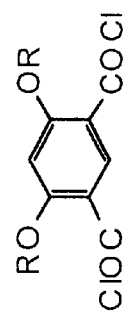
Fig. 8d
Fig. 8e

Hydrophobic  Hydrophobic  Charged

HELICES AND NANOTUBES ON FOLDING COMPOSITIONS AND METHOD OF MAKING SAME

BACKGROUND OF THE INVENTION

Naturally occurring membrane channels and pores are formed from a large family of diverse proteins, peptides and organic secondary metabolites whose vital biological functions include control of ion flow, signal transduction, molecular transport and production of cellular toxins. (Eisenberg, B. (1998) Ionic channels in biological membranes: natural nanotubes. Acc. Chem. Res. 31:117; Hill, B. (1992) Ionic Channels of Excitable Membranes $2^{nd}$ edn. (Sinauer Associates, Sunderland); Gennis, R. B. (1989) Biomembranes, Molecular Structure and Function, Springer, New York). Many pore-forming peptides, such as gramicidin and alamethicin, function by creating pores within the plasma membrane of a target cell (Marsh, D. (1996) Peptide models for membrane channels. Biochem. J. 315(pt2):345; Smart, O. S.; Goodfellow, J. M.; Wallace, B. A. (1993) The pore dimensions of gramicidin A. Biophys. J. 65(6):2455; Ritov, V. B.: Tverdislova, I. L.; Avakyan, T. Yu; Menshikova, E. V.; Leikin, Yu N.; Bratkovskaya, L. B.; Shimon, R. G. (1992) Alamethicin-induced pore formation in biological membranes. Gen. Physiol. Biophys. 11(1):49). Pore-forming protein toxins, such as the *Staphylococcus aureus* α-hemolysin and *Streptococcus streptolysin-O*, act similarly by boring holes into the cell membranes. (Bayley, H. (1997) Toxin structure: part of a hole? Curr. Biol. 7(12):R763; Ikigai, H.; Nakae, T. (1987) Assembly of the alpha-toxin-hexame of Staphylococcus aureus in the liposome membrane. J. Biol. Chem 262:2156; Palmer, M; Vulicevic I.; Saweljew, P.; Valeva, A.; Kehoe, M.; Bhakdi, S. (1998) Biochem. 37(8):2378. Streptolysin-O: a proposed model of allosteric interaction between a pore-forming protein and its target lipid bilayer. α-Hemolysin has received intense interest as a prototype for artificial molecular gatekeepers that can be used for the design of drugs, (Bayley, H. (1997) Building doors into cells. Sci. Am. 277 (September):62); (Panchal, R. G.; Cusak, E.; Cheley, S.; Bayley, H. (1996) Turnor-protease-activated, pore-forming toxins from a combinatorial library, Nature Biotechnol 14:852) drug delivery agents (Fernandex, T.; Bayley, H. (1998) Ferrying proteins to the other side. Nature Biotechnol. 16(5):418) or highly sensitive and selective biosensors. (Braha, O.; Walker, B.; Cheley, S.; Kasianowicz, J. J.; Song, L.: Gouaux, J. E.; Bayley, H. (1997) Designed protein pores as components for biosensors. Chem. Biol. 4:497). Difficulties associated with using protein molecules in these designs include heat and mechanical instability, immunogenicity in biotherapeutics, and the like.

Lying at the center of the pore assembled from seven molecules of α-hemolysin (and many other pore-forming proteins) is a nanosize channel. (Song, L; Hobaugh, M. R.; Shustak, C.; Cheley, S.; Bayley, H.; Gouaux, J. E. (1996) Structure of Staphylococcal α-hemolysin, a heptameric transmembrane pore. Science 274:1859). The transmembrane segment, a β-barrel, of the channel ranges from 14 Å to 26 Å in diameter and 52 Å in length. The interior of the β-barrel was found to be primarily hydrophilic, while the exterior has a hydrophobic belt.

Despite the existence of numerous chemical models as artificial transmembrane channels, (Alkerfeldt, K. S.; Lear, J. D.; Wasserman, Z. R.; Chung, L. A.; DeGrado, W. F. (1993) Acc. Chem. Res. 26:191; Gokel, G. W.; Murillo, O. (1996) Acc. Chem. Res. 29:425) the design and synthesis of artificial systems that can mimic the biological function of natural compounds is still a formidable task. A successful model rivaling the structural robustness and versatility as observed in the natural systems has not been seen until the present invention. Such a model requires a tube-or barrel-like structure with a nanosized, hydrophilic internal cavity and a hydrophilic internal cavity and a hydrophobic outside surface.

The self-assembly of cyclic peptides (Ghadiri, M. R.; Granja, J. R.; Milligan, R. A.; McRee, D. E.; Khazanovich, H. (1993) Self-assembling organic nanotubes based on a cyclic peptide architecture. Nature 366:324) provides an example of self-assembling nanotubes. However, Ghadiri's nanotubes do not suit the above purpose since these tubes consist of stacked peptide rings. Due to the structure of these cyclic peptides and the way the tubes form, it is difficult to imagine how different molecular switches could be put site-specifically into these nanotubes.

Other approaches have been described (Bryson, J. W.; Betz, S. F; Lu, H. S.; Suich, D. J.; Zhou, H. X.; O'Neil, K. T.; DeGrado, W. F. (1995) Protein design: a hierarchic approach. Science 270:935) toward manipulating nanoscale structures by designing oligomeric bundles of α-helices. Models for transmembrane helical oligomers may lead to simplified systems for designing pore-forming agents. (Dieckmann, G. R.; DeGrado, W. F. (1997) Modeling transmembrane helical oligomers Curr. Opin. Struct. Biol. 7(4):486). The advantage of these helix bundles is that they allow precise control over the positions to be modified, enabling site-specific engineering of the nanostructures with both natural and unnatural amino acids. However, one disadvantage of these designed helix bundles is that they may have the same instability and immunogenicity problems associated with natural peptides and proteins.

Until the present invention, a question that still remained was whether unnatural systems provide nanosize, tube-like structures. Various prior art approaches to folding structures have been taken, involving primarily the use of intramolecular hydrogen bonding, or donor-acceptor interactions. (Gellman, S. H. (1998) Foldamers: a manifesto. Acc. Chem. Res. 31:173) Examples of folded, potentially functionalizable structures include β-peptides and peptoid oligomers and many others involving unnatural backbones. (Appella, D. H; Christianson, L. A.; Karle, I. L; Powell, D. R.; Gellman, S. H. (1996) Beta-Peptide foldamers: robust helix formation in a new family of beta-amino acid oligomers. J. Am. Chem. Soc. 118:13071–13072; Seebach, D.; Overhand, M.; Kuhnle, F. N. M.; Martinoni, B.; Oberer, L.; Hommel, U.; Widmer, H. (1996) Beta-Peptides: synthesis by Arndt-Eistert homologation with concomitant peptide coupling. Structure determination by NMR and CD spectroscopy and by X-ray crystallography. Helical secondary structure of a β-hexapeptide in solution and its stability towards pepsin. Helv. Chim. Acta 79:913; Armand, P.; Kirshenbaum, K.; Falicov, A.; Dunbrack, R. L. Jr.; Dill, K. A.; Zuckermann, R. N.; Cohen, F. E. (1997) Chiral N-substituted glycines can form stable helical conformations. Fold. Des. 2(6):369; and others such as Cho, C. Y.; Moran, E. J.; Cherry, S. R.; Stephans, J. C.; Fodor, S. P.; Adams, C. L.; Sundaram, A.; Jacobs, J. W.; Schultz, P. G. (1993) An unnatural biopolymer, Science 261:1303). However, few examples have shown folded structures with cavities similar to those seen in protein molecules.

One approach toward building nanotubes involved designing oligomers that undergo polar solvent-driven folding (Nelson, J. C.; Saven, J. G.; Moore, J. S.; Wolynes, P. G.

(1997) Solvophobically driven folding of nonbiological oligomers. Science 277:1793). While a helical conformation with nanosized tubular cavity was proposed for the folded structure, this system was, however, unsuitable for designing pore-forming agents since the interior is quite hydrophobic.

The assembly of well-defined protein secondary structures, such as α-helix, β-sheet, and turns, leads to a bewildering array of tertiary structures. (Branden, C.; Tooze, J., *Introduction to Protein Structure*, 2nd ed.; Garland Publishing: New York, 1998). As the first step toward developing artificial oligomers and polymers that fold like biomacromelecules, there is currently an intense interest in designing unnatural building blocks that adopt well-defined secondary structures. (Gellman, S. H., Acc. Chem. Res., 1998, 31, 173; Appella, D. H.; Christianson, L. A.; Karle, I. L.; Powell, D. R.; Gellman, S. H., *J. Am. Chem. Soc.*, 1999, 121, 6206. Gong, B.; Yan, Y.; Zeng, H.; Skrzypcak-Jankun, E.; Kim, Y. W.; Zhu, J.; Ickes, H., *J. Am. Chem. Soc.*, 1999, 121, 5607. Gin, M. S.; Yokozawa, T.; Prince, R. B.; Moore, J. S., *J. Am. Chem. Soc.*, 1999, 121, 2643. Yang, D.; Qu, J.; Li, B.; Ng, F.-F; Wang, X.-C.; Cheung, K.-K.; Wang, D.-P; Wu, Y.-D., *J. Am. Chem. Soc.*, 1999, 121, 589. Hanessian, S.; Luo, X.; Schaum, R.; Michnick, S., *J. Am. Chem. Soc.*, 1998, 120, 8569. Seebach, D.; Abele, S.; Stifferlen, T.; Hanggi, M.; Gruner, S.; Seiler, P., *Helv. Chim. Acta*, 1998, 81, 2218. Armand, P.; Kirshenbaum, K.; Goldsmith, R. A.; Farr-Jones, S.; Barron, A. E.; Truong, K. T.; Dill, D. A.; Mierke, D. F.; Cohen, F. E.; Zuckermann, R. N.; Bradley, E. K., *Proc. Natl. Acad. Sci. U.S.A.*, 1998, 95, 4309).

SUMMARY OF THE INVENTION

This invention relates to a novel class of compositions such as oligomers and polymers that automatically fold into helices with large (10 Å to 50 Å) tubular cavities. The compositions are comprised of aromatic rings linked by amide groups. The backbone of the composition is curved due to the incorporation of intramolecular hydrogen bonds that rigidify the amide linkages. The backbone is long enough to fold back on itself, leading to a left- or right-handed helical conformation.

The helical composition is further stabilized by stacking of the aromatic rings of neighboring spiral turns. Such a backbone-based helical programming leads to helical compositions whose folded conformation is resilient toward structural variation of the side groups which, in turn, determine the outside surface properties. The interior of the helical composition features the amide-O atoms, which make the tubular cavities hydrophilic. The internal diameters of the helices are adjustable by combining meta- and para-disubstituted benzene rings or by using larger aromatic rings, such as derivatives of naphthalene and anthracene.

These helices, as nanotubes, are useful as artificial pore-forming agents which are readily functionalized. Molecular gatekeepers based on these nanotubes are designed by including biochemical, chemical, and physical switches into the structures. The present invention is especially useful for design of pore-forming drugs, drug carriers, novel chiral hosts for chiral recognition and catalysis, and sensitive membrane-bond ion-channels and sensors.

The helical compositions of present invention are also useful as pore-forming drugs, membrane-bound nanopores for DNA sequencing, and new optical materials.

The present invention also relates to methods for making nanotube compositions and the nanotube compositions themselves. These nanotube compositions mimic part or all of the pore-forming function of α-hemolysin and other similar proteins. Artificial pores that behave in a controlled and predictable fashion are synthesized according to the present invention. These nanotube compositions are useful as drugs, to deliver drugs or as biosensors to detect toxic chemicals.

The compositions have a nanosized barrel- or tube-like structure with a hydrophilic interior and a hydrophobic exterior. To avoid the problems associated with protein molecules, the nanotube compositions have mechanical and heat stability for designing sensors and other materials, or are biologically inert (enzyme resistant and non-immunogenic) in biotherapeutics. To control the pore's ability to open and close, the nanotube compositions are readily modifiable to enable molecular switches to be incorporated into one or more specific sites.

The present invention also relates to new nanotube compositions based on the folding of designed oligomers. These nanotube compositions satisfy all the requirements, as defined above, for designing pore-forming agents, for the design of various desirable functional agents.

The present invention provides well-defined, folded conformations through rigidification of backbones. The conformations have (i) electrostatically negative, hydrophilic interior cavities; (ii) modifiable exterior surfaces; and (iii) adjustable cavity size.

In one aspect of the present invention, the conformations are useful for transmembrane channels and pores.

In this aspect, the following applications are particularly useful:

(i) Synthesis of Compositions: monomers with membrane-compatible side groups (selected α-amino acid side chains); sequence-specific synthesis of oligomers on solid-supports.

(ii) Characterization of Compositions: x-ray crystallography; 1D and 2D NMR; IR; facilitated by sequence information from synthesis.

(iii) Membrane studies: liposome-based proton transport; single channel conductance measurements; hydrophilic (sugar or dye) molecule transport; nanotube orientation in lipid bilayer as probed by polarized attenuated total reflectance (ATR), grazing-angle reflection-absorption, and FT-IR spectroscopy.

(iv) Gated nanotubes with physical or biochemical switches.

(v) Cytotoxicity assays (with the oligomers alone or with drug transport).

Still other applications include: (i) Channel- and pore-forming reagents (toxins), (ii) ion- and small molecule-transport (drug delivery), and (iii) Gated pore- and channels, and (controlled drug delivery and cell-based sensors).

In another aspect of the present invention, the conformations are useful as nanoporous polymers. In this aspect, the following applications are particularly useful (i) Synthesis of Compositions: monomers with hydrophobic and cross-linkable side chains; polymerization of monomers (mostly one-pot); block copolymers with polymerization of short oligomers.

(ii) Characterization of Compositions: gel permeation chromatography; light scattering; IR and UV (intramol. H-bonds; hypochromic effects of stacked aromatic rings—folding of polymers).

(iii) Formation of polymer films: by simple casting, and by solid- and liquid-phase, lateral cross-linking of polymer chains (oxidation, metathesis, and lateral polymerization).

(iv) Permeate flux and solute selectivity of the porous materials.

(v) Confinement and parallel alignment of close-packed guest molecules in bulk polymeric materials. Binding of guest molecules into the tubular cavities (probed by affinity columns and/or by fluorescence quenching); nanowires from reduction of metal ions absorbed into the tubular cavities.

Still other applications include: (i) polymer films with a single pore size: highly efficient materials for separation and purification; (ii) tubular cavities for aligning interesting chromophores: electro-optic materials with the robustness of polymers and the flexibility of host-guest interactions; and, (iii) templates for the fabrication of conducting nanowires.

DESCRIPTION OF FIGURES

(FIG. 1b side view. FIG. 1c top view). A tubular cavity with a diameter of ~10 Å can be seen. Hydrogen atoms are omitted for clarity of view.

FIG. 8a–e are schematic diagrams showing (a) synthesis of monomers for synthesizing polymers for derivatives of IIa and IIb and (b) derivatives of III; synthesis of polymers; (c) homopolymers of type IIa monomers; (d) type IIb and III monomers; and (e) copolymers of type IIb monomers and 2,6-diaminopyridine.

DESCRIPTION OF THE INVENTION

The present invention relates to the synthesis of nanotube compositions which comprises the rigidification of an amide group flanked by two aromatic rings. According to one aspect of the invention, the rigidification is accomplished by introducing intramolecular H-bonds. An oligomer having amide-liked benzene rings forms a curved backbone when the amide linkers are meta to each other. The existence of intramolecular H-bonds provides the curved conformation to the oligomer backbone.

I: Type I backbone compositions are homo-oligomers and homopolymers with one type of monomer.

The rigidification of the amide-linked structure A (type I backbone) below, by forming two intramolecular hydrogen-bonded rings, leads to a six-membered ring (S(6)), and a five membered ring (S(5)). (Berstein, J.; Davis, R. E.; Shimoni, L; Chang, N.-L. (1995) Patterns in hydrogen bonding: functionality and graph set analysis in crystals. Angew. Chem. Int. Ed. Engl. 34:1555).

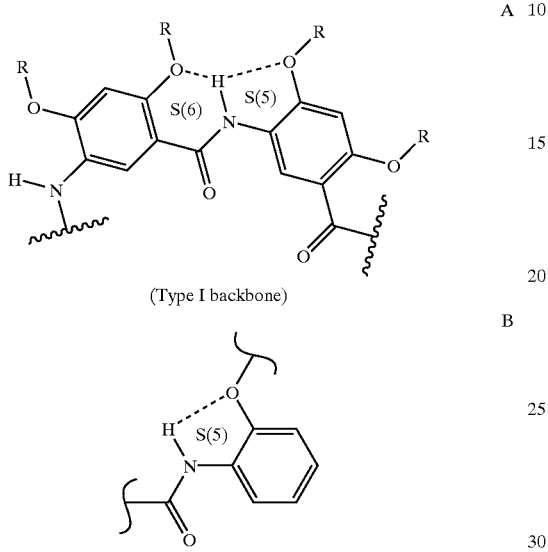

(Type I backbone)

Figure 1A:
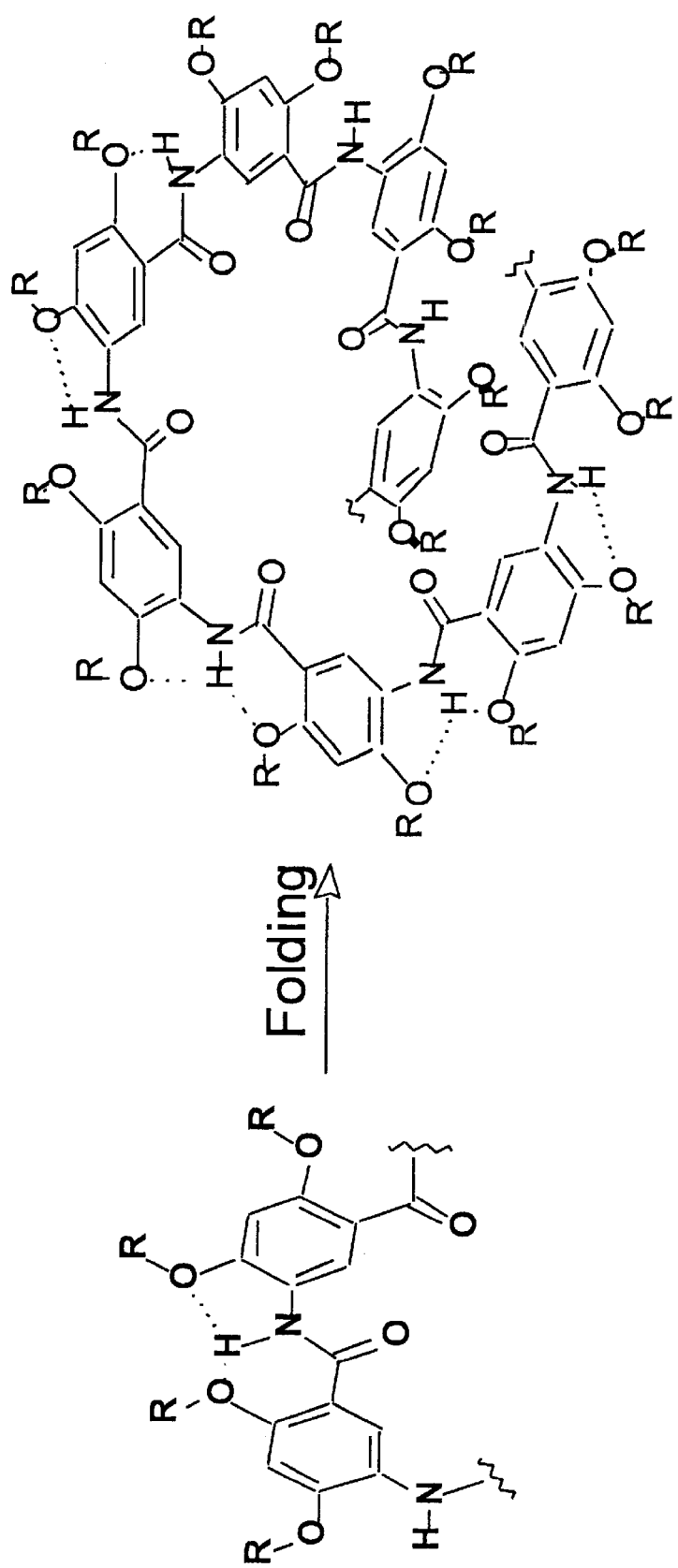
FIG. 1a shows type I homo-oligomers and homopolymers with one type of monomer.

The unnatural folding oligomers and polymers not only results in molecules with sophisticated properties, but also leads to new insights into folding of natural biomacromolecules, as shown in FIG. 1a. The oligoamides of the present invention have backbones that adopt well-defined, crescent conformations.

Structure A shows diaryl amide oligomers. The presence of the three-center hydrogen bonding system consisting of the S(5) and S(6) type intramolecularly hydrogen bonded rings lead to rigidification of the amide linkage, resulting in a well-defined conformation. Oligoamides containing such amide linkages have a rigid backbone. With the two amide linkages on the same benzene ring being meta to each other, the resulting oligomer have a crescent confirmation. Hamilton et al. reported oligomers generated from anthranilic acid, pyridine-2,6-dicarboxylic acid, and 4,6-dimethoxy-1,3-phenylenediamine units, in which intramolecular H-bonds enforce a helical (or curved) conformation: Hamuro, Y; Geib, S. J.; Hamilton, A. D., *J. Am. Chem. Soc.*, 1997, 119, 10587.

Intramolecular hydrogen bonds occur in preference to intermolecular ones, particularly the six-member-ring (S(6)) type. The S(5)-type five-member ring is also common, which exists in a large number of compounds. An almost planar arrangement of the amide group and the phenyl rings is observed, with close positioning of the O atom and amide-H (O . . . H, from 2.08 Å to 2.26 Å), consistent with the formation of cyclic intramolecular hydrogen bonds.

A. Computational Analysis

Conformations other than Structure C (favored, 0 kcal/mol), such as Structures Ca (less favored, 11.6 kcal/mol), Cb (less favored, 14.51 kcal/mol), and Cc (least favored, 27.37 kcal/mol), shown below, resulted from 180 degree rotation of each benzene-carboxamide bond, are less stable than C due to the loss of the very favorable intramolecular hydrogen bonding interactions and the introduction of repulsive electrostatic interactions between the non-bonding electron pairs of the O atoms.

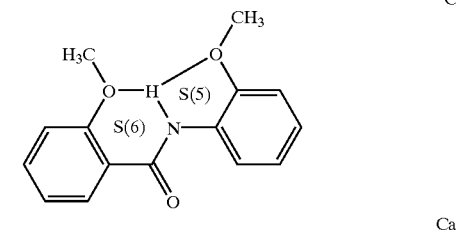

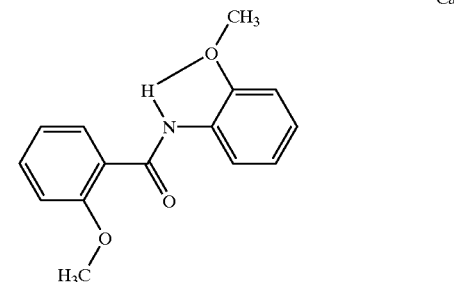

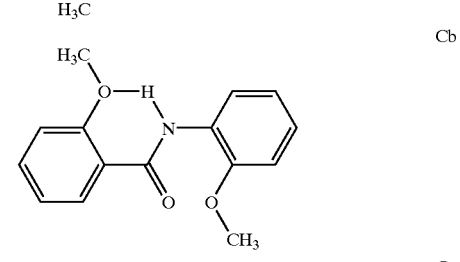

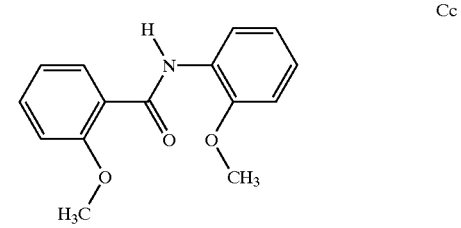

Ab initio calculations (in vacuo) using the Gaussian 94 program were carried out in order to compare the stabilities of these four conformations. The Jaguar program (Jaguar v3.0, Schordinger, Inc.; Portland, Oreg., 1997) was used to obtain relative energies of the optimized structures. Geometry optimizations were carried out at the B3LYP/6-31 G(d) level, whereas the LMP2/6-311 G(d) method was used for single point energy calculations. Conformations Ca, Cb, and Cc are constrained to be planar. The computational results indicate that there are significant differences in the relative energies of the four conformations: Structure C is overwhelmingly favored over Structures Ca, Cb. and Cc. The desired conformation, C, has two strong hydrogen bonds with O . . . H=1.87 Å (S(6)) and 2.14 Å (S(5)), respectively.

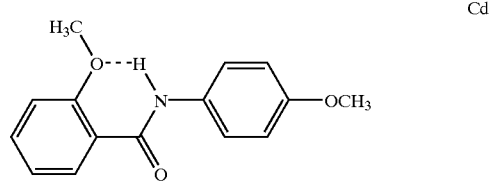

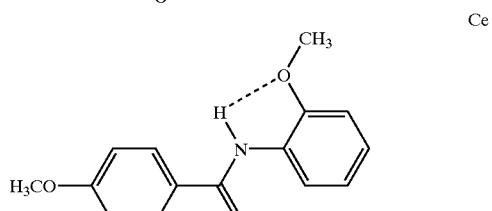

¹H-NMR studies in CDCl₃ indicated significant downfield shift of the amide NH signal of C (10.60 ppm, independent of concentration) compared to those of the reference compounds Cd (at 10 mM, 9.691 ppm) and Ce (at 10 mM, 8.497 ppm), showing formation of the bifurcated hydrogen bonds. The conformation of C in solution was then examined by NOE difference spectroscopy (600 MHz, 300 K). In CDCl₃, on saturating the amide-H signal, NOE enhancements were observed on both methoxy groups of the benzoate (δ4.04; 1.14%) and the aniline (δ3.92; 0.80%) residues. Similar NOE enhancements were also detected in the polar solvent DMSO-d₆: on saturating the amide-H signal, enhancements on the benzoate and aniline methoxy signals were 1.05% and 0.64%, respectively. These results show the existence of the S(5)- and S(6)-type hydrogen bonds and thus the conformation of amide C in solution. The rigid conformation of C (existing in the very polar solvent DMSO) allows for the design of oligomers that adopt well-defined conformations in highly competitive solvents.

Figure 1B:
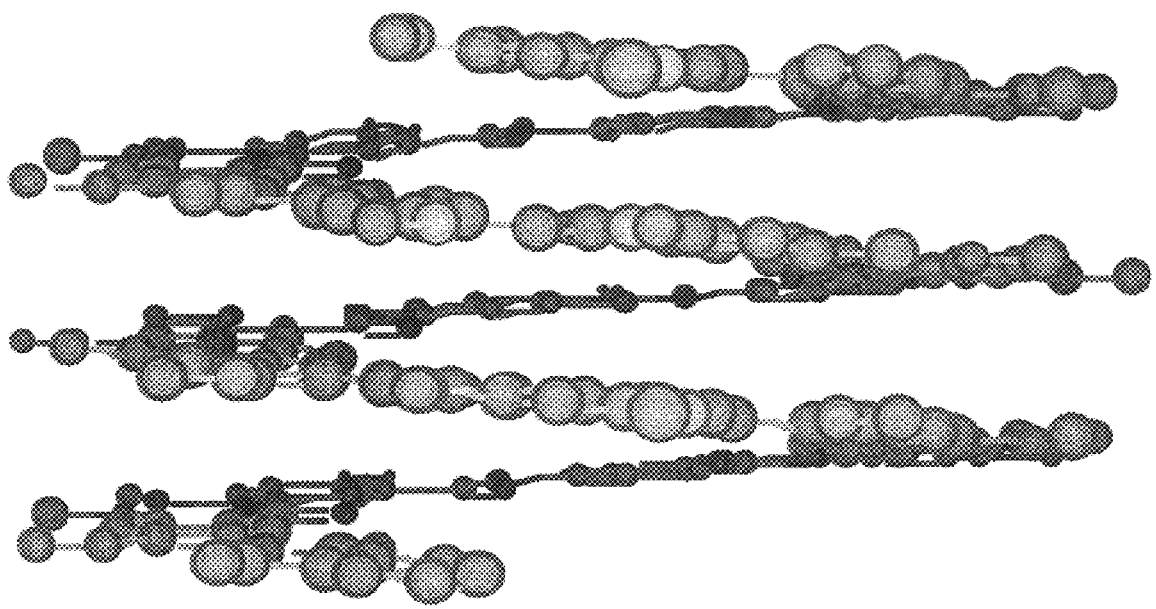
FIGS. 1b and 1c show energy-minimized ($MM_2$) helical conformation of G. The calculation was carried out with all of the amide linkages constrained to be planar.
Figure 1C:
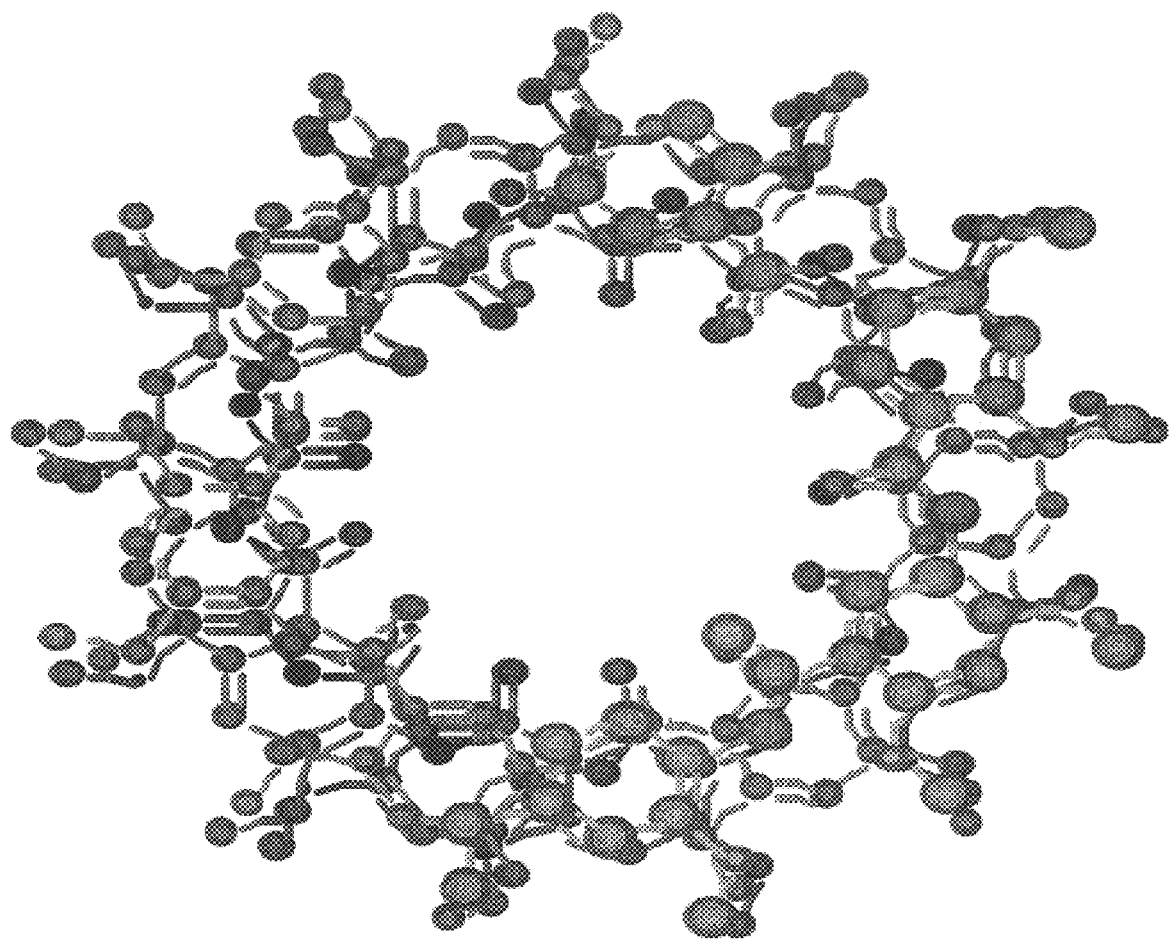

The conformation of a 20-ring oligomer, G, was studied by energy minimization using the CaChe program (MM₂ force field) on a Macintosh computer. All amide groups of G are constrained to be planar. As shown in FIGS. 1b and 1c, the energy-minimized conformation of G involves a helix with a pitch of 3.7–3.8 Å and an internal diameter of ~10 Å. Each helical turn consists of ~6.2 residues, since the (O=)C—N—C bond angle is slightly larger than 120°~124°). Each amide group and the benzene ring it attaches to has a small dihedral angle of ~2.5°.

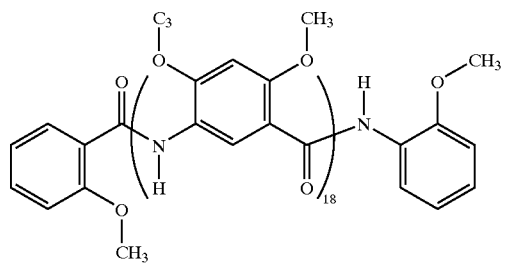

G

B. X-Ray Crystallography

As shown below, results from X-ray crystallography studies have clearly established the validity and feasibility of the method of the present invention.

1. The Crystal Structure of the Two-Ring Compound H

Figure 2A:
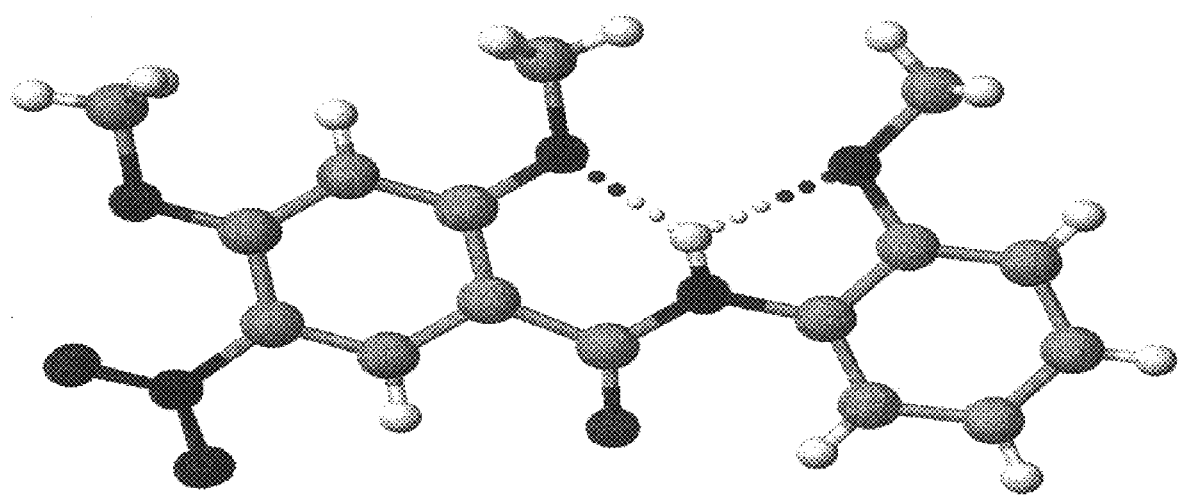
FIG. 2a shows Compound H and shows the existence of two intramolecular hydrogen bonds in its crystal structure.

The crystal structure of H provides conclusive evidence for the existence of S(5)- and S(6)-type intramolecular hydrogen bonds, as shown in FIG. 2a. In the solid state, H shows exactly the type of conformation as expected. Two intramolecular hydrogen-bonded rings. S(6) (O . . . H=1.926 Å, O . . . N=2.654 Å, N—H . . . O=141.5°) and S(5) (O . . . H=2.147 Å, O . . . N=2.576 Å, N—H . . . O=110.4°), are observed. These values are very close to the above calculated results.

The molecules of H crystallize in the space group P-1 (triclinic. a=7.1651 Å, b=8.3342 Å, c=13.2149 Å; α=73.4°, β=84.7°, γ=88.5°). The planes of the two aromatic rings in H are parallel to each other and to that of the amide group, resulting in a flat molecule with a rigid, curved conformation.

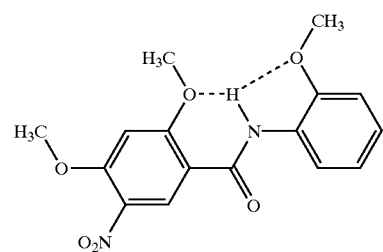

H

Figure 2B:
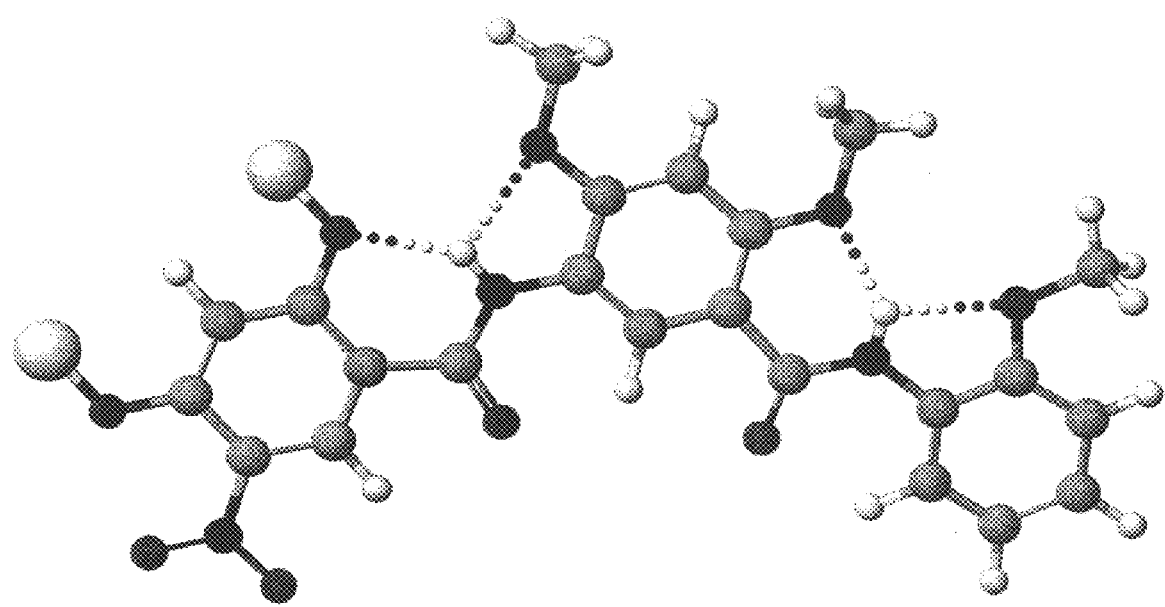
FIG. 2b shows Compound I and shows a curved backbone due to the formation of four intramolecularly hydrogen-bonded rings in its crystal structure. The two decyl chains are represented by two dummy atoms for clarity of view.

2. The Crystal Structures of the Three-Ring (I) and Four-Ring (J) Compounds The rigid, curved conformation is much more evident in the crystal structure of I, as shown in FIG. 2b.

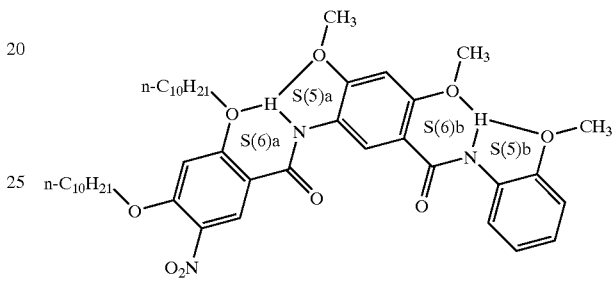

I

There are four hydrogen bonded rings in the structure of I: S(6)a (O . . . H=2.023 Å, O . . . N=2.724 Å, N—H . . . O=138.0°), S(6)b (O . . . H=1.959 Å, O . . . N=2.667 Å, N—H . . . O=138.8°), S(5)a (O . . . H=2.226 Å, O . . . H=2.623 Å, N—H . . . O=108.1°), and (S(5)b (O . . . H=2.162 Å, O . . . N=2.581 Å, N—H . . . O=109.6°). As a result, a curved (crescent) conformation with all the amide-O atoms turning inward is observed. These results indicate that the S(5) and S(6) type intramolecular hydrogen bonds prevail in these structures. More importantly, the two amide O atoms, which point inward and may have repulsive interaction with each other, do not interrupt the overall curved conformation. This is significant since it is an important structural requirement for forming the nanotube compositions of the present invention by using longer analogs. Compound I crystallizes in the space group P-1 (triclinic, a=9.293 Å, b=12.481 Å, c=18.410 Å; α=84.1°, β=85.0°, γ=78.7°). I is flat with all benzene rings in the same molecule lying in the same plane.

X-ray diffraction quality crystals of J have also been obtained. Initial analysis of the X-ray diffraction data indicate that J is similar to I (triclinic, a=12.481 Å, b=12.729 Å, c=17.457 Å; α=100.17°, β=91.07°, γ=101.33°), with a curved backbone and two long chains (the decyl groups).

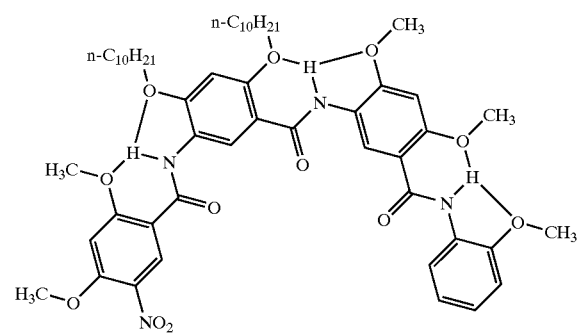

J

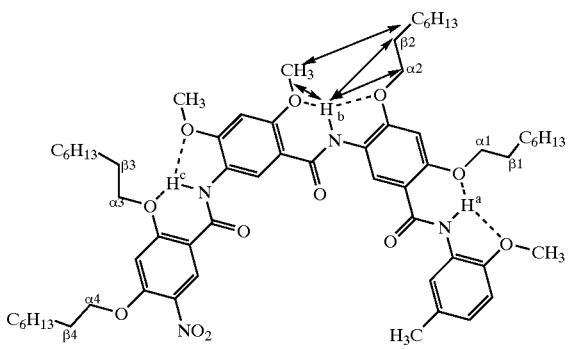

D

Figure 3:
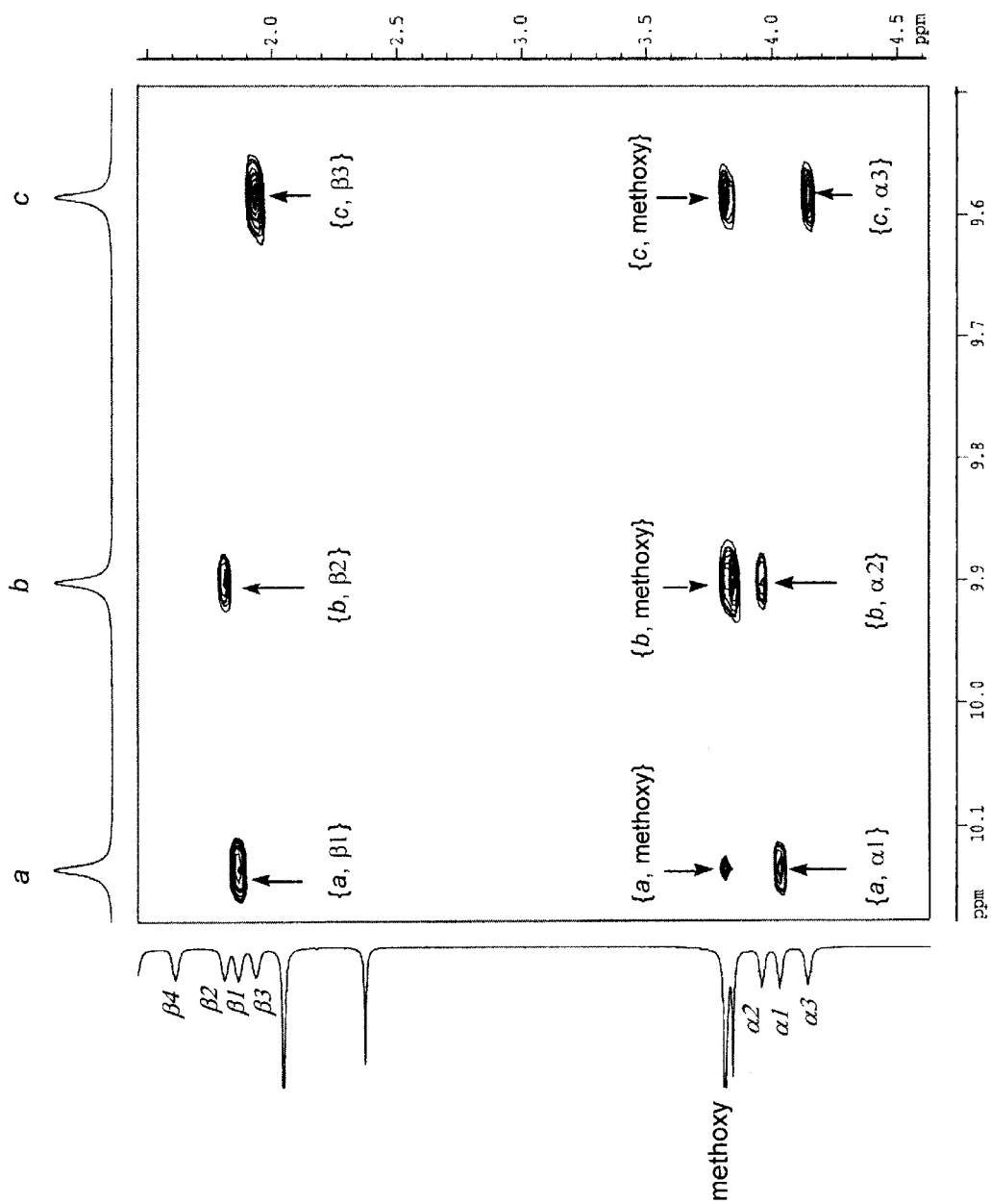
FIG. 3 shows NOESY spectrum of Structure D in $CDCl_3$ (800 MHz, mixing time: 0.3 s). The contacts between amide Hb and the other protons as determined by NOESY spectroscopy are indicated in the structure. Amide Ha and Hc show the same set of contacts. Arrows in the spectrum show contacts depicted in the description of the invention below.

The above analogs of amides C, H and I with longer backbones adopt a well-defined, curved conformation. Tetramer D in solution was thus investigated by 2D (NOESY) $^1$H NMR (CDCl$_3$, 800 MHz, 300K) spectroscopy. At 50 mM, the amide NH signals of D appeared at δ9.58, 9.90 and 10.13 as three well separated peaks. As shown in FIG. 3, two cross peaks corresponding to each of the three amide protons were observed: one with a methoxy group and the other with its neighboring octyloxy α-methylene group. Such contacts show the formation of bifurcated hydrogen bonds between an amide proton and its neighboring alkoxy-O atoms, which provide the most diagnostic evidence for the curved conformation of D. Besides, the NOESY spectrum of D also revealed contacts between the methoxy protons and the, β-methylene protons of the octyloxy groups, providing additional, unequivocal evidence for the proposed curved conformation.

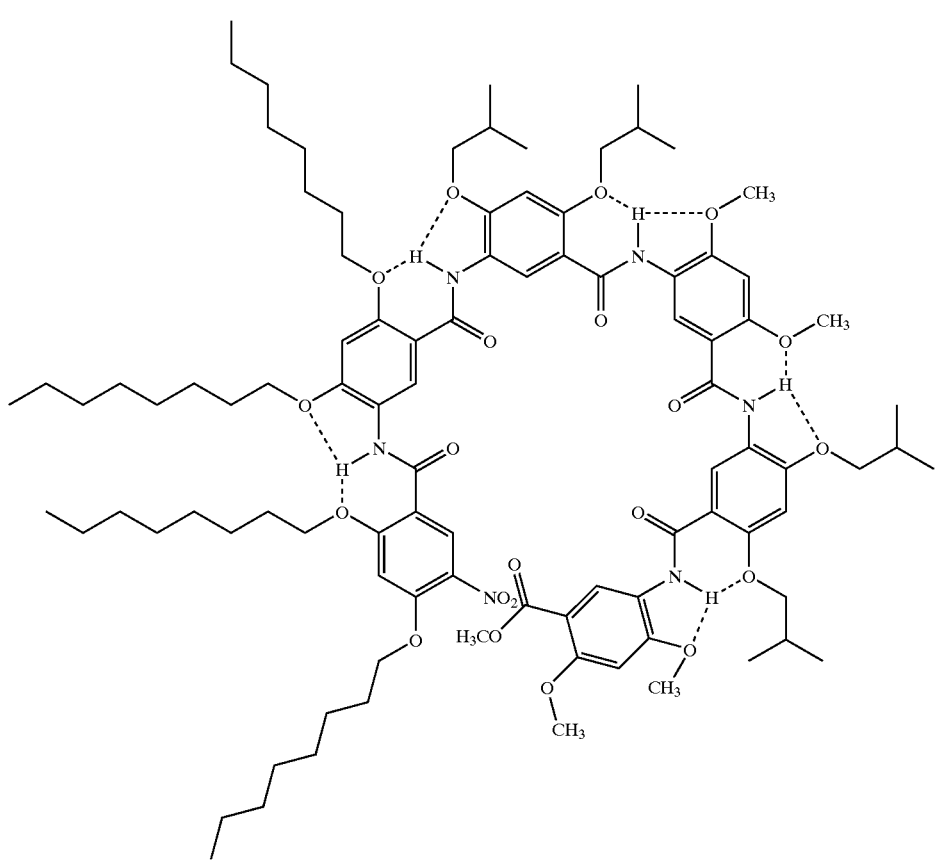

E

The conformation of hexamer E, which makes almost a full circle and thus a nearly closed cavity, was probed by NOESY (CDCl$_3$, 800 MHz, 280K) studies. At 25 mM, the five amide NH signals of E appeared as three groups of peaks: δ9.51 and 9.54 (two partially overlapped peaks, 2H), δ9.69 (single peak, 1 H), δ9.82 and 9.84 (two partially overlapped peaks, 2H). Based on results from D, each amide proton should have two cross peaks corresponding to the three-center hydrogen bonds. The NOESY spectrum of E revealed exactly ten cross peaks between the amide protons and the protons of the alkoxy a-methylene and methoxy groups (3.6 ppm to 4.4 ppm). Two of the four cross peaks corresponding to the two NH signals at around δ9.82 and 9.84 were not completely resolved, but can be clearly identified. These ten cross peaks, corresponding to two contacts for each amide proton, clearly support the curved conformation shown here for E.

A series of oligoamides with well-defined, curved backbones have been made. The persistence of the three-center hydrogen bonds which lead to the rigidification of the backbones has been established. These compounds are prepared from readily available starting materials based on well-established, highly efficient amide chemistry. These oligoamides have folding propensities: the conformations of their backbones depend only on the presence of local intramolecular hydrogen bonds between amide linkages and their adjacent alkoxy groups. The curved backbone confirmation is resilient toward structural variation on the -OR groups. The curved backbone also leads to the formation of a large (~10 Å in E based on computer modeling), hydrophilic cavity. A variety of folding structures with interior cavities include for example, oligomers such as E which can be viewed as acyclic "macrocycles" that selectively bind to metal ions and small molecules. (Vogtle, F.; Weber, E., Angew. Chem. Int. Ed. Engl., 1979, 18, 753). Oligomers with more than six rings (or residues) fold into a new class of helices with large, interior cavities.

C. Behavior of Oligomers

Oligomers such as the homologues H, K, L, M, N, and O are synthesized by treating acid chloride with the corresponding amines. Examining the solubility of these oligomers in organic solvents revealed interesting behavior.

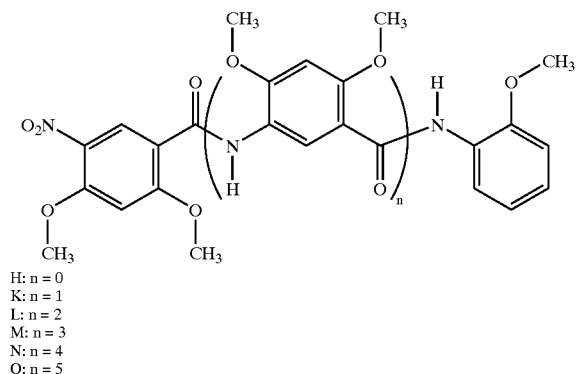

H: n = 0
K: n = 1
L: n = 2
M: n = 3
N: n = 4
O: n = 5

While compound H is soluble in DMF and gives x-ray quality crystals, the three-ring (K), four-ring (L) and five-ring (M) analogs become increasingly insoluble in DMF. The five-ring compound M is only partially soluble in hot DMSO. Freshly prepared K, L and M are soluble when added to DMF but gradually precipitate out upon standing at room temperature. The rates of precipitation are significantly accelerated at elevated temperatures. An opposite trend is observed for the six-ring (N) and seven-ring (O) analogs, which become soluble in DMF than the shorter analogs. O becomes slightly more soluble in chloroform than in DMF. $^1$H-NMR data (in DMSO-$d_6$) show clearly the number of amide-H signals corresponding to the chain size of each oligomer. From H to N, all the amide-H resonances appear at positions >9.2 ppm. For compound O, on the other hand, $^1$H-NMR spectrum (CDCl$_3$) in shows that all, except for one, amide-H signals appear at positions >9.2 ppm. That one amide-H resonance, appears at δ8.86. These data strongly support the folded helical conformation (see example below, Type I oligomers) of this class of oligomers.

Variable temperature (VT) $^1$H-NMR studies on the symmetrical, seven-ring oligomer P in CDCl$_3$ have been carried out to investigate the behavior of the three amide-H signals.

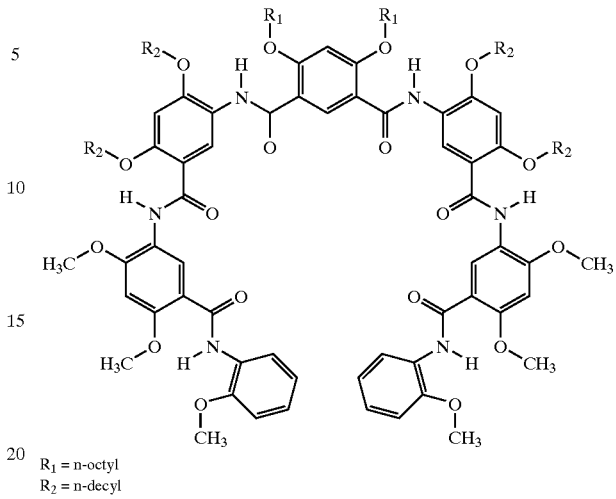

$R_1$ = n-octyl
$R_2$ = n-decyl

At room temperature, the three sets of amide-H signals are well separated, appearing at δ10.27, 9.70 and 9.36, respectively. When the temperature is changed from 25° C. to 65° C., these amide-H signals move upfield. The changes of chemical shifts are 0.061 ppm ($2.0 \times 10^{-3}$ ppm/K), 0.054 ppm ($1.8 \times 10^{-3}$ ppm/K), and 0.076 ppm ($2.5 \times 10^{-3}$ ppm/K). These values from VT $^1$H-NMR studies provide strong evidence for involvement of the amide protons in forming intramolecular hydrogen bonds. Since no abrupt changes in chemical shifts have been observed for these amide-H signals as the temperature changes, it is believed that P adopts the curved conformation in CCl$_3$ solution at elevated temperature as well as at room temperature.

II. Type II a backbone compositions are co-oligomers and copolymers.

A. Type IIa: oligomers of meta-Disubstituted Benzene Residues

Figure 4A:
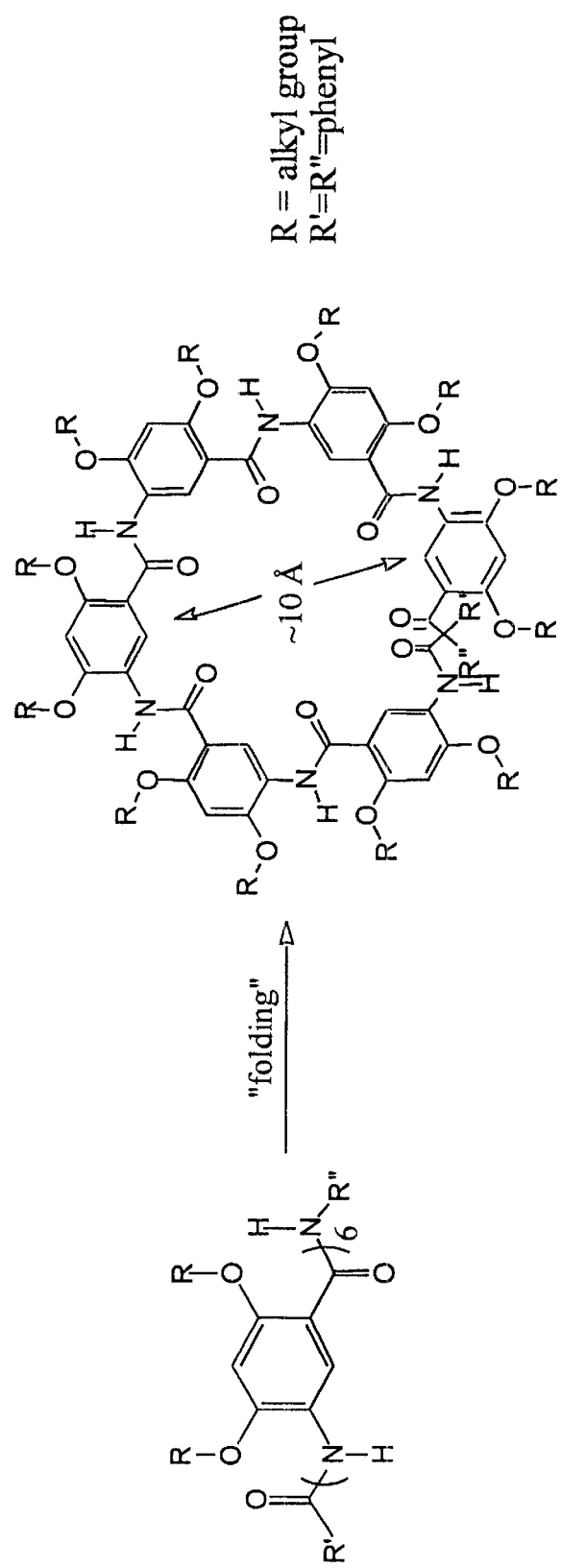
FIG. 4a shows type IIa co-oligomers and homopolymers.

The oligomer/polymer IIa, shown in FIG. 4a, adopts a helical conformation (~1 turn is shown).

Type IIa

Figure 4B:
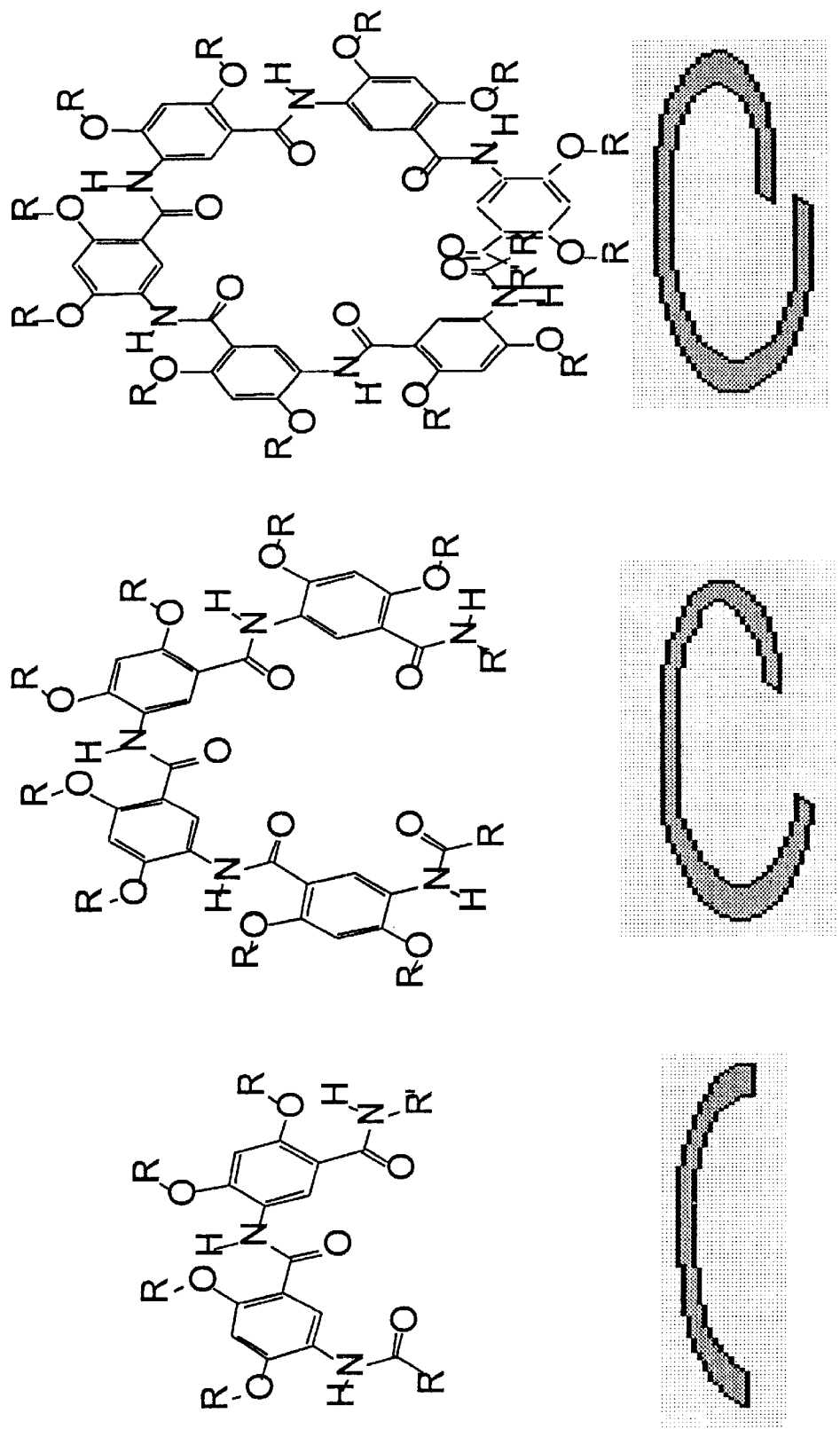
FIG. 4b shows that the two intramolecular hydrogen-bonded rings rigidity the amide linkages, forcing the molecules to adopt a curved conformation. As the Figure shows, the overall curvature of a molecule increases as the number of building blocks in that molecule increases. When the number of residues becomes equal to or greater than six, the molecule adopts a helical conformation, leading to a left- or right-handed helix with a large internal diameter and an outer surface that is readily modifiable.

The building blocks are based on derivatives of the readily available 5-amino-2,4-dihydroxybenzoic acid. Such an oligomer has an overall curved backbone as shown in FIG. 4b.

The curved backbone is forced upon by the meta-disubstituted benzene ring and the two intramolecular H-bonds that rigidify each of the amide linkages in the molecule. As shown in FIG. 4b, when the number of subunits is equal to or greater than six, such an oligomer, adopts a helical conformation in which one end of the molecule lies above the other because of crowding.

An additional stabilizing factor, the aromatic stacking interactions between the benzene rings, sets in for oligomers of more than six residues. For a 12-mer that makes about two full spiral turns, the curved backbone containing the benzene rings and the flat amide groups will stack face-to-face along the helix axis. A helix with a large (in the above case, ~10 Å) tubular cavity is created.

Two driving forces are behind the folding of the helices: (1) two localized intramolecular hydrogen bonds that lead to the rigidification of each of the amide linkages, and (2) aromatic stacking interaction that further stabilizes the formed helix. The two driving forces act cooperatively: the aromatic stacking interaction is possible because of the curved shape of the backbone, the stacking interaction helps stabilize the H-bonds by keeping the helical conformation of the molecule, which partially shields the intramolecular H-bonds, making them less accessible to solvent molecules.

Because of these favorable interactions, the helical conformation has the lowest energy among other possibilities, which is supported by results from both computational and x-ray crystallography studies. Since these two stabilizing factors are associated with the structural characteristics of the backbone, a robust helical structure motif that is versatile as well as resilient toward structural variation of the side groups (OR groups) is formed. As the length of the backbone increases, the aromatic stacking interaction plays an increasingly dominant role, which leads to helices that are stable in polar solvents such as DMO or even water. Materials based on such a structural motif are more robust than those from proteins and are useful for a wide range of applications. Type IIb: Co-oligomers and copolymers based on aromatic diacids and diamines.

Figure 4C:
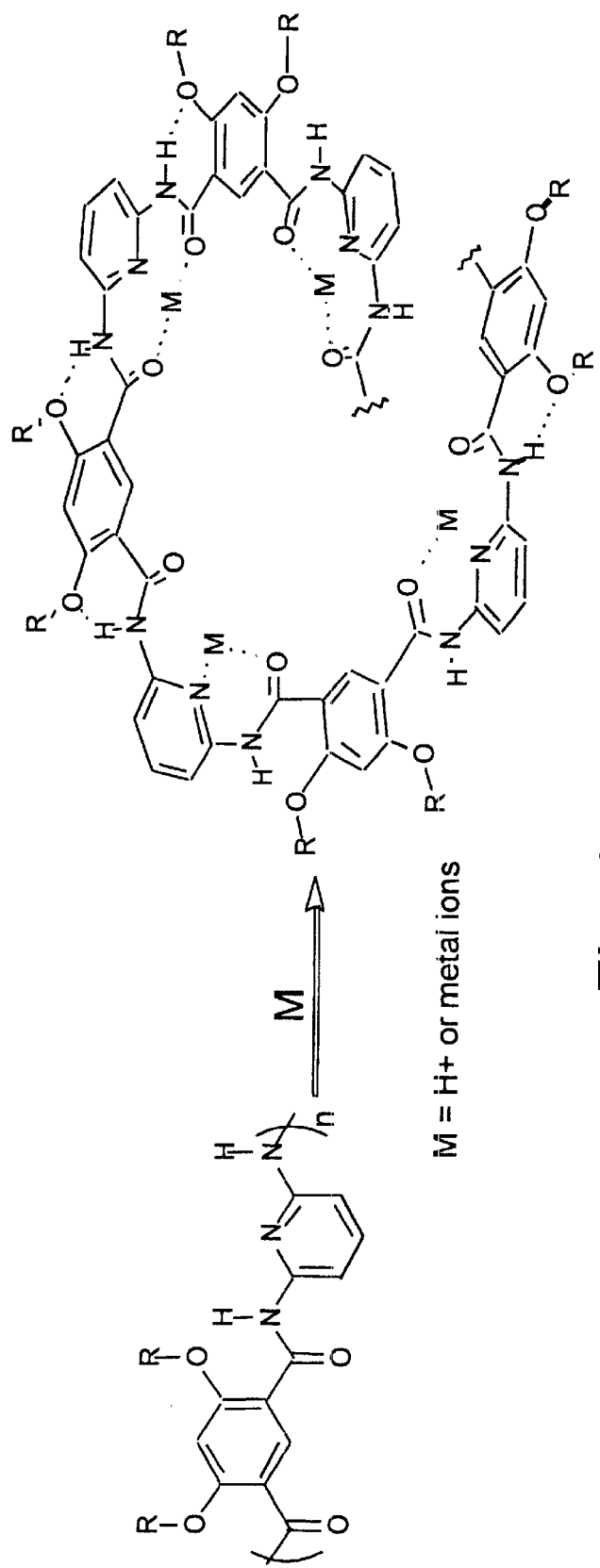
FIG. 4c shows type IIb co-oligomers and copolymers based on aromatic diacids and diamines.

The building blocks are not limited to the above-described compositions. Oligomers such as type IIb, shown in FIG. 4c, (one spiral turn is shown, R=alkyl), based on the diacid and diamine residues as shown, also fold into helical structures. These helices are very similar to type IIa with similar internal diameters and easily modifiable outside surface, but the amide linkages have alternativing orientations.

III: Type III backbone compositions are co-oligomers and copolymers with pH and metal ion dependent folding.

Figure 4D:
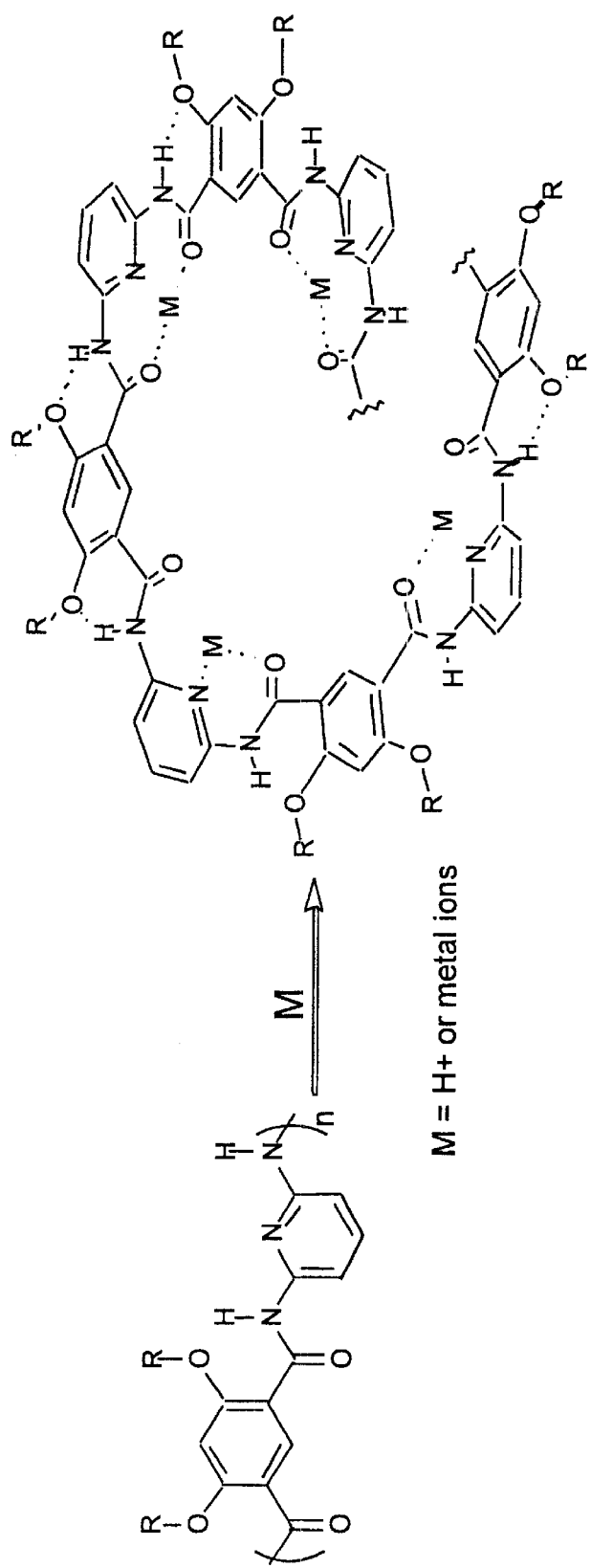
FIG. 4d shows type III co-oligomer and copolymers with pH and metal ion dependent folding.

FIG. 4d shows that folding of this type depends on the acidic environment and/or the presence of metal cations, where M=H⁺ or metal cations.

Figure 4E:
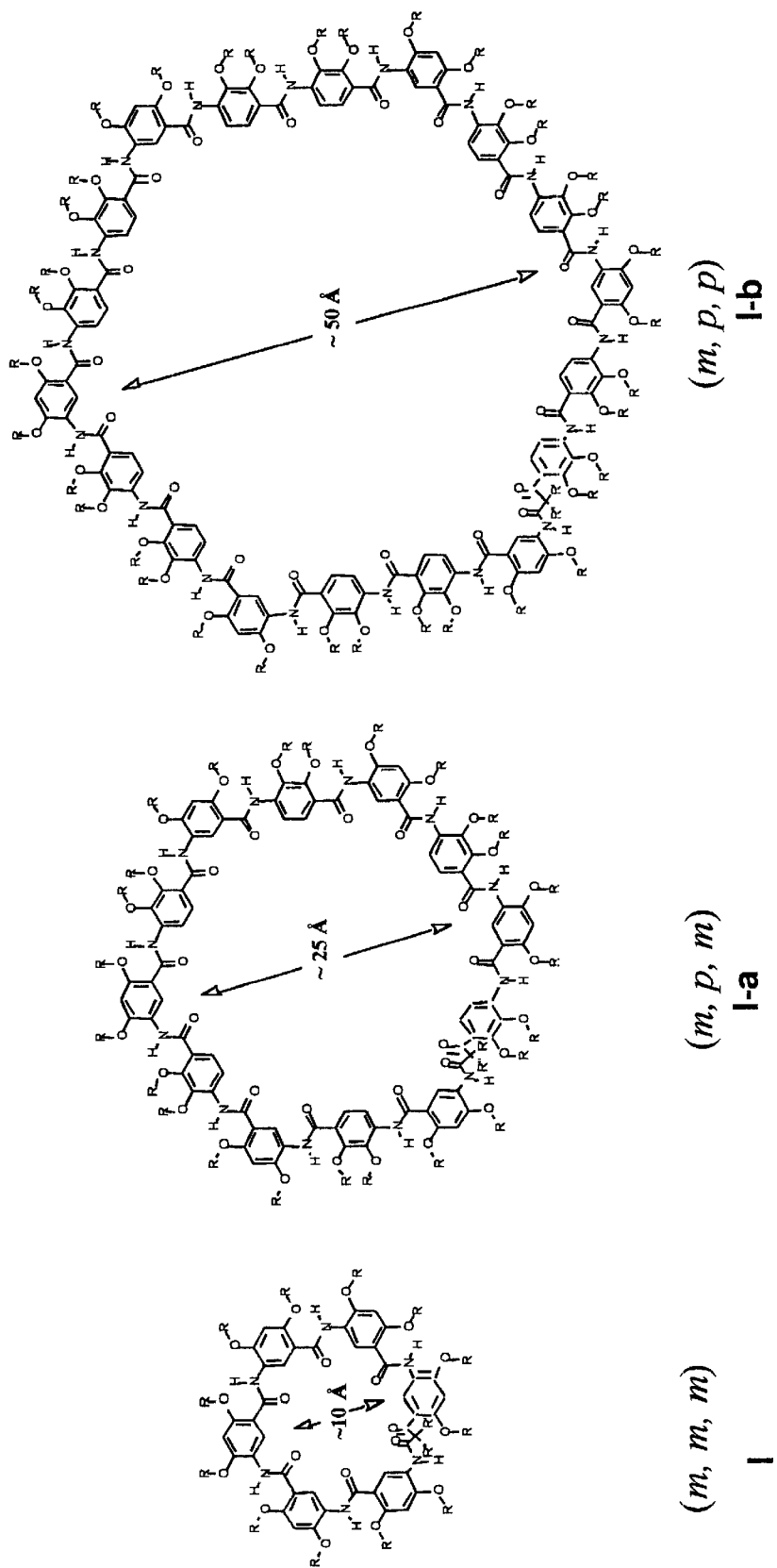
FIG. 4e shows tuning of the size of the interior cavity by changing the curvature of the backbone by combining benzene-derived monomers with the amide linkages on the same ring being meta- and para- to each other.

B. Tuning the Size of the Internal Diameters of the Helices is Done by Changing the Curvature of the Backbone The meta-disubstituted benzene derivatives give helices with internal diameters of the same size (~10 Å). By combining meta- and para-disubstituted benzene derivatives as building blocks, helices of larger internal diameters can be made. Three examples are shown in FIG. 4e. The designs are based on the same principle as described above.

This strategy is very versatile in that it allows the design of helices with internal cavities of various sizes by changing the ratio of the two (meta and para) types of building blocks in an oligomer. For example, oligomers consisting of a sequence of meta-, para-, para-disubstituted benzene rings leads to helices with an internal diameter of ~50 Å.

Analogs of Type IIb co-oligomers and copolymers with adjustable interior cavities are similarly designed based on the corresponding diacid and diamines.

Figure 4F:
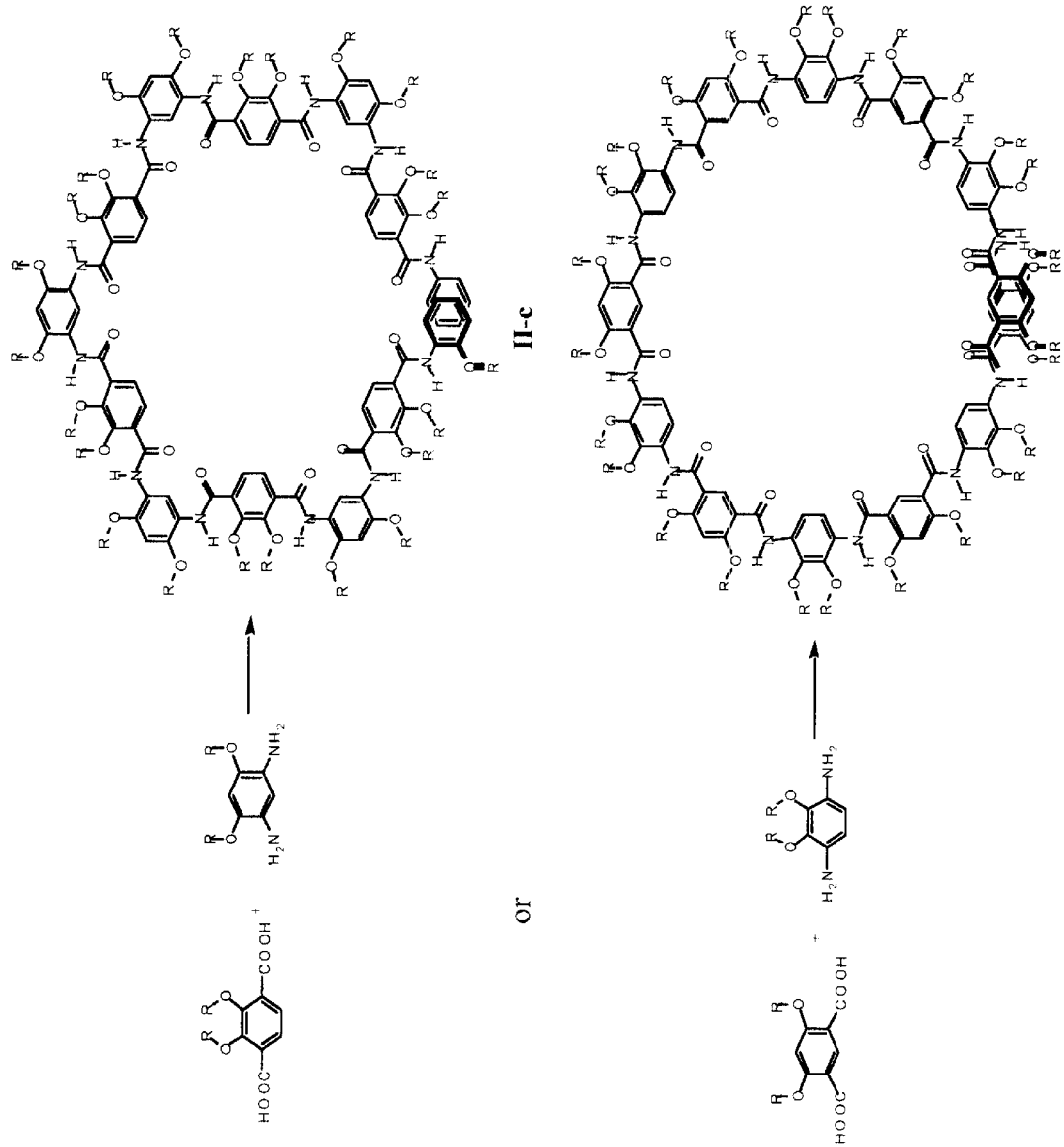
FIG. 4f shows analogs co-oligomers and copolymers with adjustable interior cavities that are based on the corresponding diacid and diamines.

As shown in FIG. 4f, by combining the monomers for IIc and IId in appropriate ration, the interior cavities of the resulted oligomers and polymers are further increased in a way similar to I-d.

The above method of formation is also used to design oligomers and polymers similar to type III by replacing the diamine units in IIc with 2,6-diaminopyride (IIIa) and the diacid in IIb with pyridine-2,6-dicaboxylic acid (IIIb). The folding of type IIIa or IIIb oligomers and polymers, like that of type III, is pH or metal ion dependent.

By designing monomers based on larger aromatic rings, the size of the interior cavities is adjusted. As shown below, monomers such as amino acids (X=NH₂, Y=COOH), diacids (X=Y=COOH), and diamines (X=Y=NH₂), which are derived from naphthalene and anthracene, lead to oligomeric and polymeric helices with adjustable, functionalizable cavities.

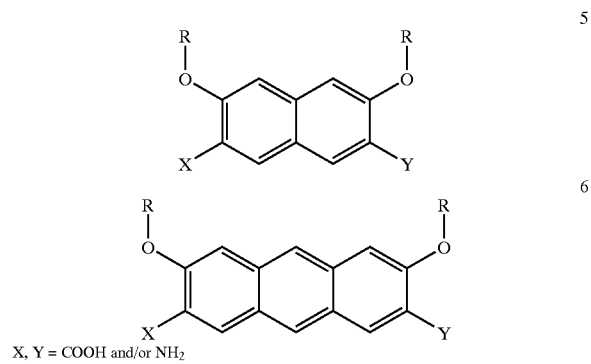

X, Y = COOH and/or NH₂

The side group R determines the outside surface properties of the oligomers and polymers. Three different types of oligomers and polymers can be obtained depending on the types of side groups selected:

(1) Hydrophobic oligomers and polymers: R=linear and branched chain alkyl groups (from one carbon to 20 and longer) and aryl groups (phenyl, benzyl, naphthyl etc.).

(2) Hydrophilic oligomers and polymers: R=alkyl or aryl groups with polar terminal functional ends such as —OH, —COOH, —NH₂, —NH₃⁺, —N⁺R'₃, etc.

(3) Membrane compatible oligomers and polymers: R=—CH₂CH₂C₆H₅, —CH₂C₆H₄—p—OH, —CH₂COOCH₃, —CH₂CONH₂, —CH₂CH₂CONH₂, —CH₂COOCH₂CH₂—(3-indolyol).

C. Type Q: pH- and Metal Ion-Modulated Folding: Oligomers Based on 4,6-Dialkoxy-isophthalic Acid and 2,6-Diaminopyridine The design is based on the fact that 2,6-diamidopyridine R changes conformation upon protonation of the pyridine N atom, the amide groups attached to the pyridine ring is thus rigidified upon protonation.

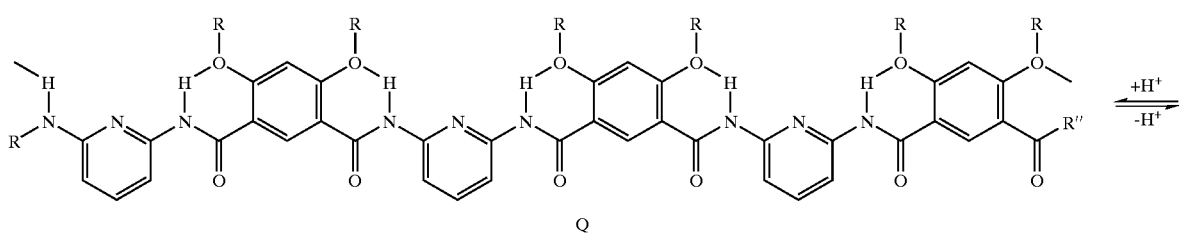

Q

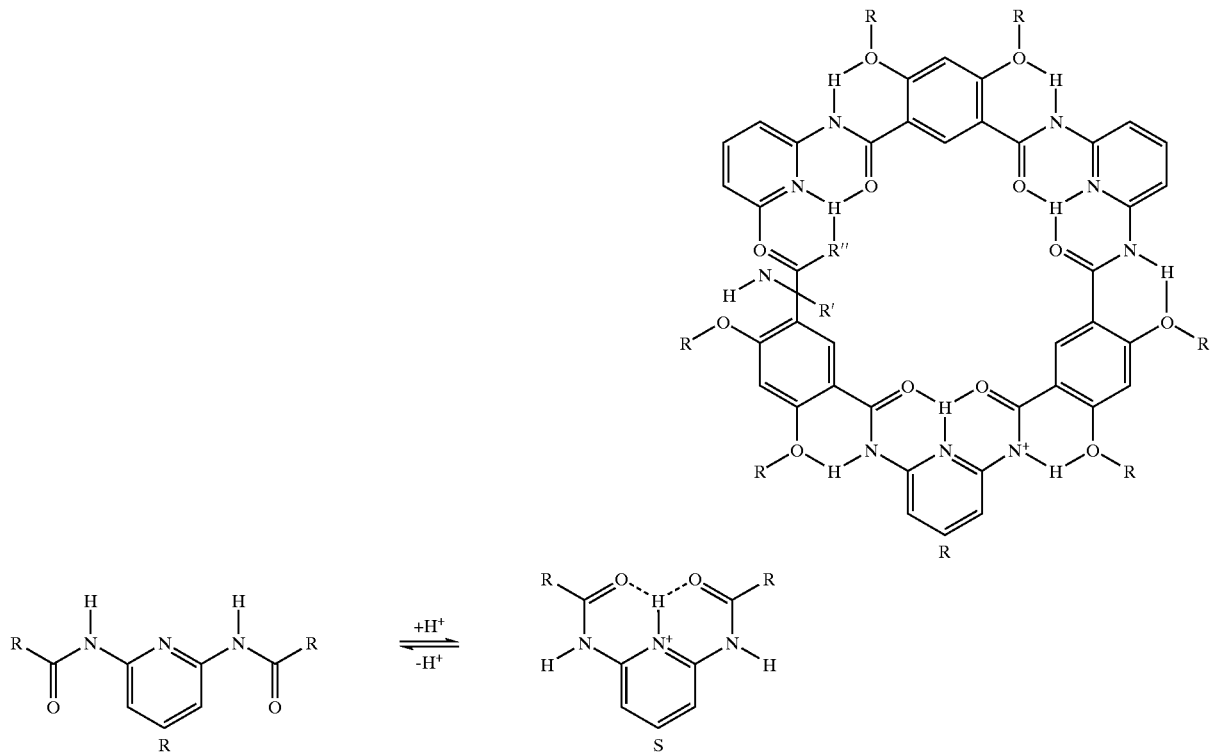

In the folded form of Q, both the H and O atoms of an amide group are involved in forming two six-membered, thus highly favorable, intramolecular H-bonded rings. An oligomer consisting of alternating 2,6-diaminopyridine and 4,6-dialkoxyisophthalic acid residues, as shown above, will show folded and "denatured" states under acidic or basic conditions, respectively. Since metal ions such as $Zn^{2+}$ and $Cu^{2+}$ can bind fairly tightly to structures Q and R, replacing the protons in Q and S with metal ions leads to metal ion-assisted folding of the oligomers. Combining 2,6-diaminopyridine and 2,3-dialkoxyterephthalic acid residues gives oligomers that show pH- and metal ion-dependent folding. The resulted helices have larger inner diameters that of Q.

D. Side Group Selection

The above-discussed helices carry side groups (the RO-groups) that point radially away from the helix axis. Due to the ability to synthesize building blocks (see below: II. Synthesis) with various RO-groups, the nature of the R groups is readily adjusted. The properties f the R groups determine the behavior of the helices in both solution and the solid-state: (1) Oligomers with short alkyl groups such as methyl and ethyl groups can be crystallized and analyzed by X-ray crystallography. (2) Oligomers carrying branched or long alkyl chains such as isobutyl, octyl or decyl groups are soluble in organic solvents such as THF and chloroformor, which facilitates their characterization in solution. Oligomers with hydrophobic side chains partition into lipid bilayers. (3) ω-Carboxyalkyl $[—(CH_2)_nCOOH]$ or ω-hydroxyalkyl $[—(CH_2)_nOH]$ groups lead to water-soluble oligomers or polymers.

E. Control of Helical Sense

The absence of chiral information in the basic building blocks leads to an equal preference for either left-or right-handed helices. If the energy barrier between the left- and right-handed helical conformations are large enough (>25 kcal/mol), then analyzing the synthesized oligomers by HPLC equipped with chiral columns can reveal the existence of a pair of enantiometers. Such an interconversion energy barrier can arise given the large energy barrier between the conformations of the monoamide (between conformation C and conformations Ca, Cb, and Cc). The helical conformation of an oligomer with a length of more than one turn is favored by two factors: (1) The combined (or cooperative) effect of the strong intramolecular hydrogen bonding interactions from each amide group, and (2) favorable aromatic stacking interactions. The cumulative effect of these two types of interactions introduces a very large interconversion energy barrier between the folded (helical) and denatured states. Such cumulative effects can be found in numerous natural systems like the assembly of DNA duplex and the folding of protein molecules. For example, the formation of double helical DNA in aqueous solution is the result of the cumulative effect of numerous rather weak non-covalent interactions. If this energy barrier is large enough (>25 kca/mol) for an oligomer, left- or right-handed helices may be resolvable by with chiral columns on HPLC using a non-polar organic solvent, by crystallization in chiral solvents or by attaching chiral side groups, which turns the racemic helices into a pair of diastereomers. Ab initio calculation can determine the relative energies of the folded and "denatured" conformations of a short (9-ring) oligomer. Including chirality in the side group R of the building blocks can also directly induce the helical sense of the oligomers and polymers during their synthesis.

However, if a pair of racemic helices can not be resolved due to low energy barrier for the interconversion of the two enantiomers, another strategy can be adopted to "fix" the chirality by covalently linking (the outer surface of a helix. For example, side chains (R groups) which bear free thiol groups form disulfide bonds upon oxidative cross-linking using $I_2$, resulting in a covalently modified outer surface.

Simple molecular modeling studies (CaChe system) show that a helix with side chains such as $HS(CH_2)_3-$ or $HS(CH_2)_4-$ can undergo such cross-linking without causing distortion to the helical backbone.

F. Synthesis of Monomers and Polymers

The same principles as discussed above are also applicable for designing helical polymers. The difference between oligomers and polymers is that the synthesis of polymers is more straightforward while at the same time, the characterization of polymers is more difficult. These polymers adopt helical conformations with tunable internal diameters, and fold upon changing environment such as pH values and solvents.

1. Building Blocks a. Derivatives of m- and p-Aminobenzoic Acids.

Figure 5A:
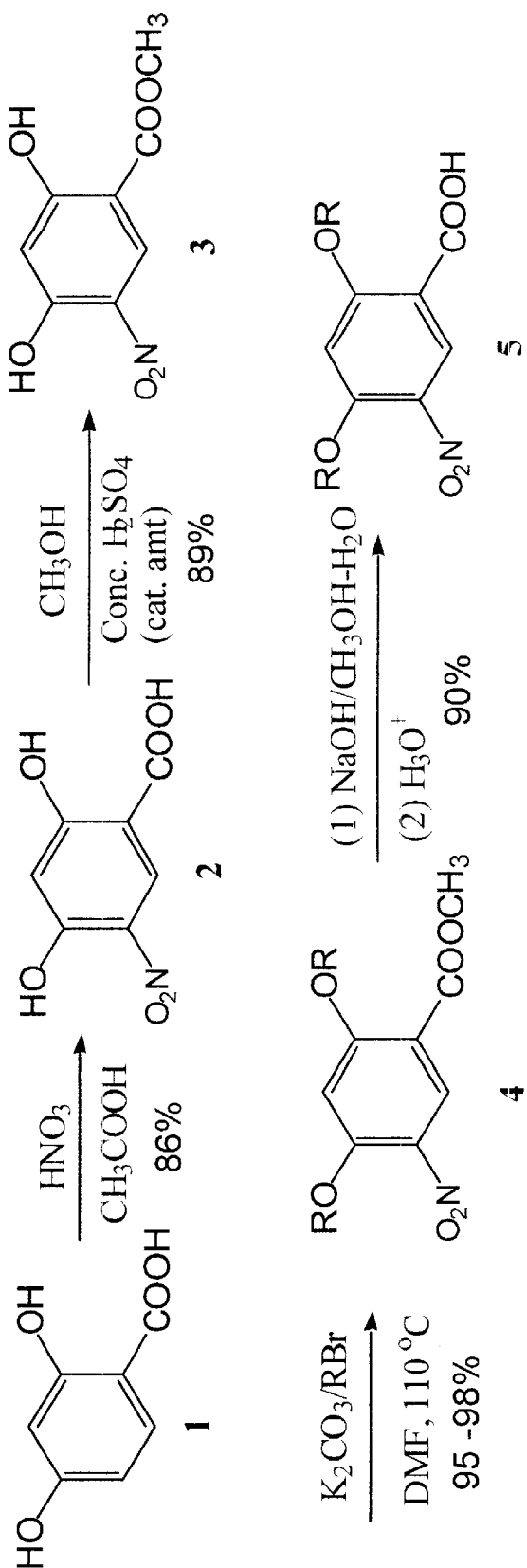
FIG. 5a is a schematic diagram showing routes of syntheses of monomers for oligomers and polymers (aromatic amino acids) using derivatives of 2,4-dihydroxy-5-nitrobenzoic acid.
Figure 5B:
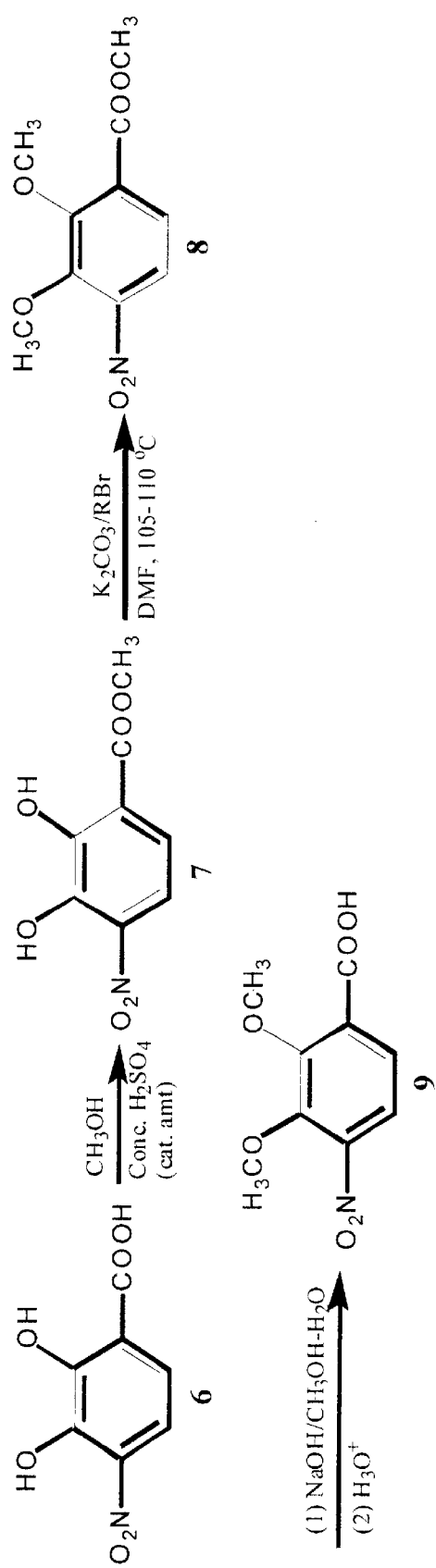
FIG. 5b is a schematic diagram showing routes of syntheses of monomers for oligomers and polymers using derivatives of 2,3-dihydroxy-4-nitrobenzoic acid.

FIGS. 5a and 5b show the synthesis of 2,4-dihyoxy-5-nitrobenzoic acid from the commercially available 2,4-dihydroxybenzoic acid. The acid is then esterified and alkylated in high yields. The alkylation reaction is quite general, since methyl, allyl, iso-butyl, octyl, and decyl bromides all have resulted in the corresponding products with high yields (>95%). Derivatives of 4-amino-2,3-dihydroxybenzoic acid are prepared from derivatives of 2,3-dihydroxyterephthalic acid whose syntheses are discussed above.

Alternative steps to the synthetic method shown in FIG. 5a include:

From 1 to 2: Other general methods for nitrating aromatic rings, such as concentrated $HNO_3$ alone, in $H_2SO_4$ at 0° C., in acetic anhydride, and $NaNO_2$ in trifluoroacetic acid, are effective for this conversion.

From 2 to 3: This esterification step can also be effected by using acidic catalysts such as HCl, tulenesulfonic acid, $BF_3$·ether and other strong acids.

From 3 to 4: This alkylation step can also be carried out with alkyl halides and alkyl iodide under the same conditions.

FIG. 5b shows: Derivatives of 2,3-dihydroxy-4-nitrobenzoic acid.

Preparation of the starting acid 6 was reported before (Kato and Morie, *J. Heterocyclic Chem.*, 1996, 33, 171; Piatak, Yim and Roosenberg, *J. Org. Chem.*, 1997, 42, 1068). The above steps are the same as the corresponding steps (including the alternative steps) in FIG. 5a.

b. Monomers for Types II, II-a and II-b Oligomers and Polymers (Diacids and Diamines).

Figure 6A:
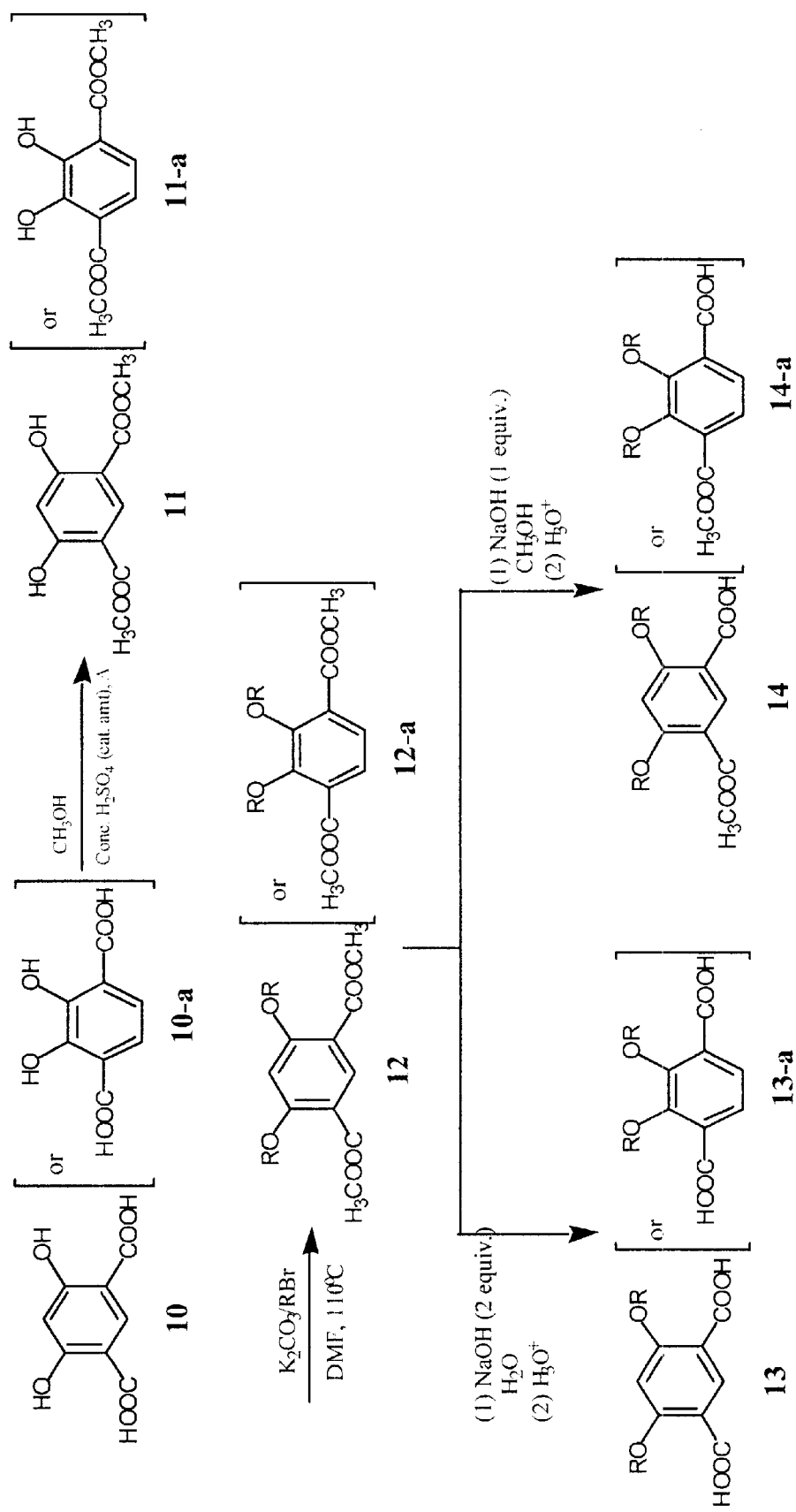
FIG. 6a is a schematic diagram showing routes of syntheses of monomers for oligomers and polymers (diacids and diamines) using derivatives of 4,6-dihydroxyisophthalic acid and 2,3-dihydroxy terephthalic acid.

FIG. 6a shows: Derivatives of 4,6-dihydroxyisophthalic acid and 2,3-dihydroxyterephthalic acid.

Alternative steps to the synthetic method shown in FIG. 6a include:

From 10 (or 10-a) to 11 (or 11-a): This esterification step can also be effected by using acidic catalysts such as HCl, tulenesulfonic acid, $BF_3$·ether and other strong acids in methanol.

From 12 (or 12-a) to 13 (or 13-a) and to 14 (or 14-a): This hydrolysis can also use other metal hydroxides such as LiOH, and KOH in water, methanol/water, or methanol/ether. An aqueous solution of a strong acid, such as that of HCl, or $H_2SO_4$, can be used to acidify the solution, such usually precipitates out the free acid.

The starting diacids, 4,6-dihydroxyisophthalic acid (10) and 2,3-dihydroxyterephthalic acid (10-a), are prepared according to known procedures: Gore, Inamdar and Nagarkar, *Ind. J. Chem.*, 1974, 12, 946 (for 10); Weitl, Raymond and Durbin, *J. Med. Chem.*, 1981, 24, 203 (for 10-a).

Figure 6B:
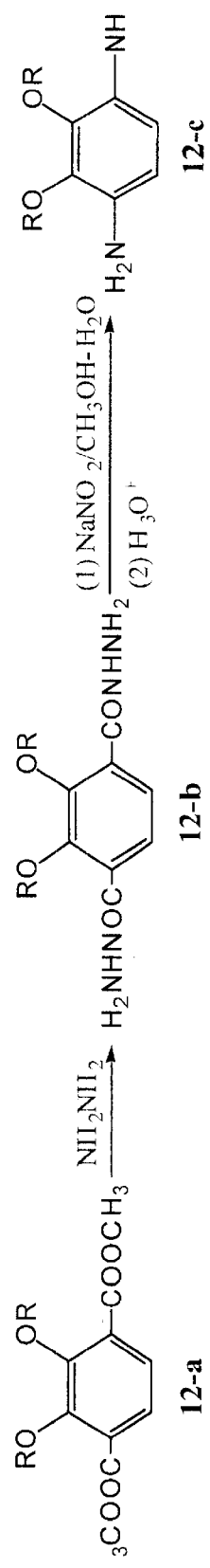
FIG. 6b is a schematic diagram showing routes of syntheses for oligomers and polymers using dialkoxydiamines.

FIG. 6b shows: Dialkoxydiamines.

2,3-Dialkoxy-1,4-phenylenediamine are prepared from the corresponding ester by Curtius rearrangement shown in FIG. 6b.

The above diamine (12-c) can also be obtained by Hofmann rearrangement of the corresponding diamide.

4,6-Dialkoxy-1,3-phenylenediamine (15) are prepared based on reported procedures as before (Hamuro, Geib and Hamilton, *J. Am. Chem. Soc.*, 1997, 119, 10587).

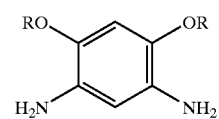

15 c. Monomers for Types III, III-a and III-b Oligomers and Polymers.

There are either discussed above (the diacids, 10 and 10-a) or are commercially available (2,6-diaminopyridine and pyridine-2,6-dicaboxylic acid).

2. Oligomers of Types II, IIc and IId

A number of oligomers have been synthesized in a stepwise (or sequence-specific) way. Two coupling methods, treating an acid chloride with an amine or forming the amide bond by EDC (1-ethyl-3-(3-dimethylaminopropyl) carbondiimide) condensation, were also satisfactory (yield >90%) for preparing the oligomers. The reaction involving an acid chloride and an amine was found to give slightly better yield.

a. Solution Phase Synthesis

Figure 7A:
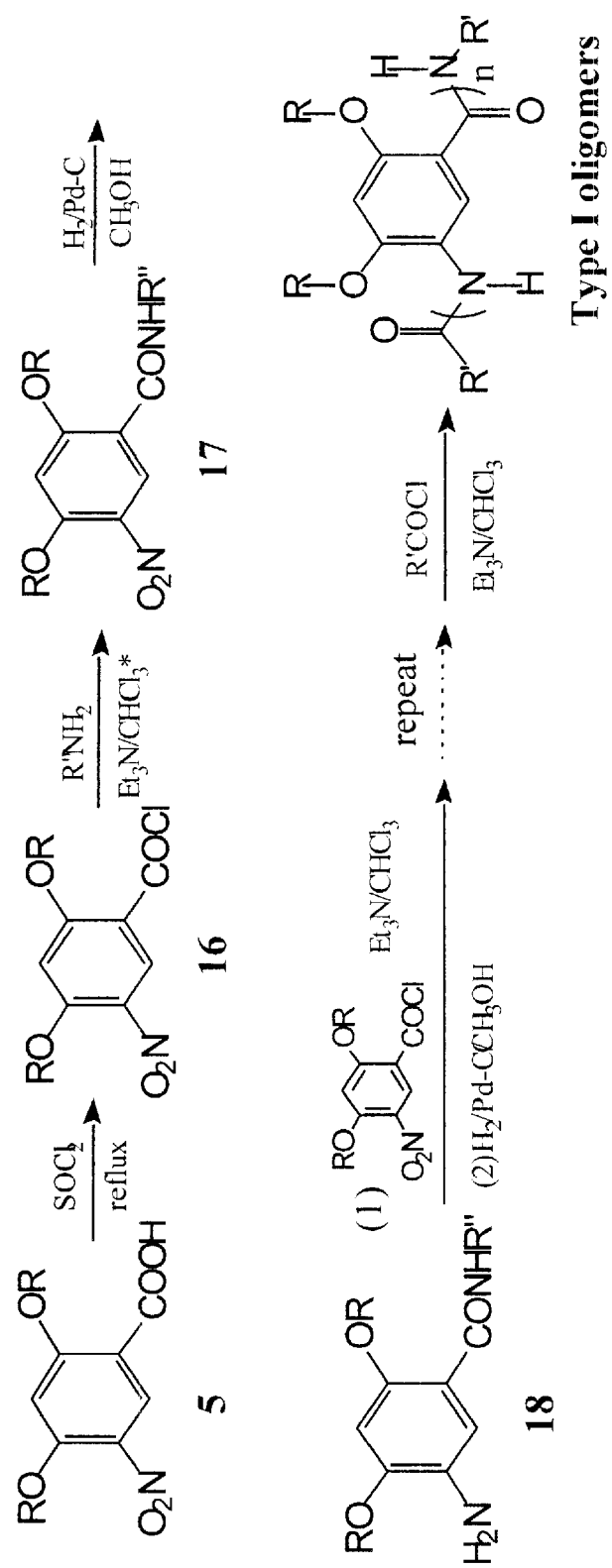
FIGS. 7a–e are schematic diagrams showing linear routes of solution phase syntheses of type IIa oligomers; (b) solution phase synthesis of type IIb oligomers; (c) a route of solid-phase synthesis for type IIa oligomers; (d) synthesis of monomers; and, (e) solid-phase synthesis of oligomers.
Figure 7B:
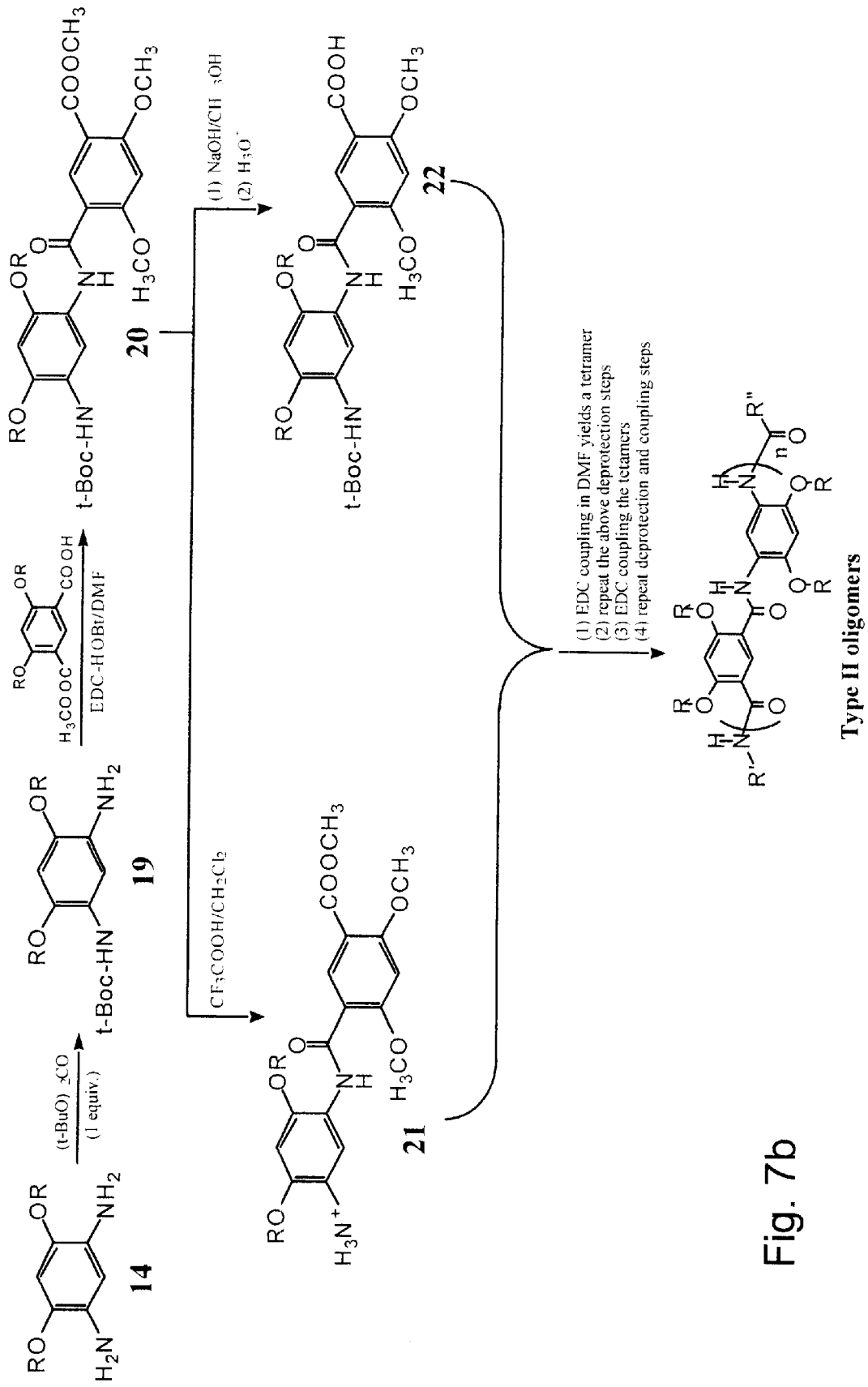

As shown in FIG. 7a, a linear synthetic route can also be adopted for type IIa oligomers. A convergent route can be used for the synthesis of type IIb oligomers, as shown in FIG. 7b.

Alternative steps to the synthetic method for type IIa oligomers shown in FIG. 7a include:

From 5 to 16: Phosphorous pentachloride ($PCl_5$) or oxalyl chloride (ClCOCOCl) can be used to replace $SOCl_2$.

Directly from 5 to 17: The acid 5 can be converted into 17 by using coupling (condensation) reagents commonly used in peptide synthesis. DCC (dicyclohexylcarbodiimide), and EDC (1-ethyl-3-(3-(dimethylamino)propyl)carbodiimide) are two most used examples of these reagents.

From 16 to 17: Other non-polar and aprotic polar organic solvents such as dichloromethane, benzene, toluene, THF, DMF etc., can also be used. Triethyl amine can be replaced by other organic or inorganic bases such as pyridine, tertiary amines, sodium and potassium carbonates and bicarbonates.

From 17 to 18: The nitro group can be reduced using a number of reduction methods such as metal (Zn, Sn, Fe) and acid, $NaBH_2S_3$, formic acid and Pd-C, etc.

From 18 to II: Type II oligomers can be prepared by repeating the steps from 17 to 18. An alternative method is coupling acid 5 and 18 (an other higher oligomer analogs) using coupling reagents commonly used in peptide synthesis.

Types II-a and II-b oligomers are prepared using the same steps as shown and discussed above by using a combination of acid 5 and 9 as the building blocks.

Alternative steps to the synthetic method for type IIb oligomers shown in FIG. 7b include:

From 19 to 20: Other coupling reagents/methods used commonly in peptide synthesis can also be used here.

From 20 to 22: This hydrolysis can also use other metal hydroxides such as LiOH, and KOH in water, methanol/water, or methanol/ether. An aqueous solution of a strong acid, such as that of HCl, or $H_2SO_4$, can be used to acidify the solution, such usually precipitates out the free acid.

Types II-a and II-b oligomers are prepared using the same steps as shown and discussed above by combining acid 5 with diamine 12-c, and acid 9 with diamine 15.

b. Solid-phase Synthesis

Figure 7C:
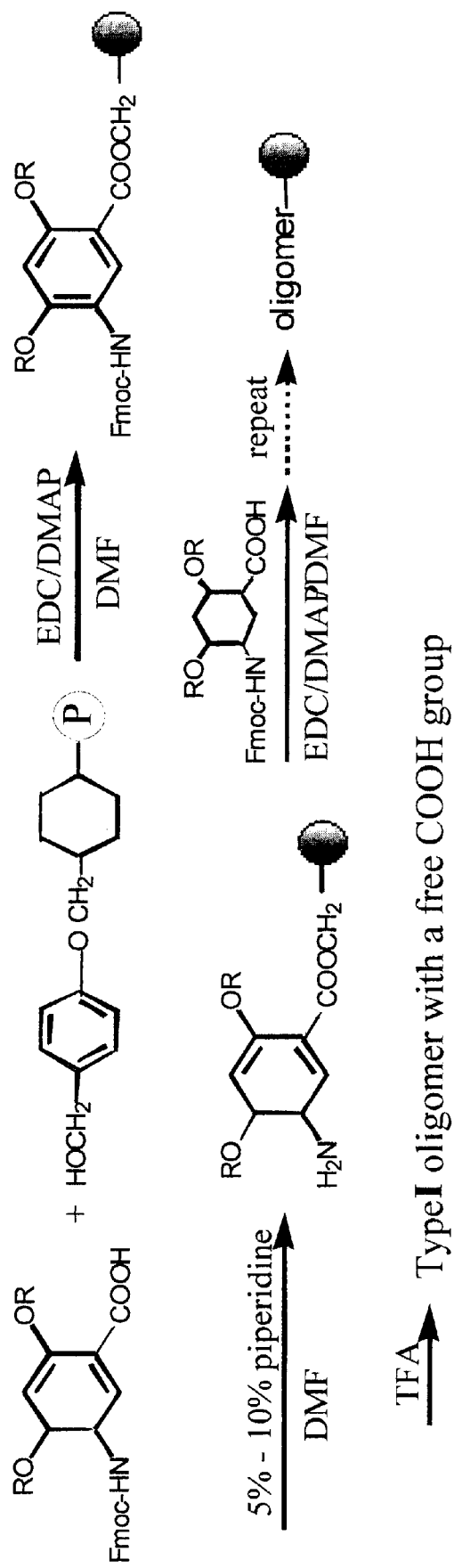

Solid-phase synthesis facilitates the preparation of long oligomers. The synthesis of type 1 oligomers, based on resins bearing an acid-labile linker such as p-benzyloxybenzyl alcohol and Fmoc-protected building blocks, is shown in FIG. 7c as an example. Synthesis of the alternating oligomers consisting of diaminobenzene or 2,6-diaminopyridine and m- or p-benzenedicarboxylic acid residues are similarly carried out by using mono protected diacid and diamine. TFA (trifluoroacetyl)-protected acid chloride may also be used, in which case similar resins as shown in FIG. 7c.

c. Synthesis of Acyl Fluoride and Fmoc-amino Group i. Monomers

Figure 7D:
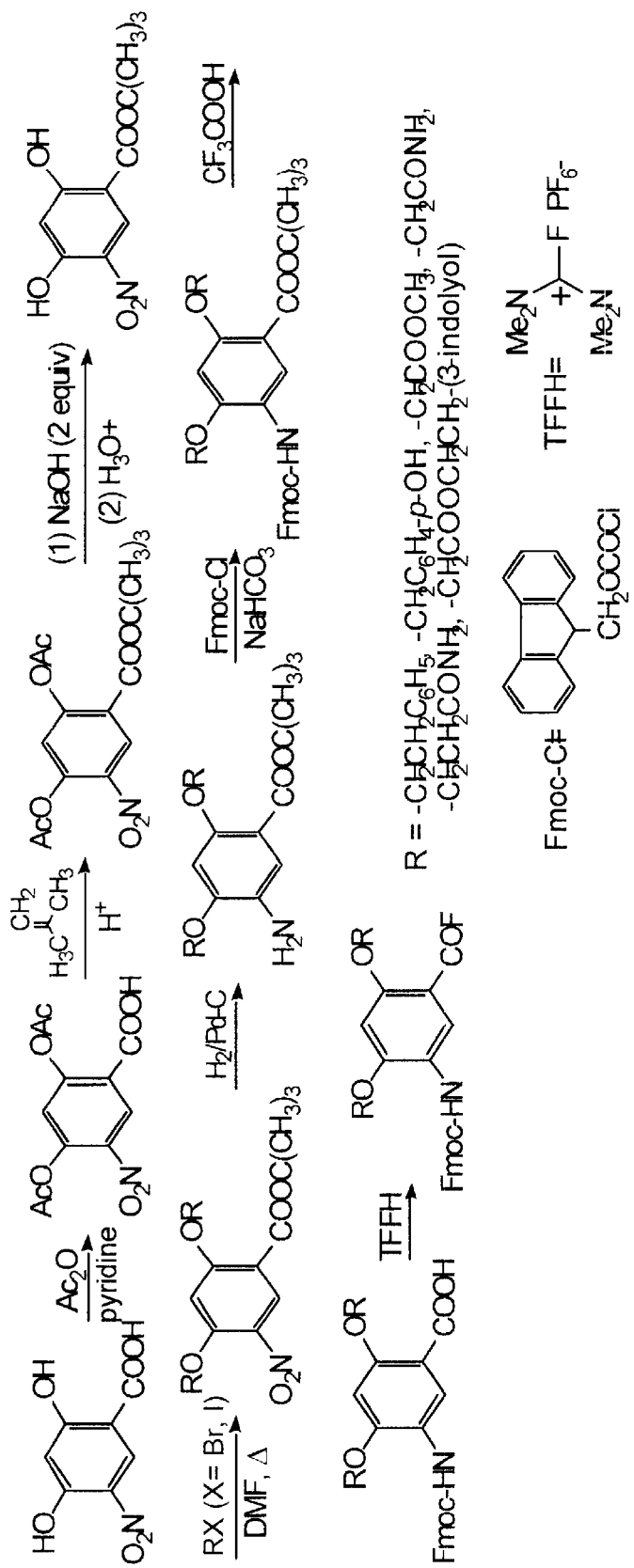
Figure 7E:
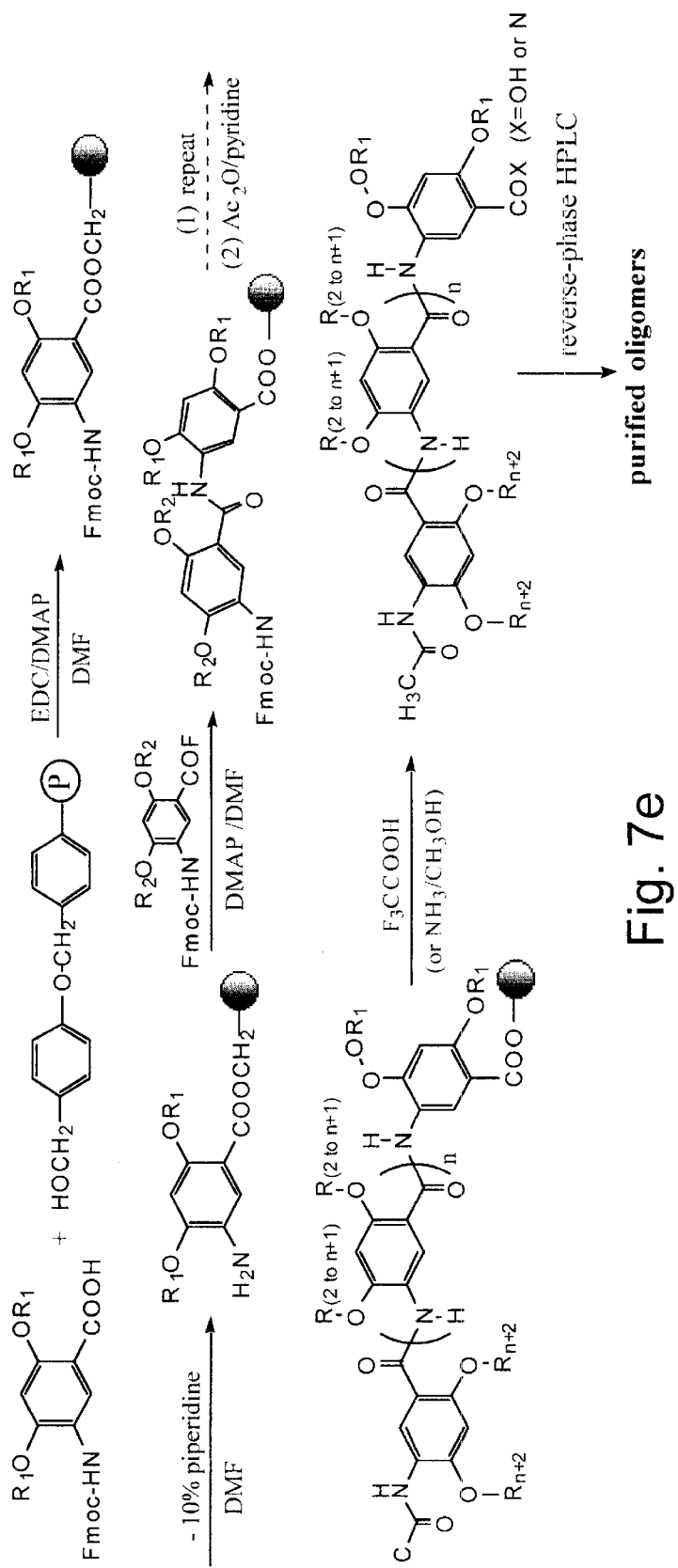

Monomers carrying acyl fluoride and Fmoc-amino groups are prepared that are compatible with conditions for the solid-phase synthesis of oligomers. These monomers also carry a variety of side chains that tailor the surface characteristics of the oligomers. Side chains that favor the partitioning of the oligomers are incorporated into the oligomers. For example, selection of side chains includes phenyl, indolyl, and primary amide groups that are found in trans-membrane peptides. A general synthetic scheme is shown in FIG. 7d.

t-Butyl ester group is introduced first because other ester groups are not compatible with later procedures for introducing the Fmoc, acyl fluoride and R groups into the monomers. Acid fluoride is chosen because of it good stability, compatibility with other functional groups (ester, amide, indolyl and the like) and high coupling yield on solid phase. An additional advantage is that the acyl fluoride group can be conveniently generated in situ using the commercially available TFFH.

d. Solid-phase Synthesis of Long Oligomers

Efficient synthesis of long (>15-mer) oligomers is achieved on solid support, which is important for the sequence-specific incorporation of monomers carrying specific side chains. In addition, combinatorial approaches are needed to assess the membrane-partioning ability and/or cytotoxicity of oligomers of various sequences. The success of such combinatorial approaches depends on efficient solid phase-synthesis. With Fmoc-amino acid fluoride, high coupling yield are achieved. However, conditions involving different monomers may vary. Coupling methods, such as EDC in DMKF and HATU in DMF, were tested on N-trifluoroacetyl-protected acids and were found to give satisfactory results with monomers bearing hydrophobic side chains.

Similar solid-phase synthesis of oligomers consisting of diacids and diamines are also within the contemplated scope of the present invention.

3. Polymers

The synthesis of polymers is, in most cases, a one-pot process and is therefore be much simpler as compared to the oligomers. The alternating co-polymers involving diacid and diamine building blocks are synthesized by treating a diamine with a diacid chloride in the presence of pyridine and an organic solvent such as chloroform, or DMF. Polymers involving aromatic amino acid building blocks are synthesized by adding the hydrochloride salt of the acid chloride or p-nitrophyenyl ester into pyridine.

a. Synthesis of Monomers for Synthesizing Polymers

Four different monomers are being employed for synthesizing polymers of different properties:

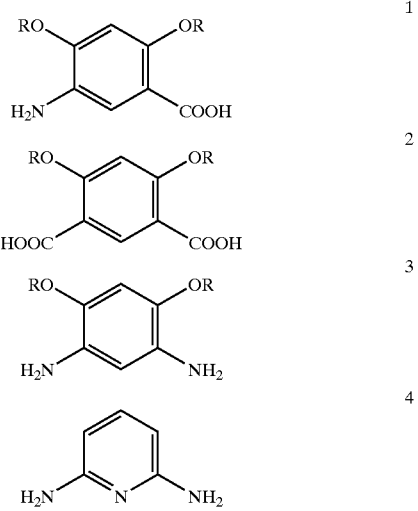

Examples of side chains include:
R=—(CH$_2$)$_7$CH$_3$, —(CH$_2$)$_9$CH$_3$, —(CH$_2$CH$_2$O)$_2$CH$_3$, —C$_6$H$_4$—p—CH=CH$_2$, —CH$_2$CH$_2$CH$_2$CH=CH$_2$, —CH$_2$CH=CH—CH=CH$_2$, (derivatives of 1 and 2 are obtained by direct alkylation of the hydroxyl groups with the corresponding bromide; derivatives of 3 are obtained from the corresponding alcohols).
R=—CH$_2$CH$_2$OH, —CH$_2$CH$_2$SH, —CH$_2$CH$_2$CH$_2$NH$_2$ (these groups lead to lateral cross-linking of the polymer chains).

Figure 8A:
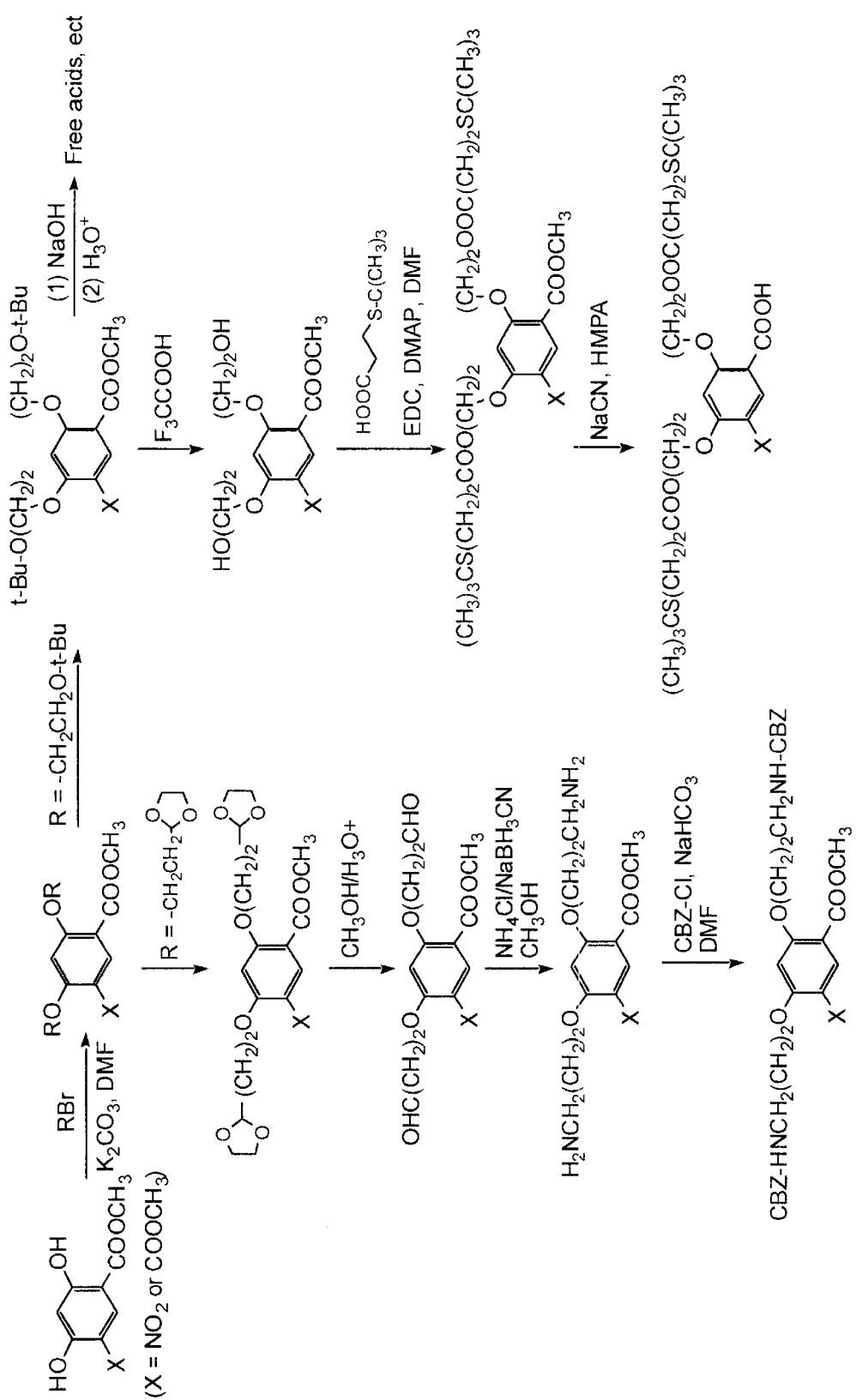

Monomers containing hydroxy, thiol and primary amino groups are synthesized as shown in FIGS. 8a and 8b.

The free OH, SH, and NH$_2$ groups are generated after the polymer chains are constructed. Only those building blocks that lead to the amide linkages on the same benzene ring being meta to each other are shown in FIGS. 8a and 8b. Those lead to para substitution are similarly constructed, which leads to adjustment of the curvature of the backbones. However, it should be understood that other building blocks are within the contemplated scope of the present invention.

b. Synthesis of Polymers

The synthesis of three different types of polymers is shown in FIGS. 8c, 8d and 8e.

Type III, III-a and IIIb oligomers can be synthesized by replacing the diamine 15 with 2,6-diaminopyridine and the monoester acid 14 with pyridine-2,6-dicarboxylic acid in the above procedures (FIG. 7a and the alternative steps) for type II, II-a and II-b oligomers.

(1) Types II, IIa and IIb: Alternative steps to the synthetic method of polymers shown in FIG. 8c include:

From 5 to 23: Other organic tertiary bases can be used to replace triethylamine.

From 25 to type II polymer: Other coupling reagents used commonly in peptide synthesis can also be used.

Types IIa and IIb polymers are prepared using the same steps as shown and discussed above by using a combination of acid 5 and 9 as the building blocks.

(2) Types II, IIb and IIc shown in FIG. 8d.

Other organic bases such as pyridine and tertiary amines can be used to replace triethylamine.

Types IIc and IId polymers are prepared using the same steps as shown above by using combining of acids 5 and 9, and the diamines 12-c and 15.

(3) Types III, III-a and III-b shown in FIG. 8e.

Type III-a polymers can be similarly synthesized by replacing 26 with the acid chloride of the diacid 13-a. Type III-b polymers can be synthesized by replacing 2,6-diaminopyridine with the diamine 12-c and 26 with the acid chloride of pyridine-2,6-dicarboxylic acid.

The resulting products fold into both right-and left-handed helices. Strategies to single handedness include: (1) attaching chiral R groups which leads to chiral amplification in the folding process, (2) denaturing (by heating) and then renaturing (by cooling) the helices in a chiral solvent, (3) denaturing and then renaturing the helices in the presence of chiral guest molecules that bind into the tubular cavities, and (4) covalently linking short oligomers of one handedness.

c. Characterization

Methods, such as x-ray crystallography and 2D NMR used for characterizing short oligomers, are not suitable for the characterizing these polymers. Instead, well-established techniques for characterizing polymers are used: (1) Gel permeation chromatography (GPC): the distribution of relative molecular weights of the synthesized polymers is determined by this method, (2) Light scattering measurements: the distribution of actual molecular weights and volumes of the synthesized polymers is determined by this method, which provides evidence for the folded on formation of the polymers. The results can also be compared to those obtained from GPC, (3) Viscosity measurements: the results provide another method of measuring relative molecular weights. In addition, folding is probed by measuring the amide NH vibrations of the polymers by IR spectroscopy, which indicates the presence of the bifurcated hydrogen bonds that must exist in the folded conformation. UV spectroscopy is used to determine the hypochromic effects of stacked benzene rings if the polymer chains are folded.

d. Formation of Polymer Films by Self-assembly and by Cross-linking

One-dimensional molecular objects, such as molecular chains, tapes, columns and cylinders, tend to self-assemble along their long axis. This phenomenon has been observed in numerous systems. The helical polymers, with long cylindrical shapes, self-assemble into bundles and films in which the tubular cavities are parallel to each other. The robustness of the bulk materials is strengthened by covalently cross-linking the polymer chains that bear side groups such as hydroxyl (forming ester and carbamate linkage), 1° amino (forming amide, urethane, and 2° amino linkage), thiol (forming disulfide linkage), vinyl and divinyl (forming C—C linkage by metathesis and by photolysis). These applications are shown schematically in FIGS. 15, 16 and 17.

G. Characterization

1. Structure Determination

The structures of synthesized building blocks, intermediates and oligomers are characterized by standard techniques such $^1$H- and $^{13}$C-NMR, mass spectrometry and elemental analysis. The solid-state structures of these oligomers are determined by X-ray crystallography. The crystal structures provide detailed and conclusive three-dimensional structural information, including bond lengths, bond angles and the proposed folding patterns, which guides further the design and structural modification of the oligomers.

2. Folding Studies

Except for direct structural determination by X-ray crystallography, the folding of the oligomers and polymers in various solvents are characterized by ultraviolet (UV) spectroscopy, proton nuclear magnetic resonance ($^1$H-NMR) and high performance liquid chromatography (HPLC) at different temperatures and in various solvents.

a. UV Spectroscopy

Hypochromic effect is observed by UV as the reduction in optical absorption density, which is a powerful indicator of the oriented chromophores commonly seen in DNA, RNA, and other polymers. Based on UV hypochromic effects, Moore et al., supra, reported the characterization of folded phenylacetylene oligomers whose backbones consist of benzene rings and acetylene linkers. Hypochromic effects are sensitive to the distance r (varying as $r^{-3}$) between chromophores and their relative orientations. In the absence of any folded conformation, the molar extinction coefficient $\epsilon$ is linearly dependent on oligomer length, since the effective concentration of chromophores are increases linearly with chain size. In the helix, however, monomer chromophores are aligned in a fashion that diminishes the overall absorption, and $\epsilon$ falls below the linear extrapolation based on shorter chains that can not form helices. As a result, the chain length dependence of $\epsilon$ may change abruptly when the number of monomers in the chain reaches a stage that allows the helices to form. A new slope that is similar than that for the shorter oligomers can be observed. The shape of the UV spectra of the oligomers and polymers can also be sensitive to chain length. The shorter oligomers that are incapable of forming helices show similar absorption peaks as those of the monomer chromophores. The UV spectra of longer oligomers that fold into helices show significant changes when compared to those of the monomers and the shorter analogs.

b. NMR

Additional evidence for the formation of helices can be provided by following the chemical shifts $\delta$ of the aromatic and amide $^1$H-HMR signals. The chemical shifts of protons within 7 Å of an aromatic ring experience an upfield shift to smaller $\delta$ when located above the ring. Thus, for oligomers that fold into helices, upfield shifts in the aromatic and amide proton resonances are observed, consistent with parallel stacking of aromatic rings.

In addition to the information obtained from chemical shifts changes, two-dimensional (2D) NMR are also be used to further determine the conformation of short oligomers in solution. Techniques such as DQCOSY (double quantum filtered correlation spectroscopy) and TROESY (transverse rotating-frame Overhauser effect spectroscopy) that have been used successfully to determine the secondary structures of peptides, oligonucleotides and unnatural folding oligomers are employed. Interproton distance bonds are determined by using unambiguously assigned ROE (rotating-frame Overhauser effect) cross peaks, which leads to refined structures. Both the curved backbone and helical conformations are determined this way. To avoid extensive signal overlap, various side chain groups (—OR) are sequence-specifically introduced into an oligomer to increase chemical shift dispersion. Given the ease of monomer preparation, monomers with side groups whose signals separate clearly in 1D spectra are synthesized. Examples of these-OR groups are shown below.

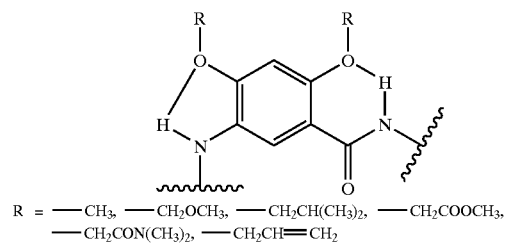

R = —CH$_3$, —CH$_2$OCH$_3$, —CH$_2$CH(CH$_3$)$_2$, —CH$_2$COOCH$_3$, —CH$_2$CON(CH$_3$)$_2$, —CH$_2$CH=CH$_2$ c. HPLC

As mentioned above, helices from a chiral basic building blocks contain an equal amount of left- and right-handed helices. Such a racemic mixture is analyzed by HPLC using commercially available chiral columns under non-denaturing conditions. If two peaks of nearly equal intensity are observed, the formation of the helices is then clearly indicated. If chiral HPLC columns fail to resolve synthesized helices, covalent cross-linking of the outer surface, which "freezes" the left- or right-handedness of a helix, is attempted before using PHLC characterization.

d. Differential Scanning Calorimetry

Differential scanning calorimetry (DSM) is utilized to study the stability of the helices. DSC is commonly used to study the thermal stability and melting temperature (Tm) of proteins. Tm is defined as the midpoint in the narrow temperature range between the native folded state and the unfolded state of a protein. Calorimetry has been the most effective tool available to determine the Tm of proteins and this technique is used to examine the thermal transition of the helical oligomers. Thermal unfolding is accompanied by absorption of heat as the secondary structure is melted. A narrow peak in excess heat capacity serves as further evidence of a highly cooperative nature of oligomer unfolding. Integration of the melting peak provides the enthalpy of melting ($\Delta H_m$). The $\Delta H_m$ provides insight into the energetic impact of environmental changes on the folded state of these oligomers.

e. Effects of Solvents and Temperature

The effects of solvents and temperature on the helical conformation is examined using UV and NMR. Oligomers with side chains such as the triglyme monomethyl ether group that are compatible with a variety of different solvents are synthesized for such studies. Although the helices, once formed, are robust due to the existence of two stabilizing factors that act cooperatively, highly polar solvents, such as DMSO, methanol and water at elevated temperature, still disrupt the intramolecular H-bonds and thus may denature the helical conformation. However, the stacking of aromatic rings becomes more stable in polar solvents.

3. Biological Inertness

The folded conformation is quite resistant toward proteases and other hydrolytic enzymes. The stability of the oligomers is tested using commercially available proteases such as chymotrypsin and trypsin and mouse serum. The hydrolysis is monitored by reverse phase HPLC. The folded helices are believed to be non-immunogenic, similar to peptoid, since if they can not be hydrolyzed by proteases, they can not be presented by MHC molecules in the relevant antigen presenting cells.

H. Modification and Assembly

The advantage of this new class of helical compositions lies in the fact that they are readily adjustable: the inner diameters of their tubular cavities can be adjusted and their outer surfaces can be modified by attaching different side groups.

1. Synthetic Nanotubes with Tunable Properties and Enhanced Stability

The helices are open ended nanotubes with well-defined tubular cavities. For oligomers, the length of the nanotubes can be defined by the chain size, which compares favorably with previously described peptide or carbone (50) nanotubes. (Ghadiri, M. R.; Granja, J. R.; Milligan, R. A.; McRee, D. E.; Khazanovich, N. (1993) Self-assembling organic nanotubes based on a cyclic peptide architecture. Nature 366; 324; Kim, H. S.; Hartgerink, J. D.; Ghadiri, M. R. (1998) Oriented self-assembly of cyclic peptide nanotubes in lipid membranes. *J. Am. Chem. Soc.* 120, 441; Fan, S.; Chapline, M. G.; Franklin, N. R.; Tombler, T. W.; Cassell, A. M.; Dai, H. (1999) Self-oriented regular arrays of carbon nanotubes and their field emission properties, Science 282, 512). Unlike the self-assembling peptide nanotubes whose length can not be defined, the length of these helices are tuned synthetically by adjusting the chain size of the oligomers. This type of tunability is a feature that is not seen in any other known nanotubes.

Although these nanotubes are believed to be quite stable, their robustness may still not be comparable to that of the covalently linked carbon nanotubes. By introducing side chains with terminal groups such as thiol, hydroxyl or amino groups, the outer surface of the nanotubes can be covalently crosslinked. The modification is accomplished by using techniques that are well-established in biochemistry, such as oxidative formation of disulfide bonds, reaction of the hydroxyl or amine groups with dicarboxylic acid chloride or diisocyanate. The modified helices are also believed to have significantly enhanced stability. The covalent modification of the outside surface also provides an effective method for locking the conformations of the helices, which can then be resolved into left- or right-handed helices by using chiral reagents or chiral HPLC columns.

2. Self-Assembling Nanotubular Structures

Figure 9:
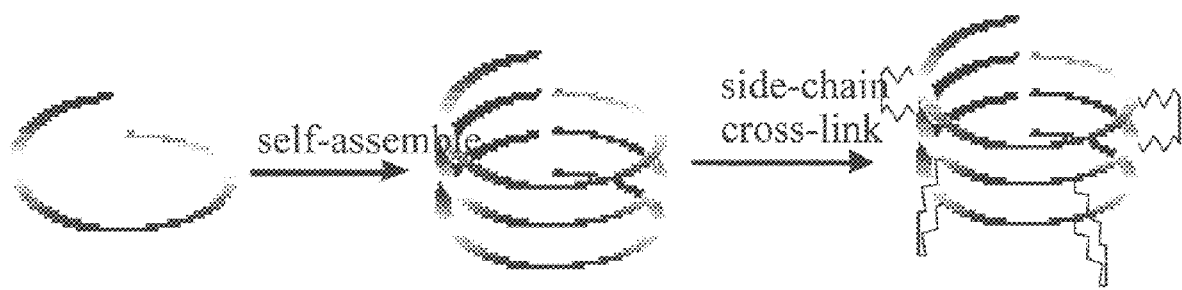
FIG. 9 is a schematic diagram showing that long nanotubes maybe formed by the self-assembly of short (7–9 residues) oligomers. The major driving force for this assembling process is the aromatic stacking interactions between the backbone benzene rings. Covalent cross-linking (for example, by forming disulfide bonds) of the side groups leads to tubular polymers with segmented helical backbone but covalently modified outside surface.

Oligomers with lengths equal to or slightly longer than one spiral turn (7–9 residues) are a novel class of nanoscale building blocks for the formation of long nanotubes through self-assembly, as shown in FIG. 9. The assembly process is similar to that of helicenes, which is driven by aromatic stacking interactions. The resulted structures are also similar to those of the reported cyclic peptides that self-assemblies into hydrogen-bonded nanotubes. An additional factor that facilitates the self-assembly process is the two self-complementary (screw-shaped) ends of either left- or right-handed helices, again similar to the self-assembly of helicenes. Long alkyl side chains such as decyl or dodecyl groups, combined with the large aromatic contact surfaces at the two ends of these oligomers, strongly favor the assembling process in a hydrocarbon solvent such as dodecane. Similar to the covalent modification discussed above for the oligomers, the outside surface of the self-assembled polymeric tubes can also be covalently modified by introducing side groups that can be cross-linked. As a result, tubular polymers with segmented helical backbone but covalently modified outside surface are obtained. Compared to cyclic peptides or helicenes, these short (6–8 residues for type 1) oligomers are much more readily available synthetically and their structural modifications are also much more convenient.

The self-assembled nanotubes are characterized by similar techniques used for the previously reported helicene aggregates and peptide nanotubes. (Nuckolls, C.; Katz, T. J.; Castellanos, L. (1996) Aggregation of conjugated helical molecules. J. Am. Chem. Soc. 118, 3767; Nuckolls, C.; Katz, T. J.; Katz, G.; Collings, P. J.; Castellanos, L. (1999) Synthesis and aggregation of a conjugated helical molecule. J. Am. Chem. Soc. 121, 79–88; Ghadiri, M. R.; Granja, J. R.; Milligan, R. A.; McRee, D. E.; Khazanovich, N. (1993) Self-assembling organic nanotubes based on a cyclic peptide architecture. Nature 366:324; Kim, H. S.; Hartgerink, J. D.; Ghadiri, M. R. (1998) Oriented self-assembly of cyclic peptide nanotubes in lipid membranes. J. Am. Chem. Soc. 120, 4417). These techniques include: (1) X-ray crystallography which is the most suitable technique since it can provide detailed and conclusive three-dimensional structural information on these large self-assembled nanotubular structures; these technique, however, is limited by the availability of X-ray diffraction quality crystals; (2) cryoelectron microscopy. (Milligan, R. A.; Flicker, P. F. (1987) J. Cell Biol. 105, 29). When self-assembled nanotubes are formed, as FIG. 4 shows, cryoelectron micrographs of frozen hydrated nanotube microcrystals at high magnifications reveal striations along the long axis of the crystals. When the observed striations are spaced at a distance that is close to the van der Waals width (or diameter) of a single helix, then these striations represent images of individual self-assembled nanotubes packed side-by-side in parallel; (3) UV-vis absorption spectra. By comparing the UV-vis absorption spectra of an oligomer at both low (~0.001 mM to 0.1 mM) and high (>10 mM) concentrations in a hydrocarbon solvent such as dodecane, formation of aggregates are revealed by red-shifted absorptions as the concentration is increased. In the presence of a solvent such as chloroform which is known to disfavor the formation of aggregates, the UV-vis absorption spectra of an oligomer at high (>10 mM) concentration change to those attributed to the unassociated molecules (4) $^1$H-NMR. (Palmans, A. R. A.; Vekemans, J. A. J. M.; Havinga, E. E.; Meijer, E. W. (1997) Angew. Chem. Int. Ed. Engl. 36, 2648). Comparing the concentration-dependent change of the chemical shifts of the aromatic region of a short oligomer reveals the formation of the self-assembled aggregates, as shown in FIG. 9. An upfield shift of the aromatic $^1$H-NMR resonances is consistent with parallel stacking of aromatic subunits.

I. Uses and Applications

The above-described helices have at least two novel structural characteristics: (1) the adjustable tubular cavities. The inner wall of a tube is decorated with the amide-O atoms, which makes the tubular cavities electrostatically negative and quite hydrophilic. These nanoscale cavities are useful to transport a variety of metal ions and small molecules. (2) The readily modifiable outer surfaces. The surfaces tolerate a broad range of side group alterations. Tailoring the surface characteristics of the helices extends their utility to a variety of biological and materials science applications in which the physical properties of the media are of paramount importance. The design schemes of the helices produce binding surfaces with the high information content necessary for the type of molecular recognition for forming or interacting with sophisticated architectures.

1. Non-Selective Channels and Pore-Forming Toxins

The helices are nanotubes with hydrophilic tubular cavities of large inner diameters (10 Å to 30 Å). The helices display good ion- and small molecule-transport activity. The helices partition into cell membrane as artificial pore-forming agents, which can act as antibiotics and anti-cancer drugs by piercing the cell membrane.

a. Choice of Side Chains

While side chains such as iso-butyl, octyl, or decyl groups help the stable integration of a helix in the non-polar environment of lipid bilayers, oligomers bearing only hydrocarbon side chains tend to aggregate in an aqueous environment and become highly insoluble. Previous studies on both natural and synthetic pore-forming peptides had indicated that the indole side chain of tryptophan is important for imparting solubility in polar organic solvents such as dimethyl sulfoxide (DMSO) and dimthylformamide (DMF), yet is sufficiently hydrophobic to allow efficient partitioning of tryptophan-rich peptides into apolar membrance environments. (Hu, W.; Lazo, N. D.; Cross, T. A. (1995) Biochemistry 34, 14138; Hu, W.; Cross, T. A. (1995) Biochemistry 34, 14147; Ghadiri, M. R.; Granja, J. R.; Milligan, R. A.; McRee, D. E.; Khazanovich, N. (1993) Self-assembling organic nanotubes based on a cyclic peptide architecture. Nature 366:324; Kim, H. S.; Hartgerink, J. D.; Ghardiri, M. R. (1998) Oriented Self-assembly of cyclic peptide nanotubes in lipid membranes. J. Am. Chem. Soc. 120, 4417). The indole side chains had also been implicated in natural peptides and proteins as being important for anchoring polypeptide chains to lipid bilayers through interaction of side chain NH groups with the hydrophilic water-membrane interface. Indoleethanol is incorporated into the candidate channel forming oligomer T, which contains indole side chains on every third residue. The indole side chains are incorporated through ester exchange reaction after the oligomer backbone is constructed. Other combinations of side chains can be similarly designed.

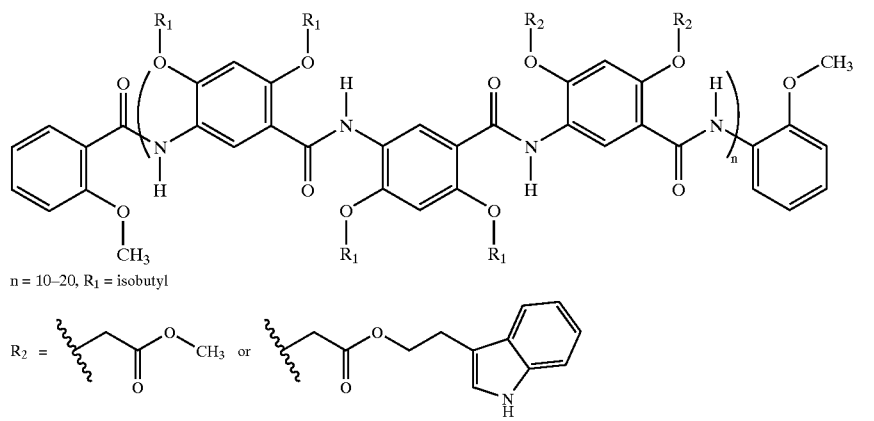

b. Assessments of Cation Transport (i) Liposome-based Assays: Proton Transport Activity The bulk proton transport activity is screened using a liposome-based assay. (Carmicheal, V. E.; Dutton, P. J.; Fyles, T. M.; James, T. D.; Swan, J. A.; Zojaji, M. (1989), J. Am. Chem. Soc. 111, 769). Specifically, large unilamelar vesicles (LUVs) prepared by the reverse-phase evaporation method at pH 6.5 are diluted into pH 5.5 buffer. (Szoka, F.; Papahadjopoulos, D. (1980) Comparative properties and methods of preparation of lipid vesicles (liposomes). Annu. Rev. Biophys. Bioeng. 9, 476). Collapse of the resulting transmembrane proton gradient upon addition of the helix solution (typically 1 mM in DMSO) is followed by monitoring the fluorescence of an entrapped pH sensitive dye (for example: 5(6)-carboxyfluorescein from Molecular Probes). Control experiments as described before are carried out to ensure that collapse of the pH gradient upon addition of the helices is caused neither by rupture of liposomes nor by the presence of small amounts of the organic solvent (~5% DMSO). (Driessen, A. J. M.; van den Hooven, H. W.; Kuiper, W.; van de Kamp, M.; Sahl, H. G.; Konings, R. N. H.; Konings, W. N. (1995) Biochemistry 34, 1606). When the proton transport activities of the helices are similar to those of the natural ion channel formers, such as gramicidin A and amphotericin B, then these helices act as ion channels.

(ii) Single Channel Conductance Measurements

This method involves the use of micro patch clamp techniques and is a critical test for establishing and quantifying the transport efficiency of a membrane channel structure. (Corey, D. P. (1983) Patch clamp: Current excitement in membrane physiology. Neuroscience Commentaries 1, 99). Observing a high throughput rate demonstrates ion channel formation, and is a diagnostic feature distinguishing ionic channel mechanism from other ion transport devices such as ion carriers. (Hill, B. (1992) Ionic Channels of Excitable Membranes 2nd Edn. Sinauer Associates, Sunderland). Planar lipid bilayers are formed on micropipet electrodes using Type II-S soybean phosphatidylcholine (from Sigma), a 5 $\mu$L aliquot of helix solution (1 mM in DMSO) is added to 150 $\mu$L subphase buffer, resulting in spontaneous partitioning of helix into the lipid bilayer. Data acquisition and analysis are performed using the Clamp software package (Axon Instruments).

c. Small Molecule Transport

The transport of small hydrophilic molecules across cell membranes represents an essential metabolic process in eukaryotic organisms. Artificial transmembrane channels which mediate the transport of biologically relevant molecules across lipid bilayers are important applications as drug-delivery systems.

With their large internal diameters, these helices also act as channels for transporting small molecules such as glucose. Using the similar approach as described above for characterizing ion channels, glucose transport activity is analyzed in isotonic solutions using glucose entrapped LUVs. (Granja, J. R.; Ghadiri, M. R. (1994) Channel-mediated transport of glucose across lipid bilayers. J. Am. Chem. Soc. 116, 10785). The glucose transport activity is monitored spectrophotometrically at 340 nm for the production of NADPH using an enzyme-coupled assay. (Kinsky, S. C. (1974) In Methods in Eznymology; Fleischer, S., Packer, L., Eds. Academic Press: London, 1974, Vol. 32, pp. 501–503). The kinetics of glucose-entrapped liposomes is thus established. Control experiments, in the absence of any channel-forming reagents, or in the presence of well-known channel-forming peptide, such as gramicidin A, which can not transport any glucose molecule due to a small internal diameter (~4.5 Å) are also performed to ensure the observed glucose (or other small molecule) transport activity by the helix is due to the formation of large channels.

d. Assessment of Helix Orientation within the Membrane

To function as transmembrane channels with discrete, bilayer-spanning pores, the helices must orient in such a way that their central axis is approximately perpendicular to the plane of the lipid membrance. The orientation of the membrane-penetrating helices is investigated using previously described biophysical methods. (Kim, H. S.; Hartgerink, D.; Ghardiri, M. R. (1998) Oriented self-assembly of cyclic peptide nanotubes in lipid membranes. J. Am. Chem. Soc. 120, 4417). These include polarized attenuation total reflectance (ATR), grazing angle reflection-absorption, and transmission Fourier transform infrared (FT-IR) spectroscopy methods. The detailed experimental procedures for the characterization of cyclic peptide nanotubes is similarly applied for investigating the orientation of the helices in lipid membrane.

e. Cytotoxicity

The above designed helices, when confirmed as pore-forming reagents, act as a novel class of cytotoxic agents that cause lysis of cells by piecing the cell membrane. The cytoxicity of the pore-forming helices is investigated in vitro by assaying their inhibitory effects on the proliferation of cultured tumor cells, such as murine leukemia (L1210) and murine mammary carcinoma (FM3A) cells.

f. Tumor-specific Toxins

It was reported that the non-specific toxicity of the cytolytic peptide, melittin, was overcome when the peptide was linked to a tumor-antigen specific antibody. (Dunn, R. D.; Weston, K. M.; Longhurst, T. J.; Lilley, G. G.; Rivett, D. E.; Hudson, P. J.; Raison, R. L. (1996) Antigen binding and cytotoxic properties of a recombinant immunotoxin incorporating the lytic peptide, melittin. Immunotechnology 2(3), 229). The non-selective pore-forming helices also become selective therapeutic reagents when coupled to tumor specific antibodies. Numerous tumor-specific antibodies have been described in the literature. (Panchal, R. G. (1998) Novel therapeutic strategies to selectively kill cancer cells. Biochem. Pharmacol. 55(3), 247; Chen, W. T. (1996) Proteases associated with invaldopodia, and their role in degradation of extracellular matrix. Enzyme Protein 49(1–3) :59). The Fab fragments of tumor-specific antibodies, which are generated by papain digestion, are linked to the cytotoxic reagents via disulfide bonds. (Goetzl, E. J.; Metzger, H. (1970) Biochemistry 9, 1267). The free thiol group on Fab is generated by reduction with mercaptoethanol.

Figure 10:
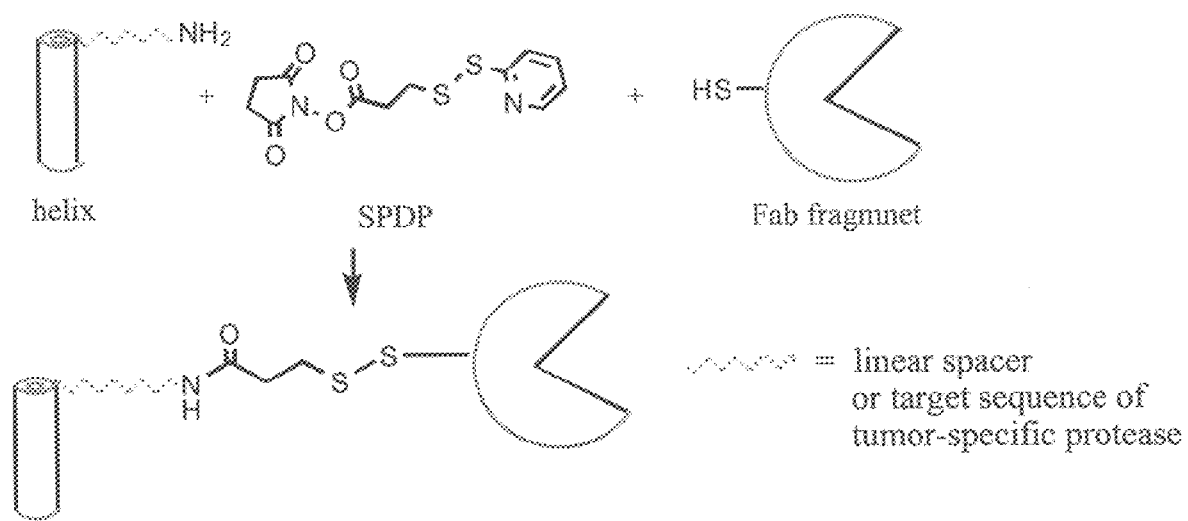
FIG. 10 is a schematic diagram showing a route of synthesis of tumor-specific toxins.

Specifically, a pore forming helix bearing a free amino group is linked to Fab fragments with the heterofunctional cross-linking agent SPDP [N-succinimidyl-3-(2-pyridyldithio)propionate, from Pharmacial, as shown in FIG. 10.

While a potential problem could be that the large Fab fragment may interfere with pore formation, this problem can be addressed by two strategies: (1) Using a flexible linker (between the helix and the free amino group) that is long enough so that the interference of the Fab fragment can be minimized; and (2) incorporating the recognition site (target sequence) of a tumor-specific protease as part of the spacer in the helix-Fab conjugate, which will ensure that the pore-forming helix is released upon arrival at the site of the tumor cells.

One such protease is cathepsin B, which is secreted by certain metastatic tumor cells. (Sloane, B. F.; Dunn, J. R.; Honn, K. V. (1981) Lysosomal cathespin B; correlation with metastatic potential, Science 212, 1151).

2. Selective Channels and Pores with Controlled Properties

While the pore formed by a helix is believed to be a passive channel which is open under normal circumstances, it is possible to convert the helices into channels with the ability to open and close. Various molecular switches can be put into the helices. The molecular switches might be biochemical (activated by enzymes), chemical (activated by the binding of small molecules and ions), or by physical stimuli, such as heat or light.

Figure 11:
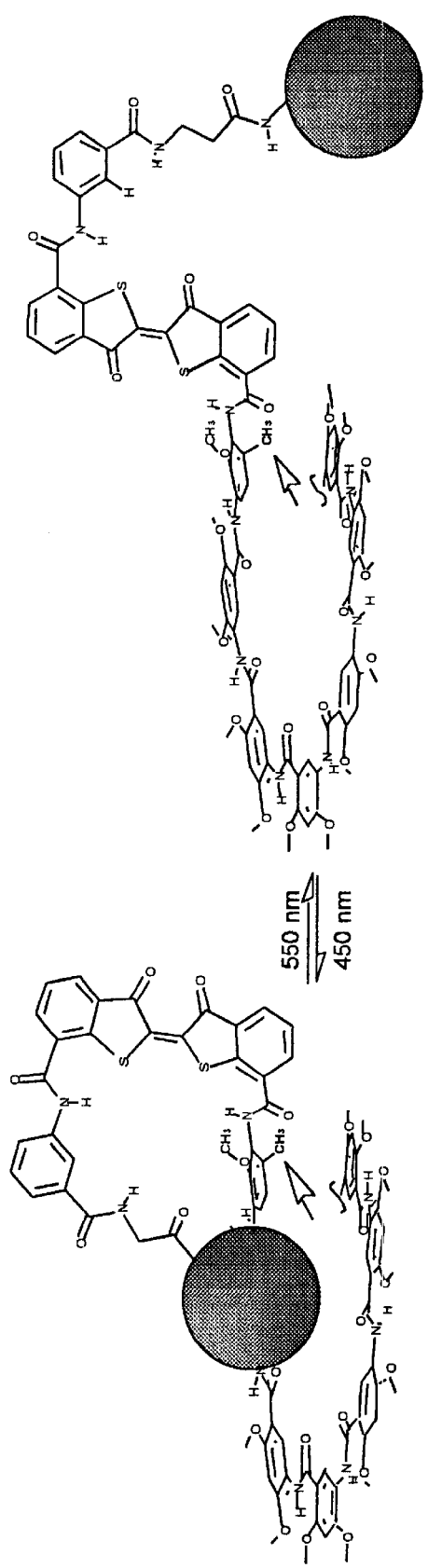
FIG. 11 is a schematic diagram that shows a model for channels with a photoresponsive switch. The trans-cis photoisomerizable chromophobe of thioindigo acts as the a switch that can either open or close the channels depending on the wavelength of their radiation. About 1 turn of a helix is shown here for clarity of view. Hydrogen atoms, except for those of the amide groups, are omitted for clarity of view. The methyl group (indicated by arrow) keeps the switch in the desired (vertical) conformation.

FIG. 11 shows a model of a helix with a photoresponsive switch. It is known that thioindigo predictably undergoes cis-trans isomerization upon irradiating by light source with wavelength of 550 nm (cis to trans) or 450 nm (trans to cis). Such a property of thioindigo has been successfully exploited for the photomodulation of metal ion binding by polyethers. (Irie, M.; Kato, M. (1985) Photoresponsive molecular tweezers. Photoregulated ion capture and release using thioindigo derivatives having ethylenedioxy side groups. J. Am. Chem. Soc. 107, 1024). By incorporating the thioindigo unit into either end of a channel-forming helix, the channel is opened or closed by applying irradiation of two difference wavelengths.

Figure 12:
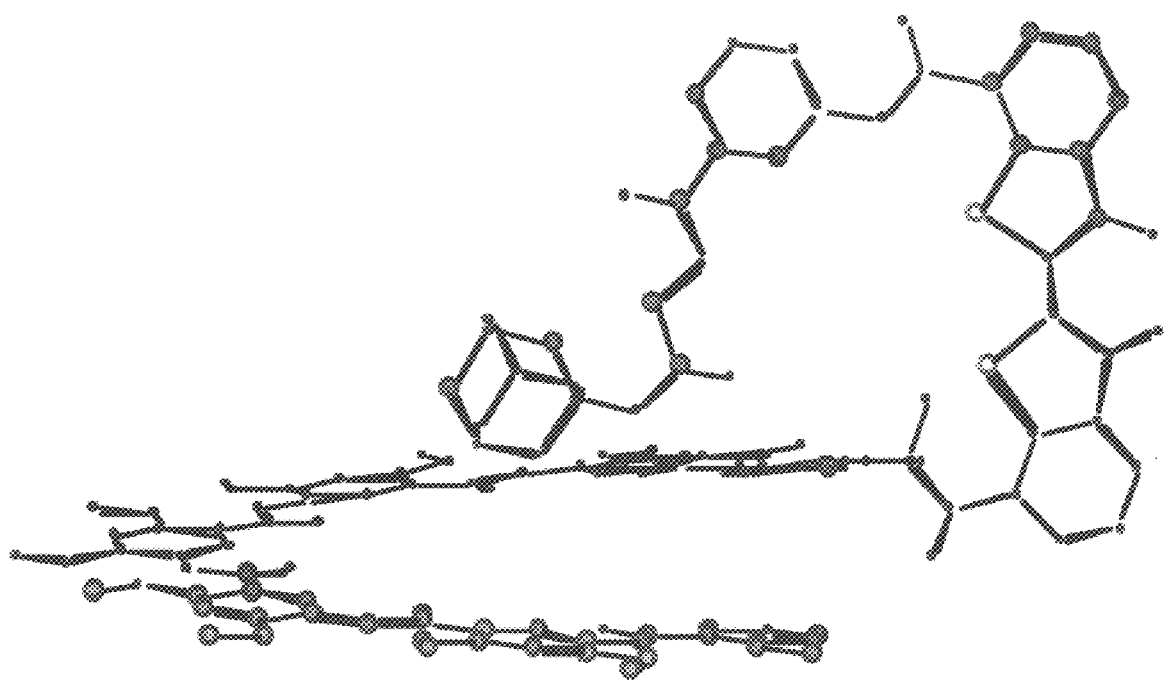
FIG. 12 shows a Chem3D model of a helix with a photoresponsive switch. When the indigo unit is in the cis configuration, the bulky adamantane group blocks the entrance of the helix. When the indigo unit adopts a trans configuration, the channel is opened. Only ~1 turn of a helix is shown here for clarity.

FIG. 12 is a model in which the bulky adamantine group sits right above the mouth of a helix.

Figure 13:
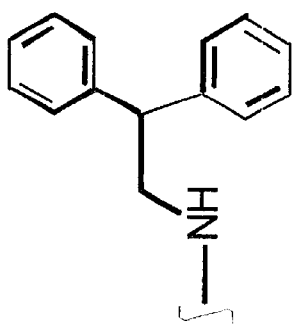
FIG. 13 is a schematic diagram that shows examples of groups that block the channels formed by the helices.
Figure 13:
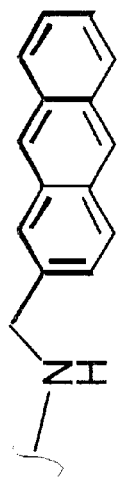
Figure 13:
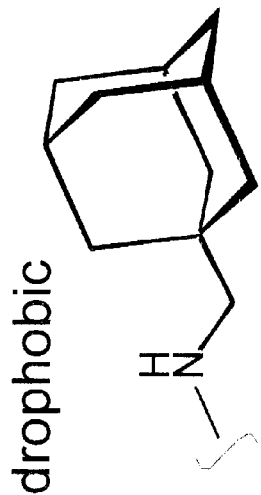
Figure 13:
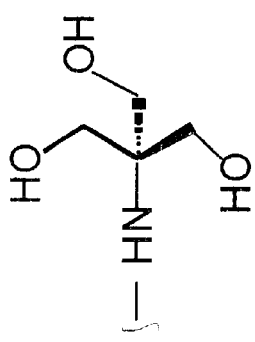
Figure 13:
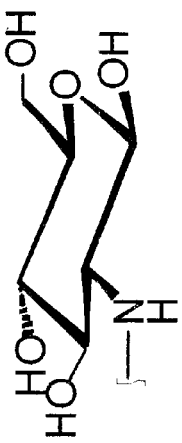
Figure 13:
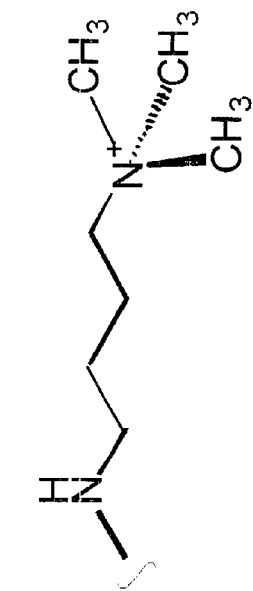
Figure 13:
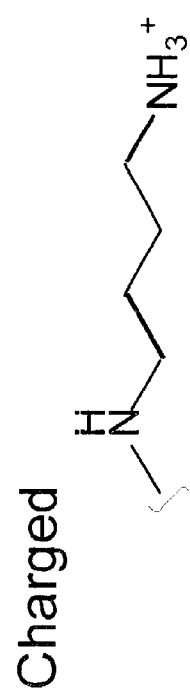

A variety of bulky groups can be used as the group (the "ball" in FIG. 11) that blocks a channel, as shown in FIG. 13. While acting as roadblocks by introducing steric hinderance at either end of a helix, hydrophobic groups may only interact with the internal cavity weakly and thus only "perch" on the helix end. Hydrophilic groups, such as those derived from glucose, sucrose and other carbohydrate molecules may "nest" in the helix cavity due to favorable hydrogen bonding interactions. Charged groups, such as ammonium and quaternary ammonium ions, may also bind in the cavity due to the negative electrostatic potential within the cavity.

Figure 14:
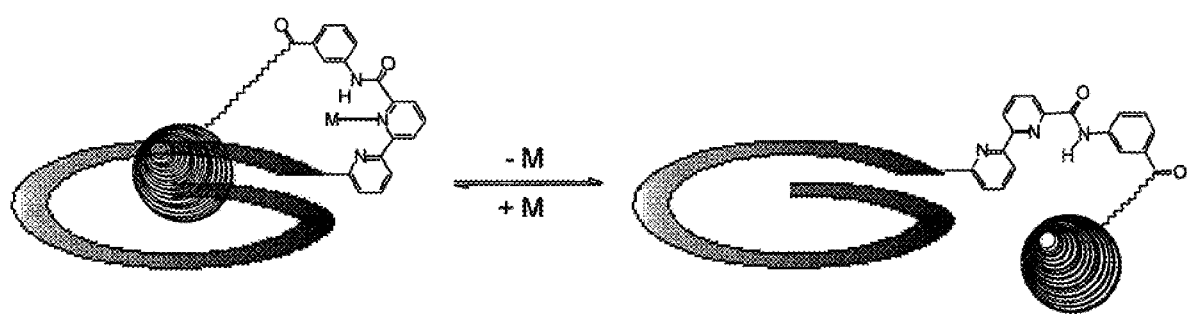
FIG. 14 is a schematic diagram that shows a metal ion complex based switch. The design is similar to that shown in FIG. 11. The bipyridine unit is based on 2,2'-bipyridine-3,3'-dicarboxylic acid.

Similarly, metal ion-chelating reagents can also be used as switches, the ion- and small molecule-conducting ability of the tubes will be blocked, resulting in meta ion-adjusted molecular gates. One example is schematically shown in FIG. 14.

Such modified helices can be directed to a tumor by tumor-specific antibodies and then activated, leading to the selective targeting of tumor cells. The advantage of light switches is that light does not interfere with many natural processes, and it can be applied with exquisite spatial and temporal control. These techniques can be used for drug delivery as well. For example, drugs can be transported inside liposomes and, with the help of molecular switches, released on command through artificial pores planted on the membrane.

3. Nanoporous Films for Highly Efficient Nanofiltration

Figure 15:
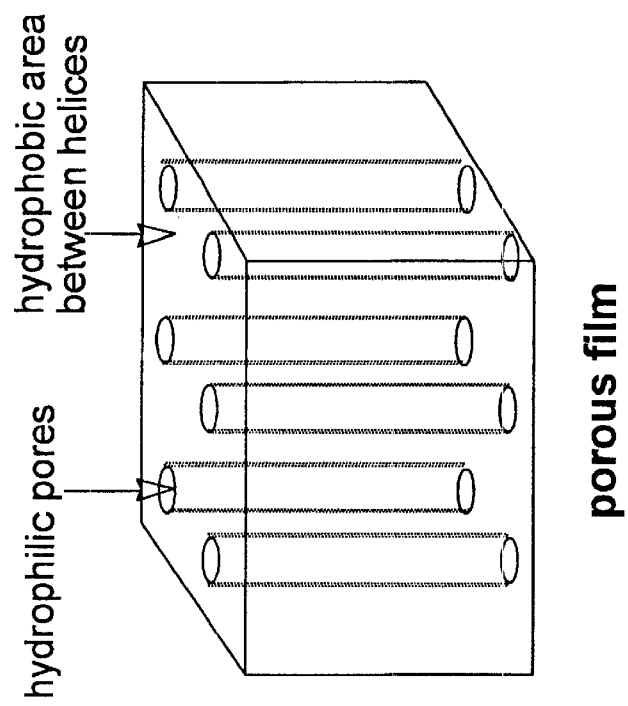
FIG. 15 is a schematic diagram showing hollow helices formed into porous films.
Figure 15:
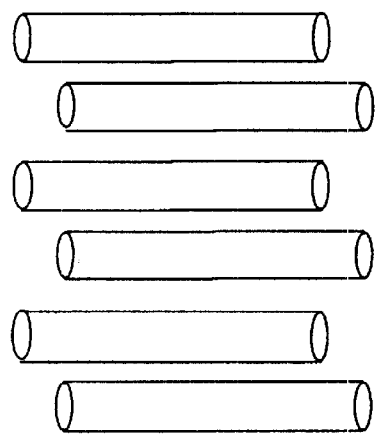

Materials of the type shown in FIG. 15 represent examples of nanoporous polymer films with a unique pore size. Furthermore, by adjusting the interior diameters of the helices, the pore size can be changed at the nanometer scale. Such materials have numerous important applications. Three examples of these applications are discussed below.

While almost all of the porous polymeric materials previously available have pore sizes that are represented by a Gaussian distribution, the helical polymers of the present invention are useful for forming porous materials with a single pore size. Nanoporous membranes consisting of such polymers lead to significant enhancement in both permeate influx and solute selectivity. One particular application involves waste water treatment. The hydrophilic pores facilitate the passage of water molecules and retain many hydrophobic and large size hydrophilic molecules. Furthermore, the hydrophilic nature of the pores greatly alleviates the fouling problem that is associated with most currently available organic membranes.

4. Confinement and Parallel Alignment of Guest Molecules

Figure 16:
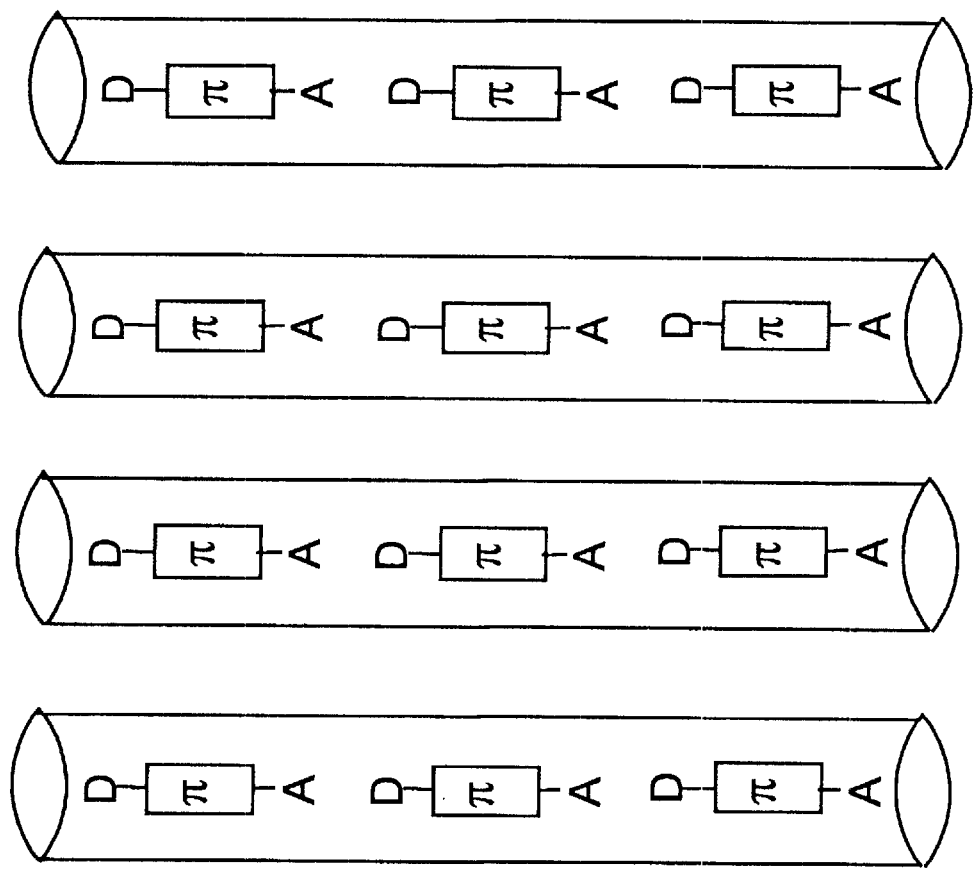
FIG. 16 is a schematic diagram showing confinement and parallel alignment of guest molecules.
Figure 17:
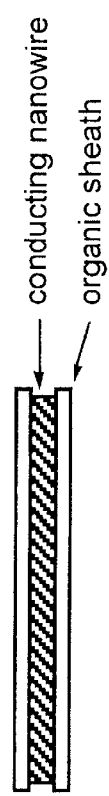
FIG. 17 is a schematic diagram showing a template for fabricating conducting nanowires.

Confining close-packed, functionalized molecules within parallel-aligned porous channels addresses a number of interesting physical properties, especially when the guest molecules themselves are aligned co-parallel within the cavities. These properties include: (1) optical effects; (2) non-linear optical (NLO) effects; (3) transport of charge carriers along the channels; and (4) magnetic phenomena. A design of novel NLO materials is shown in FIG. 16.

The highly polarizable, rod-like dipolar guest molecules (D=electron donor, A=electron acceptor), which otherwise tend to pack head-to-tail to minimize electrostatic repulsion, are forced into polar packing in the chiral channels. Polar packing is an essential condition for NLO properties such as second harmonic generation and linear electro-optic effect. Repulsion between guests in neighboring channels are minimized due to both the (left- or right-handed) chirality of the channels and the adjustable distance between the channels (by varying side groups). Until the present invention, no such organic/polymeric materials were available. The only approach used inorganic zeolites. Due to the much greater processibility of polymers, this class of materials are very useful for such applications.

A specific example of a guest molecule is shown below:

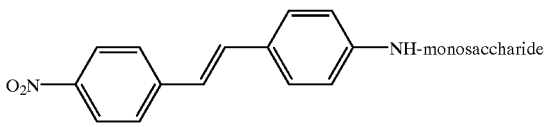

A monosaccharide residue is attached to the NLO chromophore to ensure strong binding to the hydrophilic channels. The sugar residue also ensures a polar assembly of the resulting host-guest materials even if a racemic mixture of the helices is used, because a pair of diastereomeric complexes will be generated in this case. This approach combines the robustness and processibility of polymers and the flexibility of host-guest interactions.

5. Templates for Fabricating Conducting Nanowires

The nanoporous polymers are also used as templated for manufacturing conducting metal wires with diameters in the nanometer range. This approach is shown schematically in FIG. 17.

The electrostatically negative channel featured by amide carbonyl O atoms facilitate the absorption of metal ions which is then reduced into metal atoms. The organic templates are either burned away or kept as insulating sheaths.

The present invention provides an entirely new class of oligomers with unique folded structures that contribute to both basic and applied research activities. Gated channels or pores with various switches find applications in designing a variety of important molecules devices. For example, highly selective sensors can be synthesized based on these novel molecular tubes. These molecules have great potential as drugs, drug carriers, and building blocks for larger structures.

One skilled in the art will readily appreciate that the present invention is well adapted to carry out of the objects and obtain the ends and advantages mentioned, as well as those inherent therein. The present example along with the methods, procedures, treatment, molecules and specific compounds described herein are presently representative of preferred embodiments, are exemplary, and are not intended as limitations on the scope of the invention. Changes therein and other uses will occur those skilled in the art which are encompassed within the spirit of the invention as defined by the scope of the claims. Any patents or publications mentioned in this specification are indicative of the levels of those skilled in the art to which the invention pertains. These patents and publications are herein incorporated by reference to the same extent as if each individual publication was specifically and individually indicated to be incorporated by reference.

Having described presently preferred embodiments of the invention, it is to be understood that there may be other embodiments which are within the scope of the appended claims.

I claim:

1. A helical composition comprising a plurality of aromatic substituents linked by at least one amide group, the composition having a curved backbone due at least in part to intramolecular hydrogen bonds that rigidify the amide linkage of each amide group to each aromatic substituent and at least in part to an interaction between the aromatic substituents, whereby the curved backbone is stabilized, wherein the composition comprises a plurality of aromatic substituents having a Structure A:

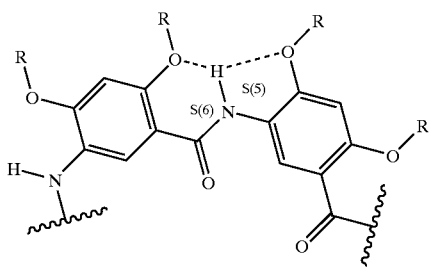

wherein R is selected from linear and branched chain alkyl groups, aryl groups including phenyl, benzyl, napthyl, or alkyl or aryl groups with polar terminal functional ends including —OH, —COOH, —NH$_2$, —NH$_3^+$, —N$^+$R'$_3$, —CH$_2$CH$_2$C$_6$H$_5$, CH$_2$C$_6$H$_4$—p—OH, —CH$_2$COOCH$_3$, —CH$_2$CONH$_2$, CH$_2$CH$_2$CONH$_2$, —CH$_2$COOCH$_2$—(3-indolyol).

2. The composition of claim 1, wherein the backbone of the composition folds back on itself and forms a left-handed helical conformation.

3. The composition of claim 1, wherein the backbone of the composition folds back on itself and forms a right-handed helical conformation.

4. The composition of claim 1, wherein the backbone comprises a structure type I as shown in

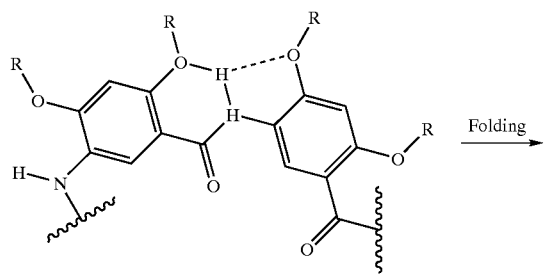

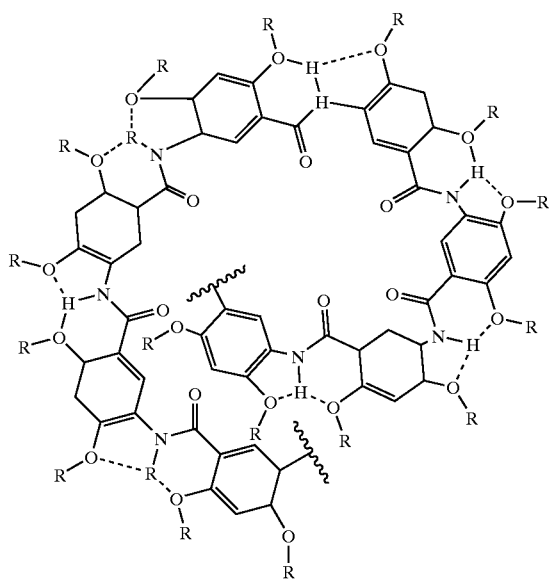

5. The composition of claim 1, wherein the composition comprises a plurality of aromatic substituents having a Structure G:

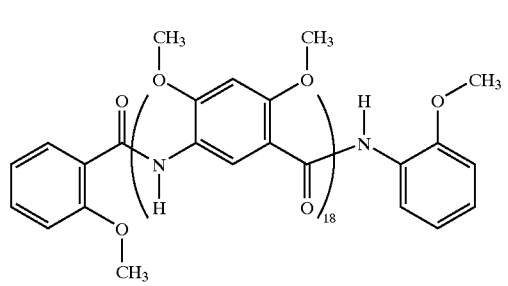

6. The composition of claim 1, wherein the composition comprises a plurality of aromatic substituents having a Structure I:

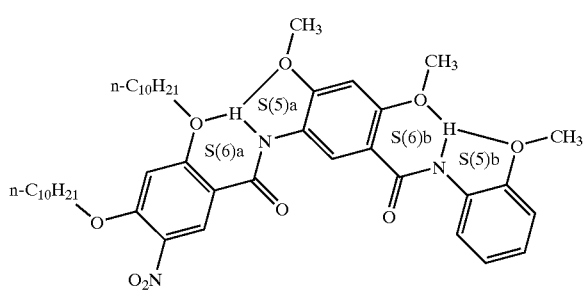

7. The composition of claim 1, wherein the composition comprises a plurality of aromatic substituents having a Structure J wherein n=0–5:

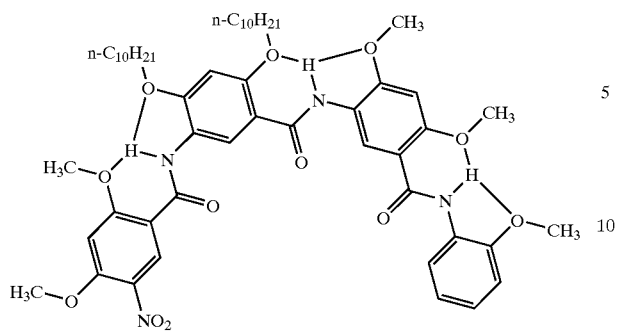

J

8. The composition of claim 1, wherein the composition comprises a plurality of aromatic substituents having a Structure P, wherein $R_1$=n-octyl and $R_2$=n-decyl:

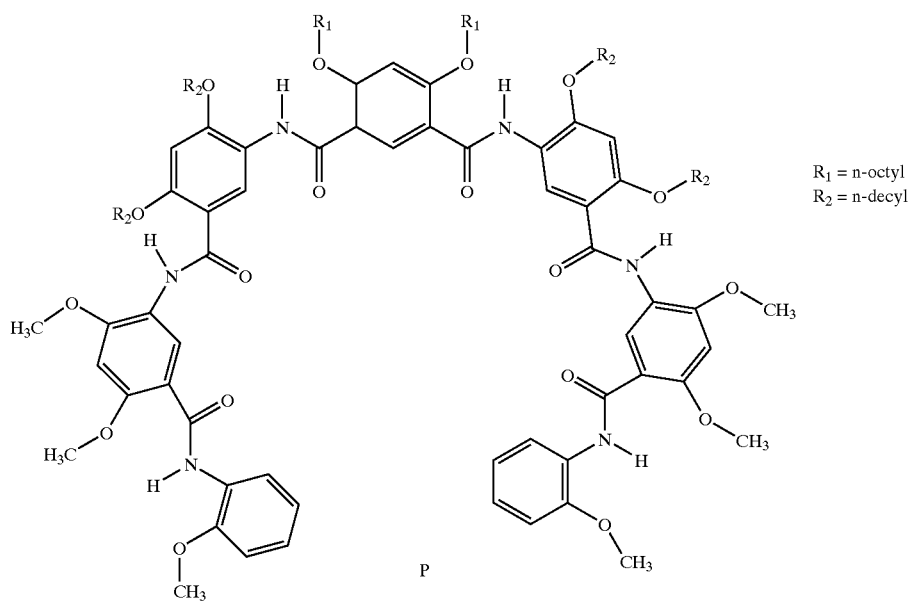

P

9. The composition of claim 1, wherein the compositions comprise met α disubstituted benzene derivatives.

10. The composition of claim 1, wherein the compositions comprise 1, 3 and 4 disubstituted benzene derivatives.

11. The composition of claim 1, wherein the composition has a nanosized tube-like structure.

12. The composition of claim 10, wherein a tube-like structure of the amide-linked composition has a hydrophilic interior and a hydrophobic exterior.

13. The composition of claim 1, wherein the aromatic substituent comprises a plurality of 5-amino-2,4-dihydroxybenzoic acid aromatic substituents.

14. The composition of claim 13, comprising at least 6,5-amino-2,4-dihdroxybenzoic acid aromatic substituents, whereby the composition has a helical conformation.

15. The composition of claim 13, comprising at least 12,5-amino-2,4-dihdroxybenzoic acid aromatic substituents, whereby the composition has a helical conformation.

16. The composition of claim 14, wherein the composition forms a tubular cavity having a diameter of about ~10 Å.

17. The composition of claim 1, wherein the compositions comprise meta- and para-disubstituted benzene derivatives.

18. The composition of claim 17, wherein the composition has the configuration (m,m,m):

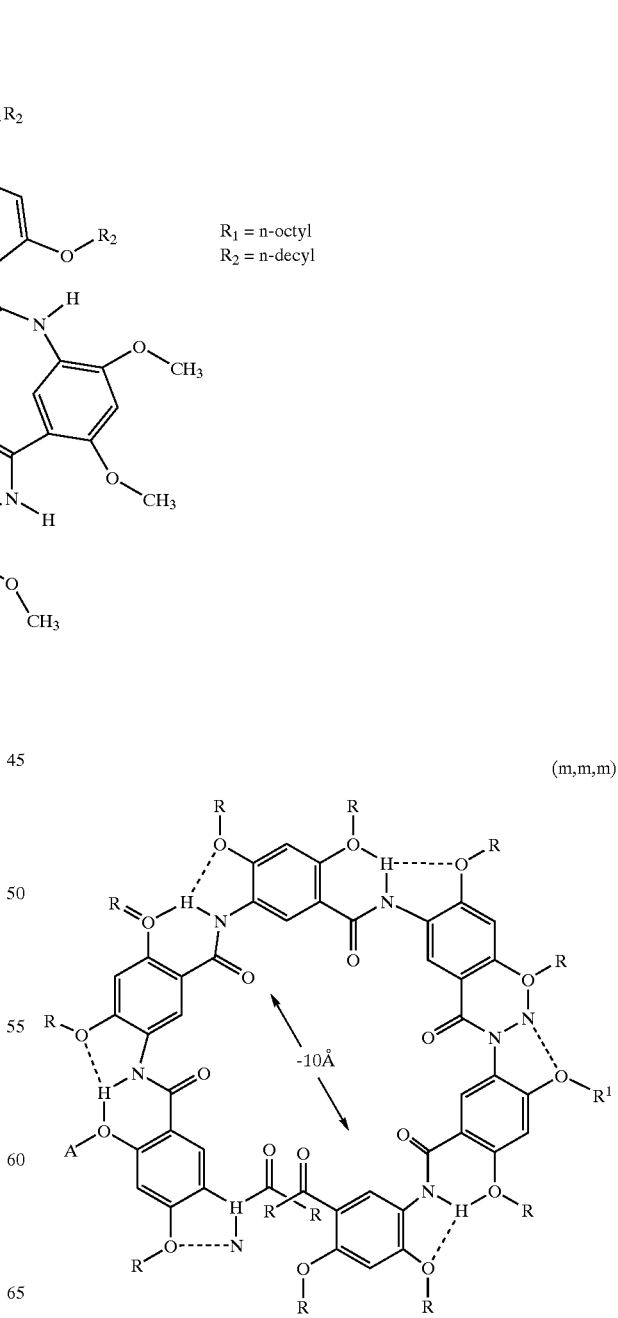

19. The composition of claim 17, wherein the composition has the configuration (m,p,m):
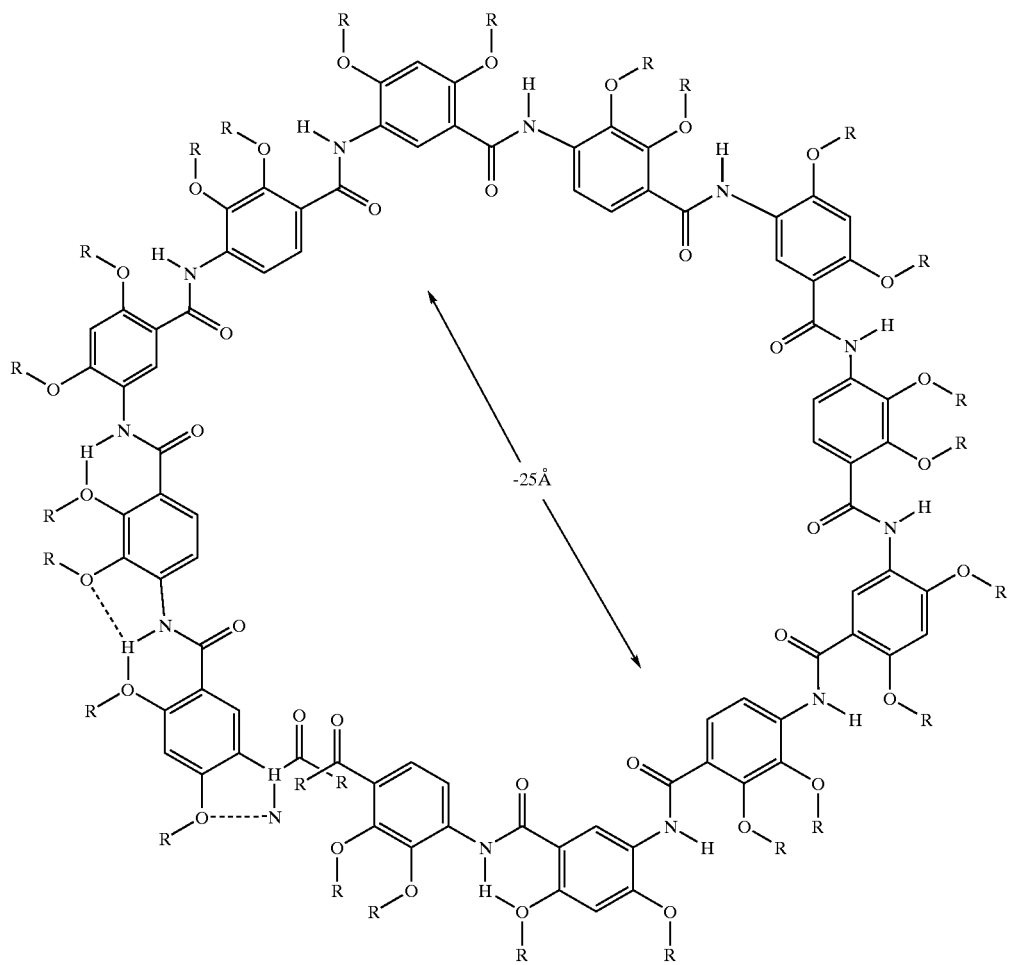
(m,p,m)
20. The composition of claim 17, wherein the composition has the configuration (n,p,p):

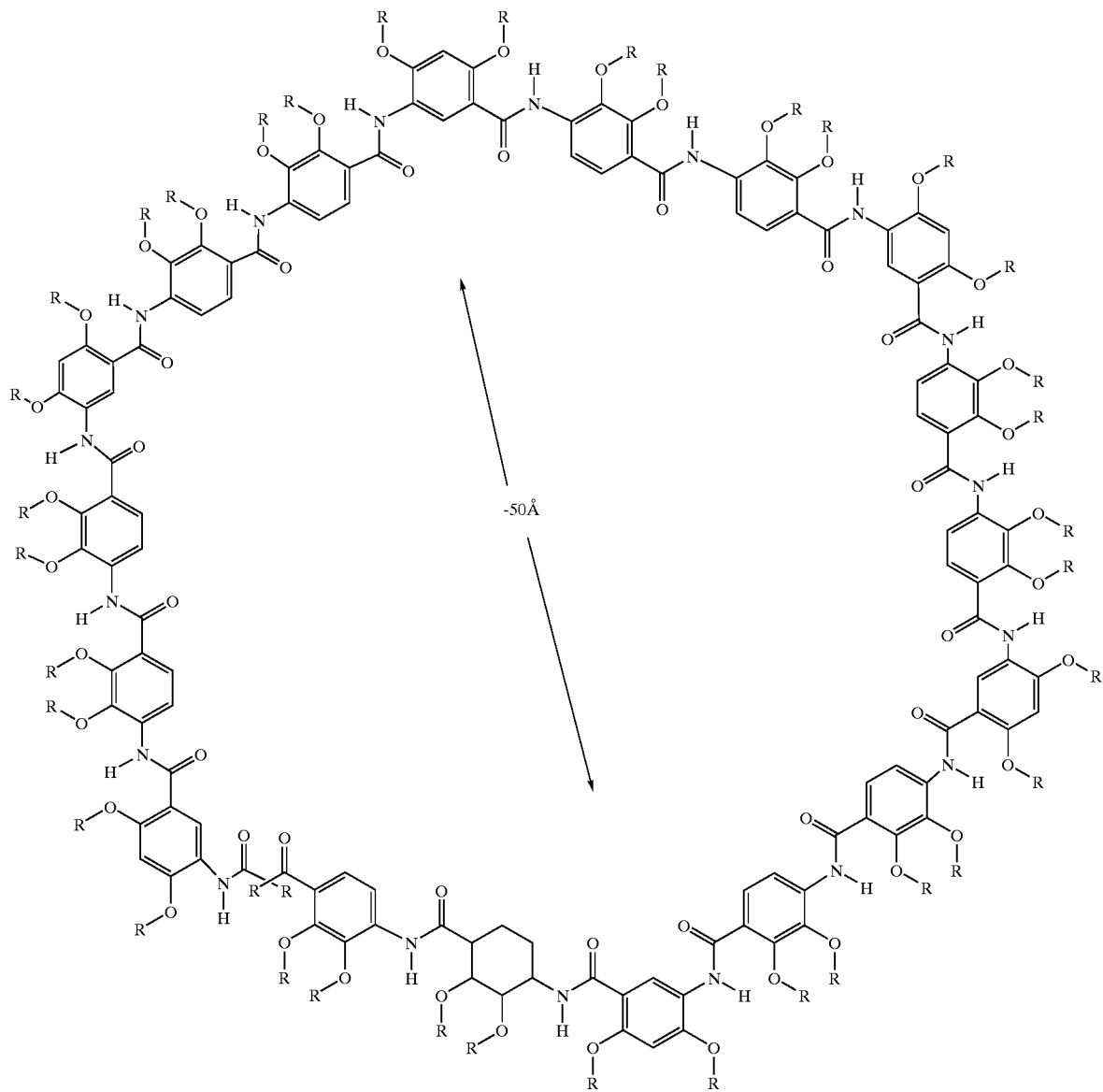

(m,p,p)

21. The composition of claim 1, wherein helical sense of the composition is induced by modifying at least one side group on the aromatic substituent.

22. The composition of claim 21, wherein the helical sense of the composition is induced by covalently linking the outer surface of the helical composition.

23. The composition of claim 22, wherein at least one side group bears free thiol groups that form disulfide bonds upon oxidative cross-linking by using $I_2$.

24. The composition of claim 1, wherein the composition comprises an oligomer.

25. The composition of claim 1, wherein the composition comprises an polymer.

26. The composition of claim 1, wherein the backbone comprises the Structure

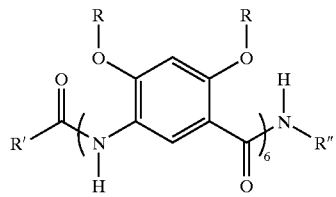

27. The composition of claim 1, wherein the backbone comprises the Structure

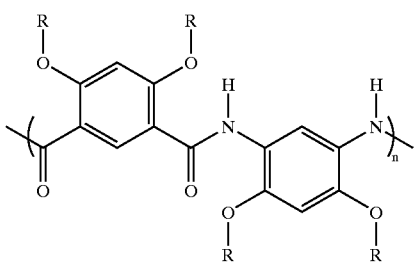

28. The composition of claim 1, wherein the backbone comprises the Structure

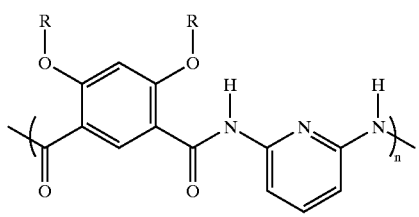

29. The composition of claim 1, having the formula:

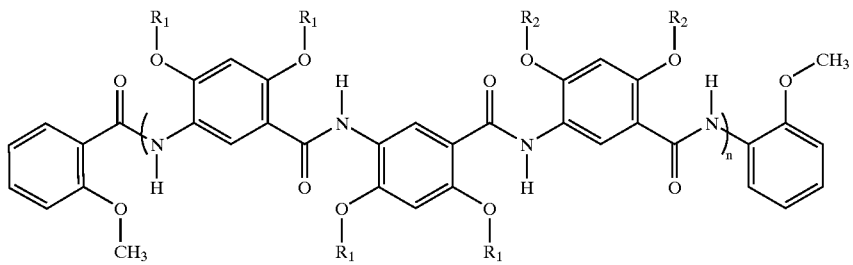

n = 10-20, $R_1$ = isobutyl

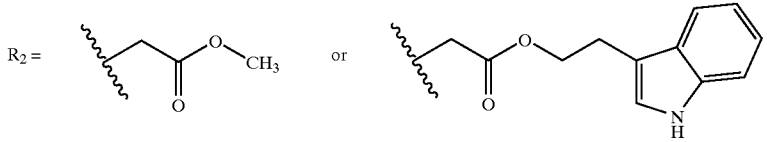

30. The composition of claim 1, wherein an inner surface of the helical conformation has a plurality of amide-O atoms, making the inner surface thereof electrostatically negative and hydrophilic.

31. The compositions of claim 1, wherein an outer surface of the helical composition has a modifiable outer surface.

32. A cytotoxic agent comprising the composition of claim 1.

33. A therapeutic reagent comprising the composition of claim 1, coupled to at least one desired tumor specific antibody.

34. The composition of claim 33, wherein the helical composition bears a free amino group which is linked to at least one Fab fragment of the tumor-specific antibodies.

35. The composition of claim 34, wherein the free amino group is linked to Fab fragments with a heterofunctional cross-linking agent, N-succinimidy 1-3-(2-pyridyidithio) propionate.

36. The helical composition of claim 1, wherein the composition acts as an ion channel for proton transport activity.

37. The composition of claim 1, wherein the helical composition has a molecular switch and defines a channel capable of being opened and closed.

38. The composition of claim 37, wherein the molecular switch is biochemical and is activated by at least one enzyme.

39. The composition of claim 37, wherein the molecular switch is chemical and is activated by binding of small molecules and ions.

40. The composition of claim 37, wherein the molecular switch is activated by at least one physical stimulus.

41. The composition of claim 40, wherein the physical stimulus comprises heat, light, and a combination thereof.

42. The composition of claim 37, wherein the molecular switch is a photoresponsive switch comprising thio indigo which undergoes a cis-trans isomerization upon irradiating by a light source with a wavelength of 550 nm (cis to trans) or 450 nm (trans to cis).

43. The composition of claim 37, wherein the molecular switch comprises at least one metal ion-chelating reagent.

44. The composition of claim 1, wherein the helical composition is used in confinement and parallel alignment of molecules.

45. The helical composition of claim 1, used as a template for producing conducting materials having a diameter in the nanometer range.

46. The composition of claim 4, wherein the side group R determines the outside surface properties of the composition.

47. The composition of claim 46, wherein the composition is a hydrophobic oligomer or polymer where R is selected from linear and branched chain alkyl groups (from one carbon to 20 and longer) and aryl groups including phenyl, benzyl, napthyl and the like.

48. The composition of claim 46, wherein the composition is a hydrophilic oligomer or polymer where R is selected from alkyl or aryl groups with polar terminal functional ends including —OH, —COOH, —$NH_2$, —$NH_3^+$, —$N^+R'_3$ and the like.

49. The composition of claim 46, wherein the composition is a membrane compatible oligomer or polymers where R is selected from —$CH_2CH_2C_6H_5$, —$CH_2C_6H_4$—p—OH, —$CH_2COOCH_3$, —$CH_2CONH_2$, —$CH_2CH_2CONH_2$, or —$CH_2COOCH_2CH_2$—(3-indyol).

50. The composition of claim 26, wherein the side group R determines the outside surface properties of the composition.

51. The composition of claim 50, wherein the composition is a hydrophobic oligomer or polymer where R is selected from linear and branched chain alkyl groups (from one carbon to 20 and longer) and aryl groups including phenyl, benzyl, napthyl and the like.

52. The composition of claim 50, wherein the composition is a hydrophilic oligomer or polymer where R is selected from alkyl or aryl groups with polar terminal functional ends including —OH, —COOH, —NH$_2$, —NH$_3^+$, —N$^+$R'$_3$ and the like.

53. The composition of claim 50, wherein the composition is a membrane compatible oligomer or polymers where R is selected from —CH$_2$CH$_2$C$_6$H$_5$, —CH$_2$C$_6$H$_4$—p—OH, —CH$_2$COOCH$_3$, —CH$_2$CONH$_2$, —CH$_2$CH$_2$CONH$_2$, or —CH$_2$COOCH$_2$CH$_2$—(3-indolyol).

54. The composition of claim 27, wherein the side group R determines the outside surface properties of the composition.

55. The composition of claim 54, wherein the composition is a hydrophobic oligomer or polymer where R is selected from linear and branched chain alkyl groups (from one carbon to 20 and longer) and aryl groups including phenyl, benzyl, napthyl and the like.

56. The composition of claim 54, wherein the composition is a hydrophilic oligomer or polymer where R is selected from alkyl or aryl groups with polar terminal functional ends including —OH, —COOH, —NH$_2$, —NH$_3^+$, —N$^+$R'$_3$ and the like.

57. The composition of claim 54, wherein the composition is a membrane compatible oligomer or polymers where R is selected from —CH$_2$CH$_2$C$_6$H$_5$, —CH$_2$C$_6$H$_4$—p—OH, —CH$_2$COOCH$_3$, —CH$_2$CONH$_2$, —CH$_2$CH$_2$CONH$_2$, or —CH$_2$COOCH$_2$CH$_2$—(3-indolyol).

58. The composition of claim 28, wherein the side group R determines the outside surface properties of the composition.

59. The composition of claim 58, wherein the composition is a hydrophobic oligomer or polymer where R is selected from linear and branched chain alkyl groups (from one carbon to 20 and longer) and aryl groups including phenyl, benzyl, napthyl and the like.

60. The composition of claim 58, wherein the composition is a hydrophilic oligomer or polymer where R is selected from alkyl or aryl groups with polar terminal functional ends including —OH, —COOH, —NH$_2$, —NH$_3^+$, —N$^+$R'$_3$ and the like.

61. The composition of claim 58, wherein the composition is a membrane compatible oligomer or polymers where R is selected from —CH$_2$CH$_2$C$_6$H$_5$, —CH$_2$C$_6$H$_4$—p—OH, —CH$_2$COOCH$_3$, —CH$_2$CONH$_2$, —CH$_2$CH$_2$CONH$_2$, or —CH$_2$COOCH$_2$CH$_2$—(3-indolyol).

\* \* \* \* \*